US010632433B2

(12) United States Patent
Claes et al.

(10) Patent No.: US 10,632,433 B2
(45) Date of Patent: Apr. 28, 2020

(54) DISPOSABLE BIOREACTOR

(75) Inventors: Tom Claes, Bitzen (BE); Jean-Pascal Zambaux, Allonzier la Caille (FR); Steven Vanhamel, Velm (BE); Christophe Braet, Muizen (BE); Florence Bosco, Mignault (BE); Jose Castillo, Brussels (BE)

(73) Assignee: PALL LIFE SCIENCES BELGIUM BVBA, Hoegaarden (BE)

( * ) Notice: Subject to any disclaimer, the term of this patent is extended or adjusted under 35 U.S.C. 154(b) by 2179 days.

(21) Appl. No.: 12/299,271

(22) PCT Filed: May 12, 2007

(86) PCT No.: PCT/US2007/068828
§ 371 (c)(1),
(2), (4) Date: Jul. 31, 2009

(87) PCT Pub. No.: WO2007/134267
PCT Pub. Date: Nov. 22, 2007

(65) Prior Publication Data
US 2010/0015696 A1    Jan. 21, 2010

Related U.S. Application Data

(60) Provisional application No. 60/799,842, filed on May 13, 2006.

(51) Int. Cl.
*C12M 3/00* (2006.01)
*C12M 1/00* (2006.01)
(Continued)

(52) U.S. Cl.
CPC ...... *B01F 13/1013* (2013.01); *B01F 3/04269* (2013.01); *B01F 7/0005* (2013.01);
(Continued)

(58) Field of Classification Search
CPC ...... C12M 27/02; C12M 27/00; C12M 27/04; C12M 29/06
See application file for complete search history.

(56) References Cited

U.S. PATENT DOCUMENTS 1,269,189 A    6/1918  Kadish
1,452,966 A    4/1923  Field
(Continued)

FOREIGN PATENT DOCUMENTS

DE    1557130        4/1970
DE    2017472 A1    11/1971
(Continued)

OTHER PUBLICATIONS

ATMI, Inc. ATMI LifeSciences Newmix Jet-Drive is Your Benchmark for Disposable, Contained, Ultra-Clean Mixing. Launch of Revolutionary Mixing Technology, Apr. 16, 2007, pp. 1-2, Hoegaarden, Belgium.
(Continued)

*Primary Examiner* — Nathan A Bowers
(74) *Attorney, Agent, or Firm* — King & Schickli, PLLC

(57) ABSTRACT

A disposable material processing apparatus, useable as a bioreactor or fermenter, includes a hollow tank (101) and a mixing paddle (110) disposed within the interior of the tank and adapted to mix contents therein. The paddle may be isolated within a flexible sleeve (140). Various functional elements, such as a sparger, sensor, material extraction conduit, material addition conduit, and/or heat exchange element may be provided, and optionally arranged to travel with the paddle within the tank interior. Baffles may protrude into a mixing tank to enhance mixing. A tank and/or sleeve may comprise polymeric film materials.

24 Claims, 32 Drawing Sheets

(51) Int. Cl.
  *B01F 13/10* (2006.01)
  *B01F 11/04* (2006.01)
  *B01F 15/00* (2006.01)
  *C12M 1/04* (2006.01)
  *B01F 7/00* (2006.01)
  *B01F 3/04* (2006.01)
  *B01F 11/00* (2006.01)

(52) U.S. Cl.
  CPC .......... *B01F 11/0088* (2013.01); *B01F 11/04* (2013.01); *B01F 13/1022* (2013.01); *B01F 15/0085* (2013.01); *B01F 15/00831* (2013.01); *B01F 15/00915* (2013.01); *C12M 23/26* (2013.01); *C12M 23/28* (2013.01); *C12M 27/04* (2013.01); *B01F 2003/0439* (2013.01); *B01F 2003/04148* (2013.01); *B01F 2003/04219* (2013.01); *B01F 2003/04312* (2013.01); *B01F 2003/04319* (2013.01); *B01F 2003/04361* (2013.01)

(56) References Cited

U.S. PATENT DOCUMENTS

| | | |
|---|---|---|
| 1,471,332 A | 10/1923 | Greenawalt |
| 1,501,870 A | 7/1924 | Schranz |
| 1,505,204 A | 8/1924 | Kiernan |
| 1,579,382 A | 4/1926 | Mitchell |
| 2,259,243 A | 10/1941 | Daman |
| 2,404,679 A | 7/1946 | Andron |
| 2,615,692 A | 10/1952 | Muller |
| 2,641,412 A | 6/1953 | Byberg |
| 2,877,994 A | 3/1959 | Jones |
| 3,002,895 A | 10/1961 | Freedman |
| 3,010,303 A | 11/1961 | Bochan |
| 3,045,988 A | 7/1962 | Briscoe |
| 3,311,354 A | 3/1967 | Wilson |
| 3,384,354 A | 5/1968 | Migule et al. |
| 3,572,651 A | 3/1971 | Harker |
| 3,647,397 A | 3/1972 | Coleman |
| 3,682,168 A | 8/1972 | Deaton |
| 3,796,417 A | 3/1974 | Kaelin |
| 3,802,470 A | 4/1974 | Coleman |
| 3,854,704 A | 12/1974 | Balas |
| 3,900,186 A | 8/1975 | Balas |
| 3,925,165 A * | 12/1975 | Muller ...................... 435/299.1 |
| 3,962,892 A | 6/1976 | Garlinghouse |
| 4,025,590 A | 5/1977 | Igich |
| 4,036,919 A | 7/1977 | Komedowski et al. |
| 4,061,698 A | 12/1977 | Thornwald |
| 4,100,235 A | 7/1978 | Thornwald |
| 4,112,518 A | 9/1978 | Garlinghouse |
| 4,162,855 A | 7/1979 | Bender |
| 4,204,774 A | 5/1980 | de Bruyne |
| 4,209,259 A | 6/1980 | Rains et al. |
| 4,355,906 A | 10/1982 | Ono |
| 4,356,967 A | 11/1982 | Lunick |
| 4,379,846 A * | 4/1983 | Shkidchenko et al. .... 435/299.1 |
| 4,426,450 A * | 1/1984 | Donofrio ...................... 435/243 |
| 4,465,645 A | 8/1984 | Kaelin |
| 4,493,637 A | 1/1985 | Ganter et al. |
| 4,498,785 A | 2/1985 | de Bruyne |
| 4,596,779 A | 6/1986 | Ono |
| 4,649,118 A | 3/1987 | Anderson |
| 4,668,632 A | 5/1987 | Young |
| 4,711,582 A | 12/1987 | Kennedy |
| 4,783,172 A | 11/1988 | Garg |
| 4,808,348 A | 2/1989 | Rudick |
| 4,870,018 A | 9/1989 | Lehmann |
| 4,978,616 A | 12/1990 | Gaffar |
| 5,002,890 A | 3/1991 | Morrison |
| 5,008,197 A | 4/1991 | Wergeland et al. |
| 5,045,470 A | 9/1991 | Kloss |
| 5,061,448 A | 10/1991 | Mahe |
| 5,183,595 A | 2/1993 | Schussler |
| 5,193,977 A | 3/1993 | Dame |
| RE34,386 E | 9/1993 | Davidson et al. |
| 5,266,486 A | 11/1993 | Fraatz et al. |
| 5,270,207 A | 12/1993 | Matsumura et al. |
| 5,362,642 A | 11/1994 | Kern |
| 5,443,985 A | 8/1995 | Lu et al. |
| 5,456,586 A | 10/1995 | Carson |
| 5,501,971 A | 3/1996 | Carll |
| 5,533,804 A | 7/1996 | Larsson et al. |
| 5,578,012 A | 11/1996 | Karmen et al. |
| 5,633,165 A | 5/1997 | Swartz |
| 5,727,878 A | 3/1998 | Sullivan |
| 5,750,440 A | 5/1998 | Vanell et al. |
| 5,779,359 A | 7/1998 | Gambrill et al. |
| 5,803,137 A | 9/1998 | Shimotoyodome |
| 5,938,325 A | 8/1999 | Edwards |
| 5,941,635 A | 8/1999 | Stewart |
| 5,988,422 A | 11/1999 | Vallot |
| 6,071,005 A | 6/2000 | Ekambaram et al. |
| 6,077,356 A | 6/2000 | Bouchard |
| 6,178,925 B1 | 1/2001 | Sturm et al. |
| 6,186,932 B1 | 2/2001 | Vallot |
| 6,219,871 B1 | 4/2001 | Frederick et al. |
| 6,234,666 B1 | 5/2001 | Kolb |
| 6,245,555 B1 | 6/2001 | Curtis |
| 6,247,840 B1 | 6/2001 | Gaffar |
| 6,250,796 B1 | 6/2001 | Huang |
| 6,258,394 B1 | 7/2001 | Hochstein |
| 6,391,638 B1 | 5/2002 | Shaaltiel |
| 6,432,698 B1 | 8/2002 | Gaugler |
| 6,439,756 B1 | 8/2002 | Forschner et al. |
| 6,494,613 B2 | 12/2002 | Terentiev |
| 6,634,783 B2 | 10/2003 | Baron |
| 6,670,169 B1 | 12/2003 | Schob et al. |
| 6,670,171 B2 | 12/2003 | Carll et al. |
| 6,673,532 B2 | 1/2004 | Rao |
| 6,837,610 B2 | 1/2005 | Cadogan et al. |
| 6,844,186 B2 | 1/2005 | Carll |
| 6,908,223 B2 | 6/2005 | Bibbo et al. |
| 6,923,567 B2 | 8/2005 | Bibbo et al. |
| 7,025,234 B2 | 4/2006 | Priebe et al. |
| 7,153,021 B2 | 12/2006 | Goodwin et al. |
| 7,249,880 B2 | 7/2007 | Zambaux |
| 7,278,780 B2 | 10/2007 | Goodwin et al. |
| 7,384,027 B2 | 6/2008 | Terentiev |
| 7,431,494 B2 | 10/2008 | Zambaux |
| 7,469,884 B2 | 12/2008 | Terentiev |
| 7,659,108 B2 * | 2/2010 | Schmid ...................... 435/293.1 |
| 2001/0039369 A1 | 11/2001 | Terentiev |
| 2002/0082173 A1 | 7/2002 | Terentiev |
| 2002/0091371 A1 | 7/2002 | Ritter |
| 2002/0105856 A1 | 8/2002 | Terentiev |
| 2002/0118594 A1 | 8/2002 | Vellinger et al. |
| 2002/0145940 A1 | 10/2002 | Terentiev |
| 2002/0172092 A1 | 11/2002 | Reeder et al. |
| 2003/0226857 A1 | 12/2003 | Bibbo et al. |
| 2003/0231546 A1 | 12/2003 | Bibbo |
| 2004/0027912 A1 | 2/2004 | Bibbo et al. |
| 2004/0047232 A1 | 3/2004 | Terentiev |
| 2004/0062140 A1 | 4/2004 | Cadogan et al. |
| 2004/0095842 A1 | 5/2004 | Weetman |
| 2004/0121453 A1 | 6/2004 | Rao |
| 2004/0218468 A1 | 11/2004 | Terentiev |
| 2004/0221897 A1 | 11/2004 | Schubmehl et al. |
| 2004/0252582 A1 | 12/2004 | Bucher |
| 2005/0002274 A1 | 1/2005 | Terentiev |
| 2005/0078552 A1 | 4/2005 | Zambaux |
| 2005/0117449 A1 | 6/2005 | Terentiev |
| 2005/0127215 A1 | 6/2005 | Lienhart et al. |
| 2005/0201201 A1 | 9/2005 | Terentiev |
| 2005/0239199 A1 | 10/2005 | Kunas et al. |
| 2005/0272146 A1 | 12/2005 | Hodge et al. |
| 2005/0282269 A1 | 12/2005 | Proulx |
| 2006/0092761 A1 | 5/2006 | Terentiev |
| 2006/0131765 A1 | 6/2006 | Terentiev et al. |
| 2006/0270036 A1 | 11/2006 | Goodwin et al. |
| 2007/0030759 A1 | 2/2007 | Terentiev |
| 2007/0201993 A1 | 8/2007 | Terentiev et al. |
| 2007/0220956 A1 | 9/2007 | Terentiev |

(56) References Cited

U.S. PATENT DOCUMENTS

| | | |
|---|---|---|
| 2007/0252290 A1 | 11/2007 | Terentiev et al. |
| 2007/0263484 A1 | 11/2007 | Terentiev et al. |
| 2008/0031082 A1 | 2/2008 | Zambaux |
| 2009/0130757 A1 | 5/2009 | Terentiev |

FOREIGN PATENT DOCUMENTS

| | | |
|---|---|---|
| DE | 3246330 | 6/1984 |
| DE | 3407370 A1 | 8/1985 |
| DE | 3818776 | 7/1989 |
| DE | 19542227 | 5/1997 |
| DE | 29800818 U1 | 3/1998 |
| DE | 19705118 | 8/1998 |
| DE | 20114076 | 10/2001 |
| DE | 10 2004 013 078 | 10/2005 |
| EP | 0033292 | 8/1981 |
| EP | 0172478 A1 | 2/1986 |
| EP | 0200792 | 11/1986 |
| EP | 0343885 | 11/1989 |
| EP | 0433463 | 6/1991 |
| EP | 0590473 | 4/1994 |
| EP | 1462155 | 9/2004 |
| EP | 1473358 A2 | 11/2004 |
| EP | 1479758 A2 | 11/2004 |
| GB | 691048 | 5/1953 |
| GB | 1 464 733 | 2/1977 |
| GB | 1464733 | 2/1977 |
| GB | 2076677 | 12/1981 |
| GB | 2202549 | 9/1988 |
| JP | 51-057064 | 5/1976 |
| JP | 56106778 | 8/1981 |
| JP | 59094696 | 5/1984 |
| JP | 61067476 | 4/1986 |
| JP | 61212275 | 9/1986 |
| JP | 61212276 | 9/1986 |
| JP | 631626 | 1/1988 |
| JP | 63036825 | 2/1988 |
| JP | 63-046759 | 3/1988 |
| JP | 03242297 | 10/1991 |
| JP | 6153902 | 6/1994 |
| JP | 07-108154 | 4/1995 |
| JP | 08-318148 | 12/1996 |
| JP | 10-337461 | 12/1998 |
| JP | 10313718 | 12/1998 |
| JP | 10314569 | 12/1998 |
| JP | 11-267488 | 10/1999 |
| JP | 2000126576 | 5/2000 |
| JP | 2003-002393 | 1/2003 |
| NL | 8203579 | 4/1984 |
| WO | 8606618 | 11/1986 |
| WO | 9833538 | 8/1998 |
| WO | 0011953 | 3/2000 |
| WO | 0128608 | 4/2001 |
| WO | 0241484 | 5/2002 |
| WO | 02062458 | 8/2002 |
| WO | WO 03/006633 | 1/2003 |
| WO | 03028869 A2 | 4/2003 |
| WO | 2005037658 | 4/2005 |
| WO | 2005118771 | 12/2005 |
| WO | 2006002091 | 1/2006 |
| WO | 2006063087 | 6/2006 |
| WO | 2007039600 | 4/2007 |
| WO | 2007050971 A1 | 5/2007 |
| WO | WO 2007/134267 | 11/2007 |
| WO | WO 2008/005611 | 1/2008 |
| WO | 2008040567 | 4/2008 |
| WO | 2008040568 | 4/2008 |

OTHER PUBLICATIONS

Bosco et al., ATMI completes its NEWMIX range with ARTELIS single-use mixing technology, pp. 1, posted publicly exhibited at Bioproduction Dublin Conference, Dublin, Ireland, Oct. 24, 2006.
GE Healthcare Life Sciences—WAVE Bioreactor Home, WAVE Bioreactor Systems, http://www4.gelifesciences.com/APTRIX/upp01077.nsf/Content/wave_bioreactor_home, pp. 1-2, downloaded Jan. 4, 2010, General Electric Co., Schenectady, New York.
Hyclone Americas, Mixtainer, An Integrated single-use sterile system for mixing and maintaining homogenous aqueous solutions, pp. 1-2, believed to be available at least as early as Jul. 12, 2007.
Disposable Bioreactors Gaining Favor, New Components and Systems Improve Process Reliability and Reduce Cost, Genetic Engineering & Biotechnology News, Jun. 15, 2006, vol. 26, No. 12, pp. 1-8.
Russ Musch, Product Brief Form for HyClone Bioprocess Containers, May 31, 2001, pp. 1-3.
LevTech, Inc. Business Plan, Sep. 5, 2000, pp. 1, 8-9, 11-13, 25.
Mechanical drawing of Bottom Drain Barrel believed to have been sold by Hyclone Laboratories, Inc. at least as early as Jan. 2002, as cited in U.S. Pat. No. 7,278,780.
ATMI Newmix-Levtech Disposable Mixing and Storage System, ATMI, Danbury, CT downloaded from www.atmi-lifesciences.com/html/newmix.html on Jan. 4, 2010.
Pending claims in U.S. Appl. No. 12/444,040, filed Apr. 2, 2009 (national stage of PCT/EP0753998).
United States Postal Service, Mailing Standards of the United States Postal Service Publication 52—Hazardous, Restricted, and Perishable Mail, Jul. 1999, p. 315.
Schoeb, A Bearingless Motor for a Left Ventricular Assist Device, 7th International Symposium on Magnetic Bearings, Zurich, Switzerland, Aug. 23-25, 2000.

\* cited by examiner

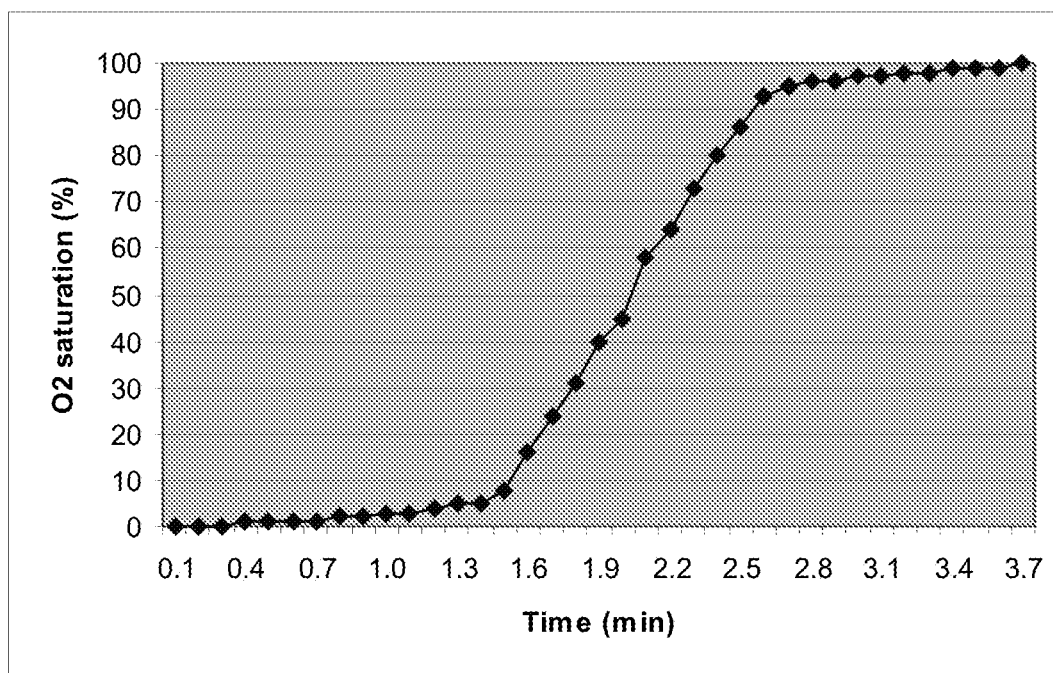
FIG._1

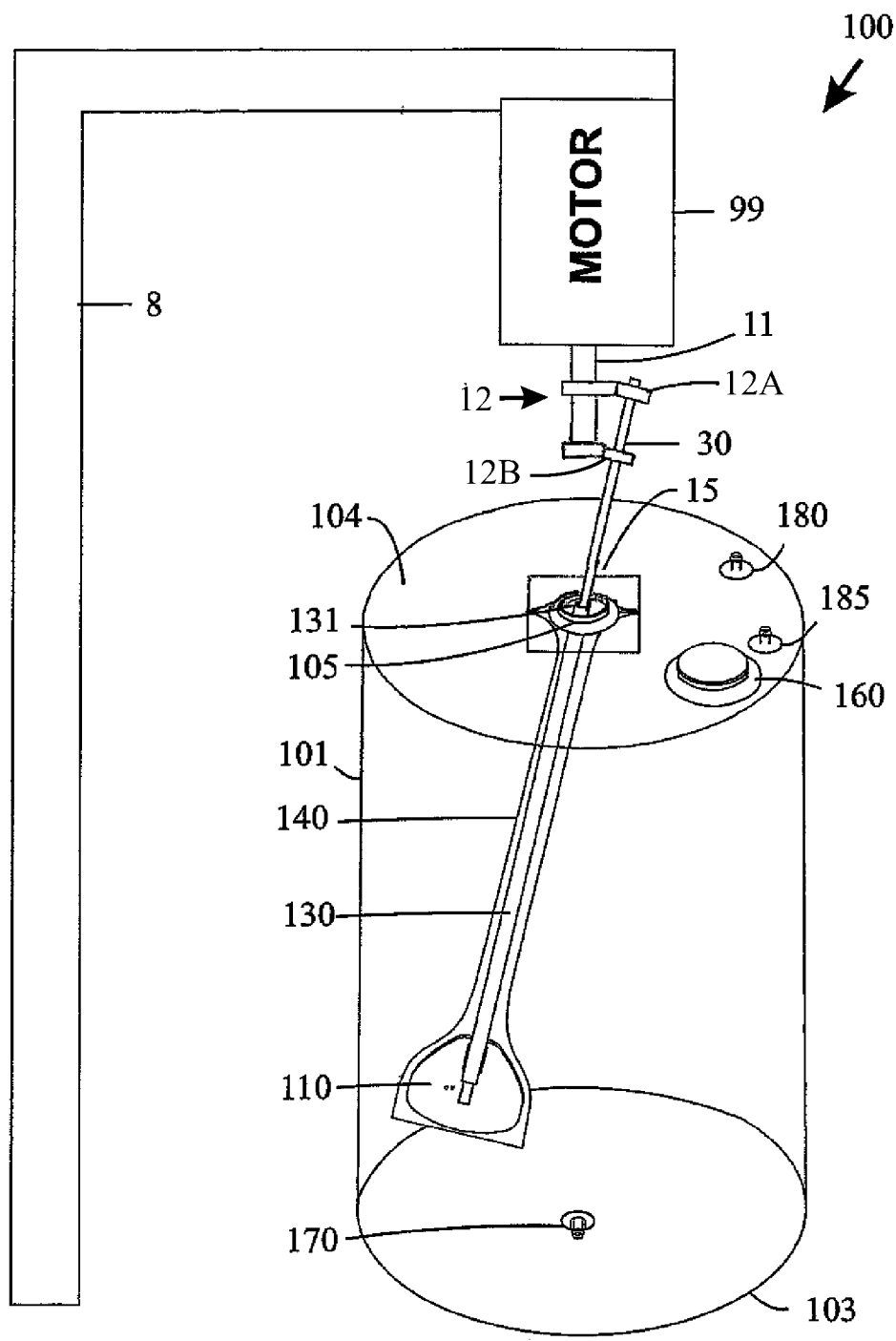
FIG._2A

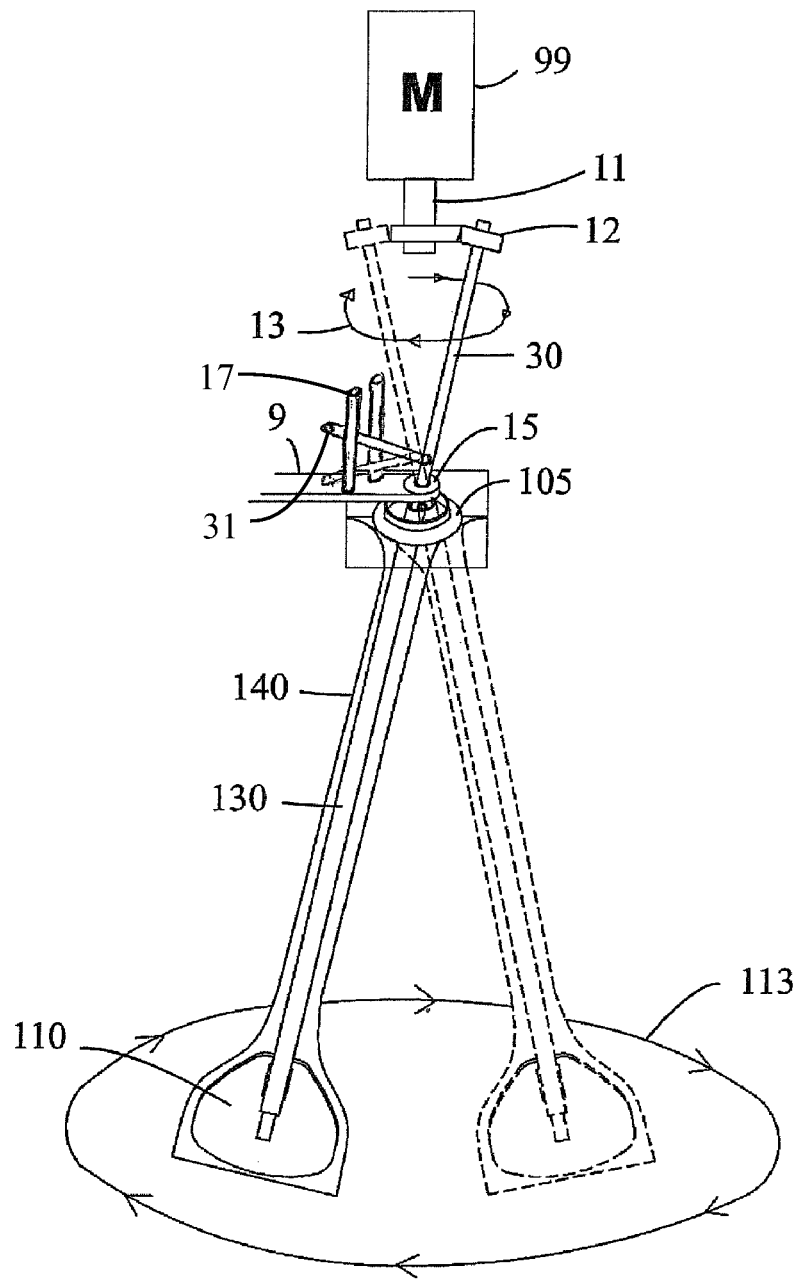
FIG._2B

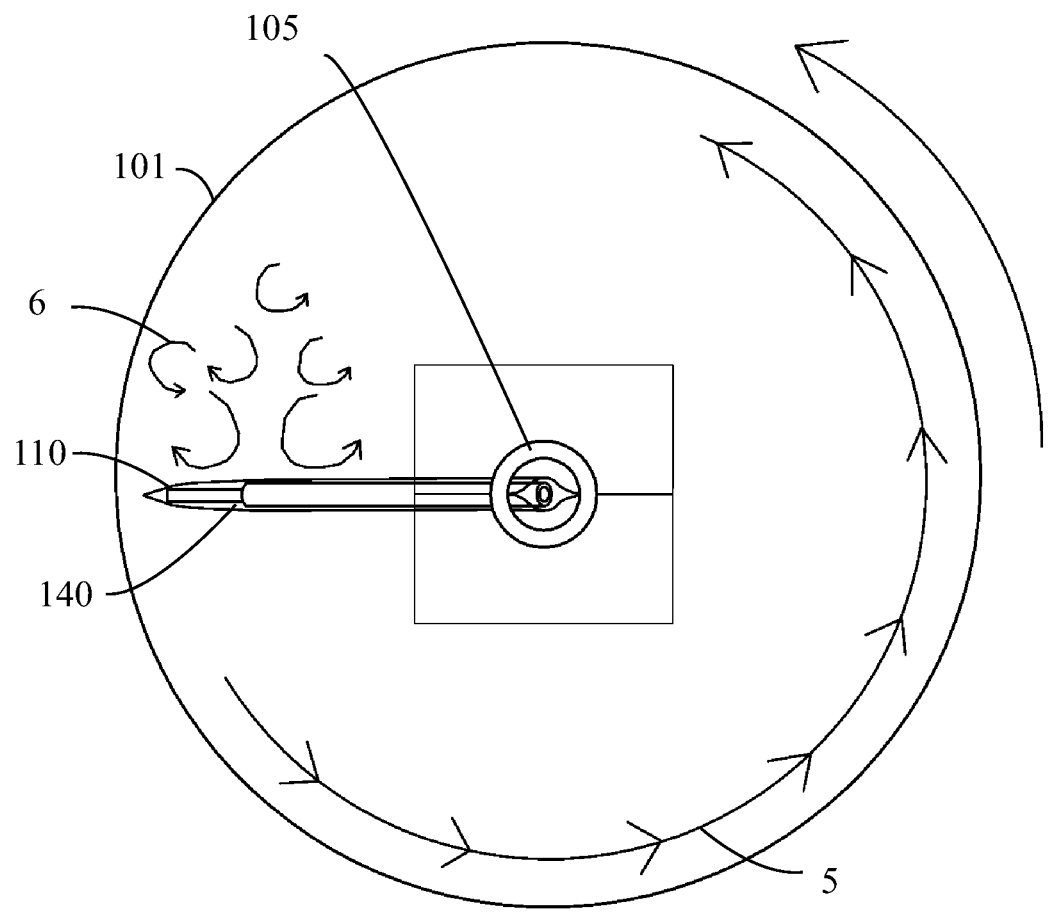
FIG._3A

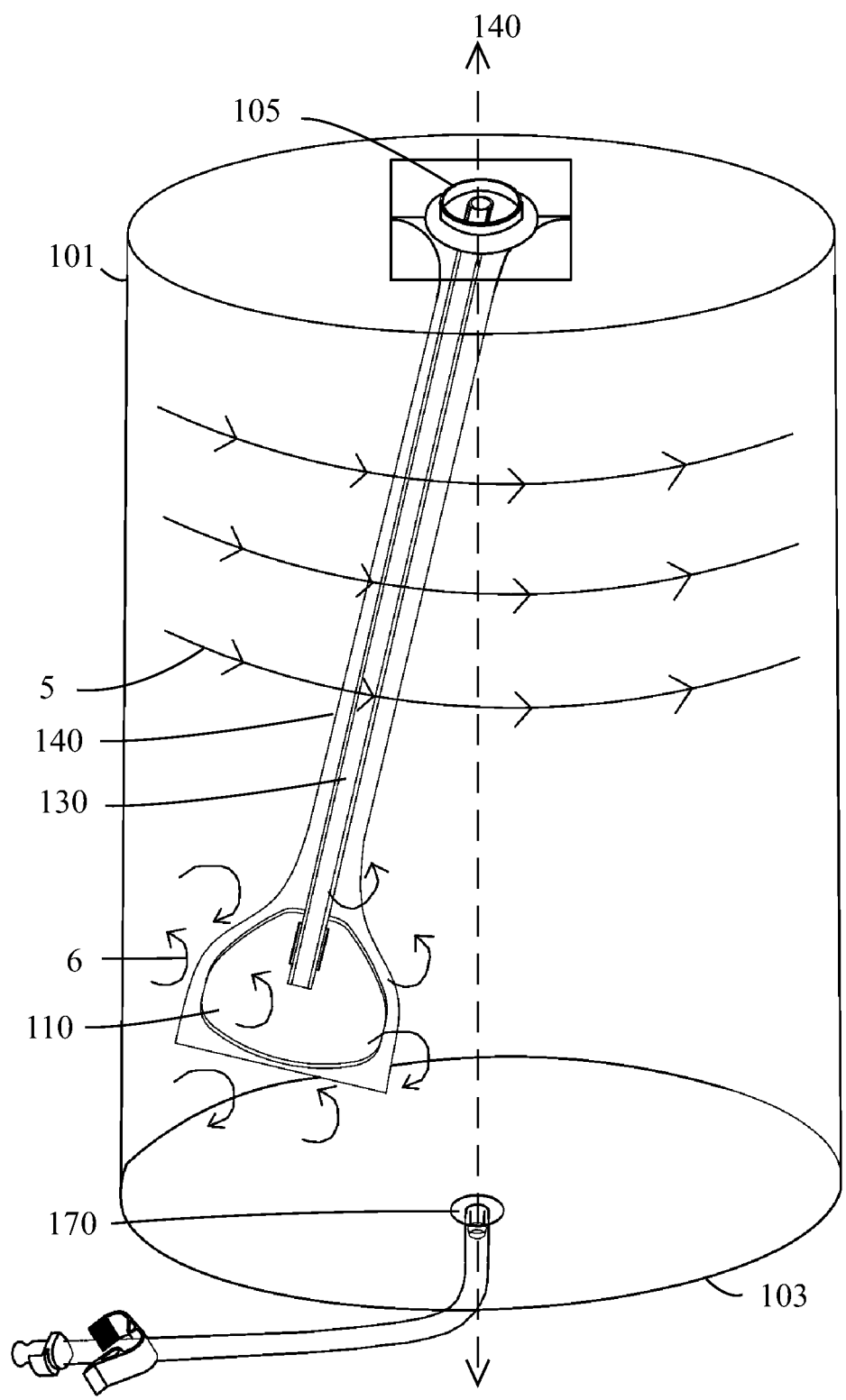
FIG._3B

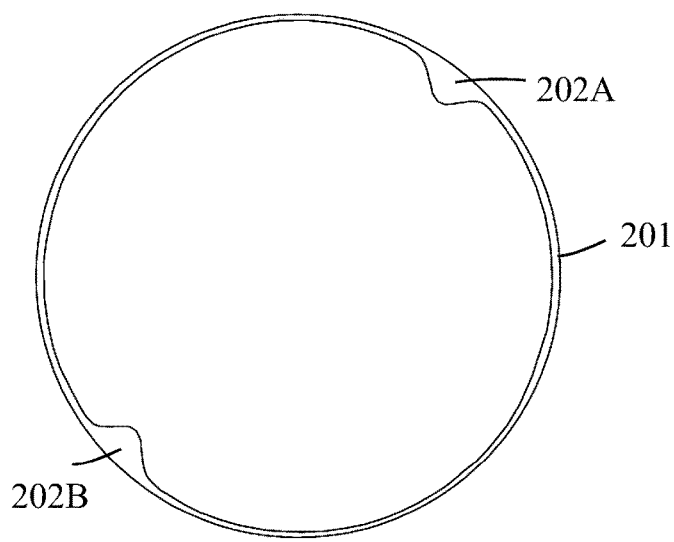
FIG._4A
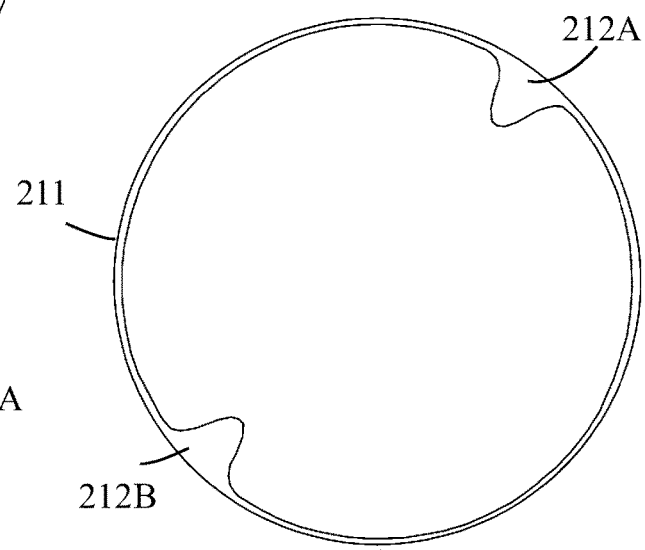
FIG._4B
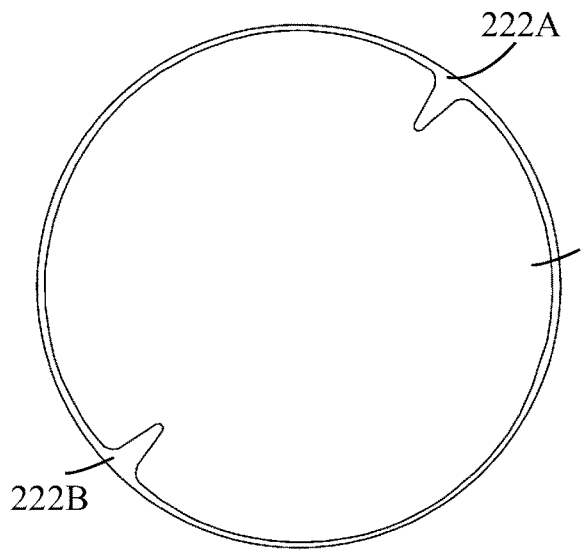
FIG._4C
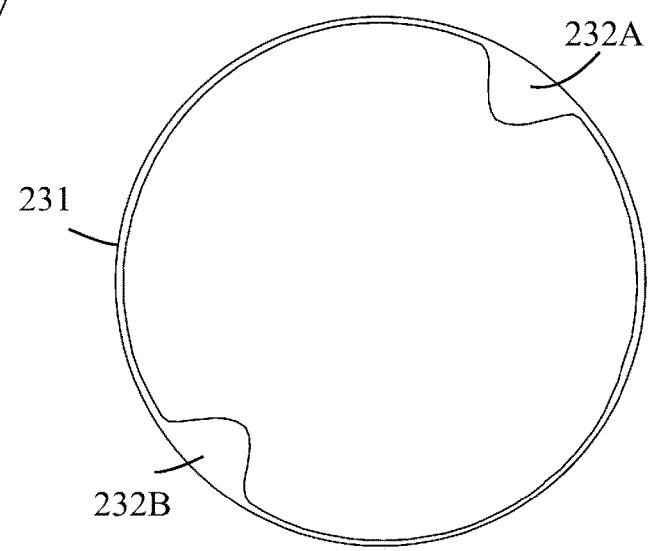
FIG._4D

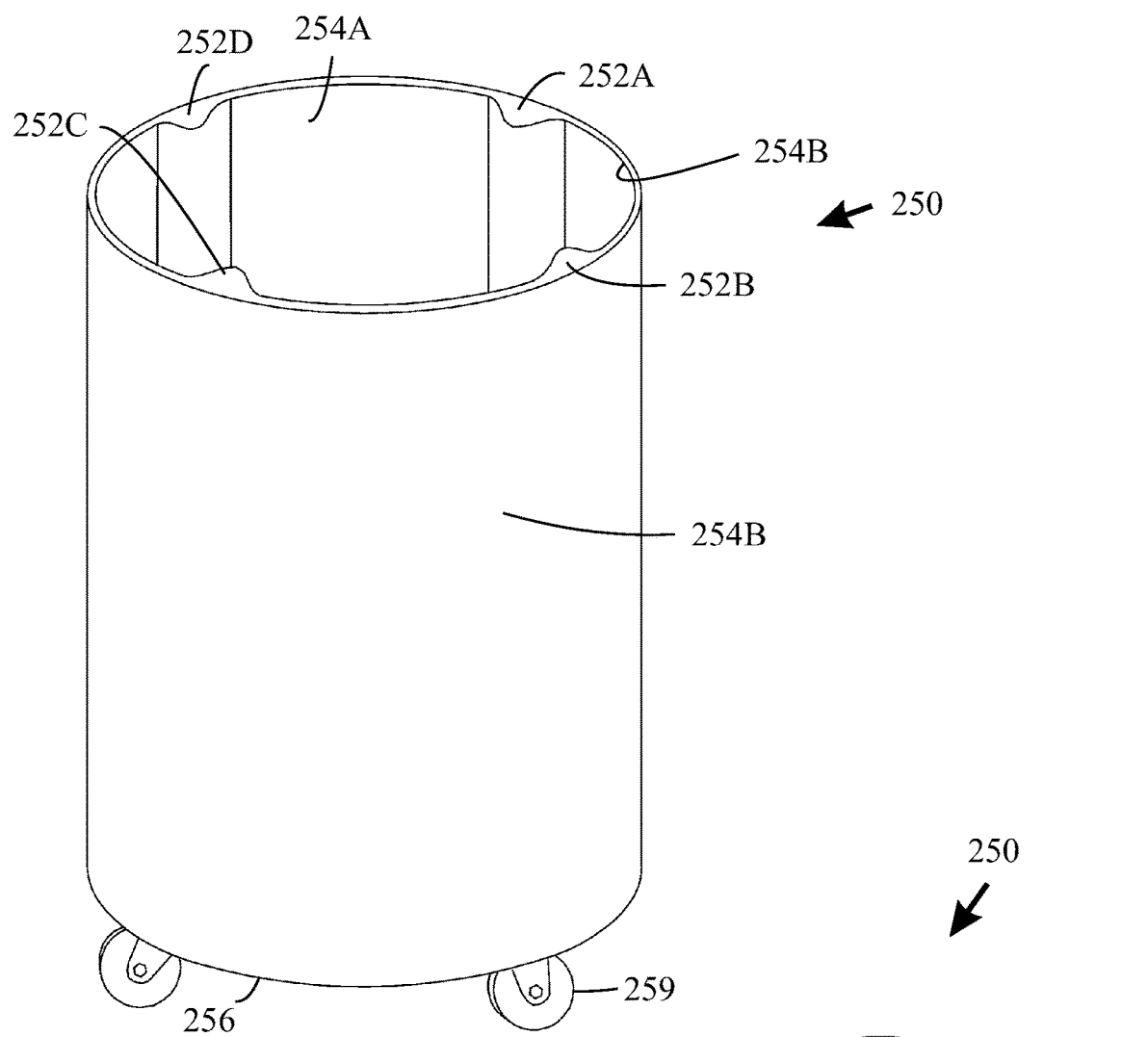
FIG._5A
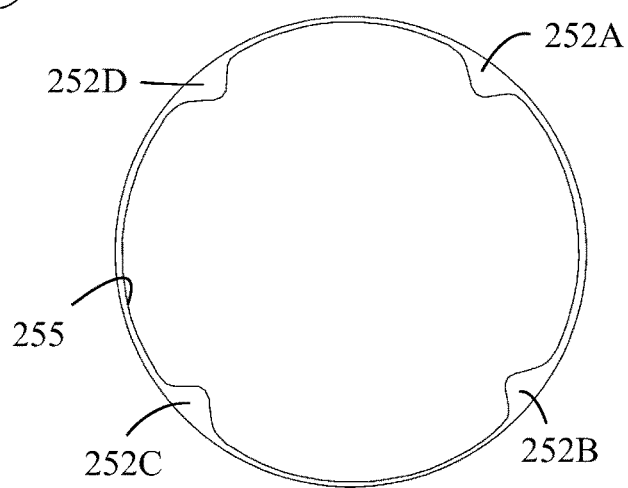
FIG._5B

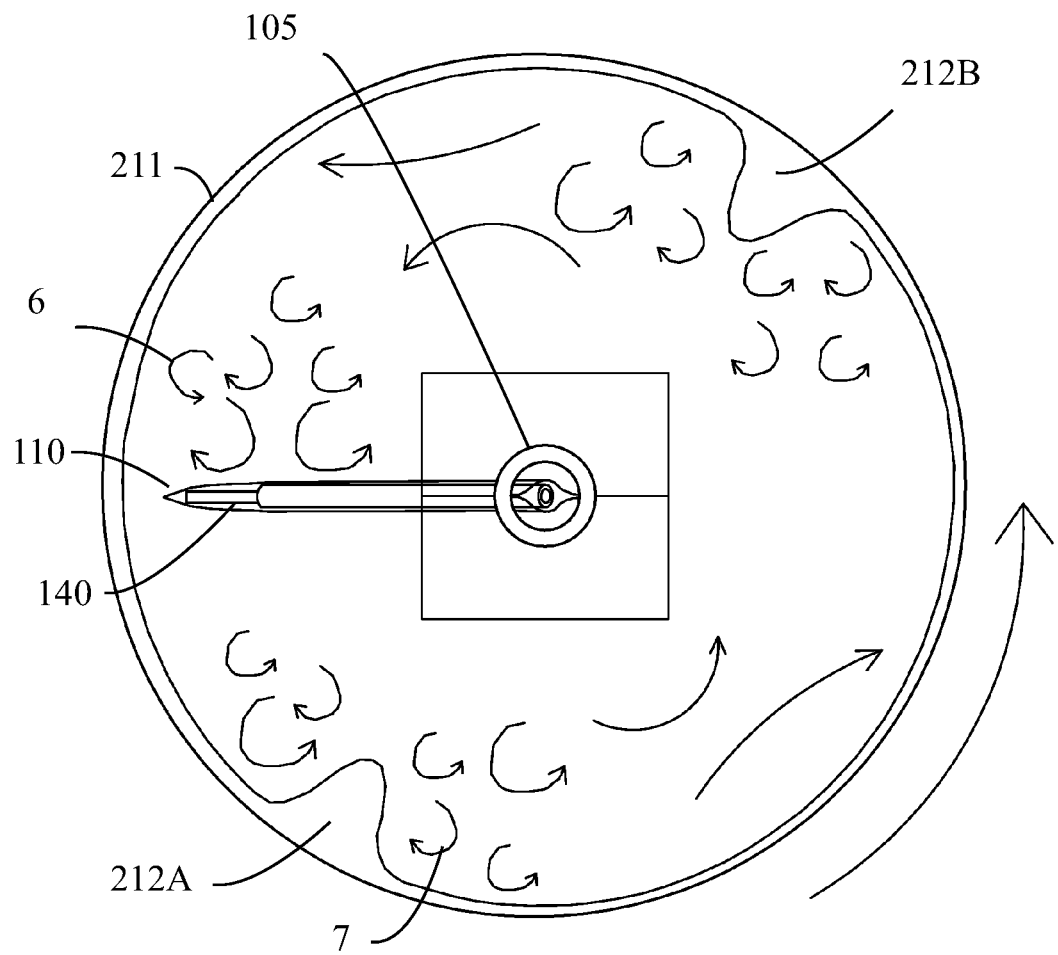
FIG._6A

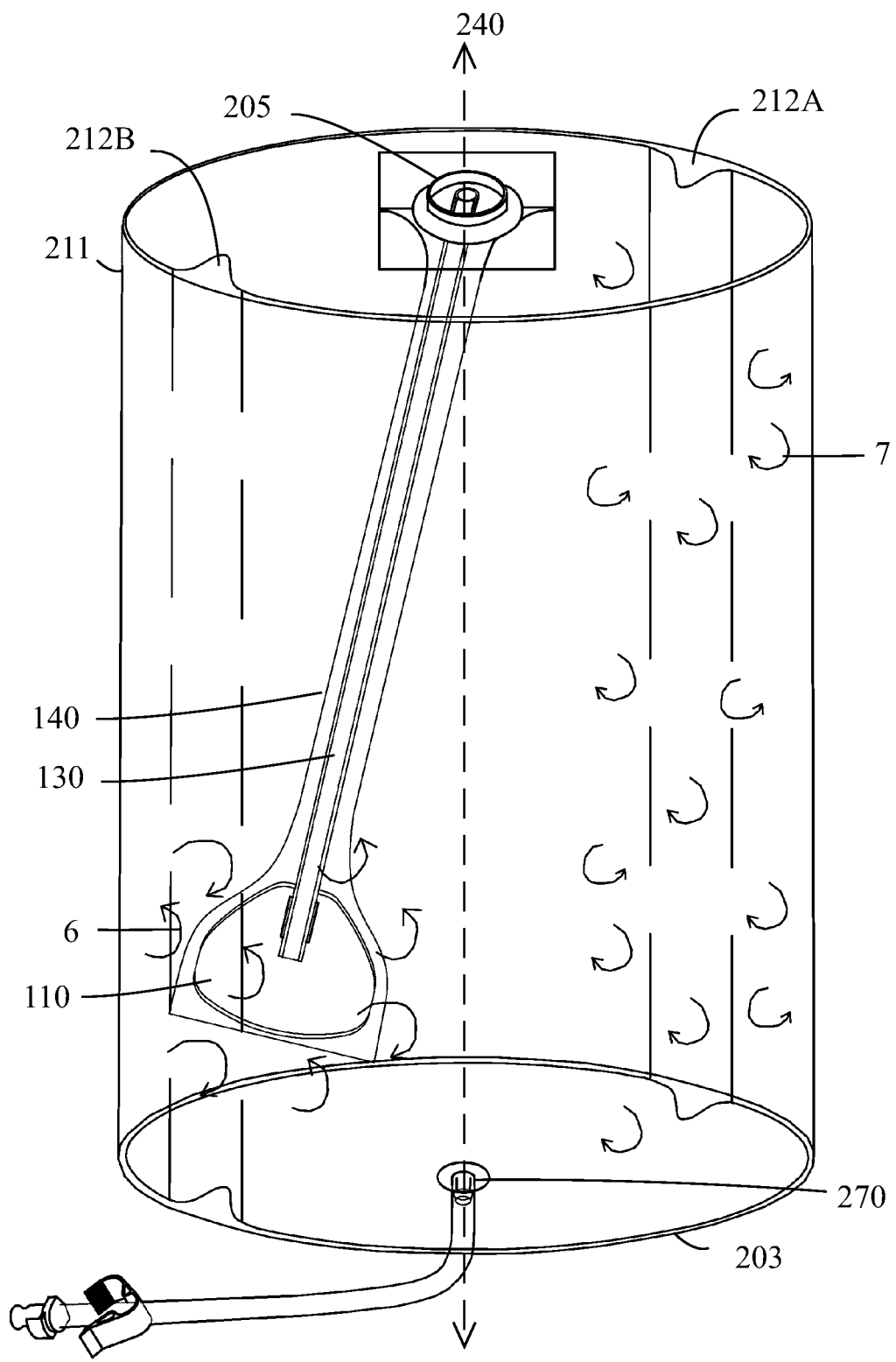
FIG._6B

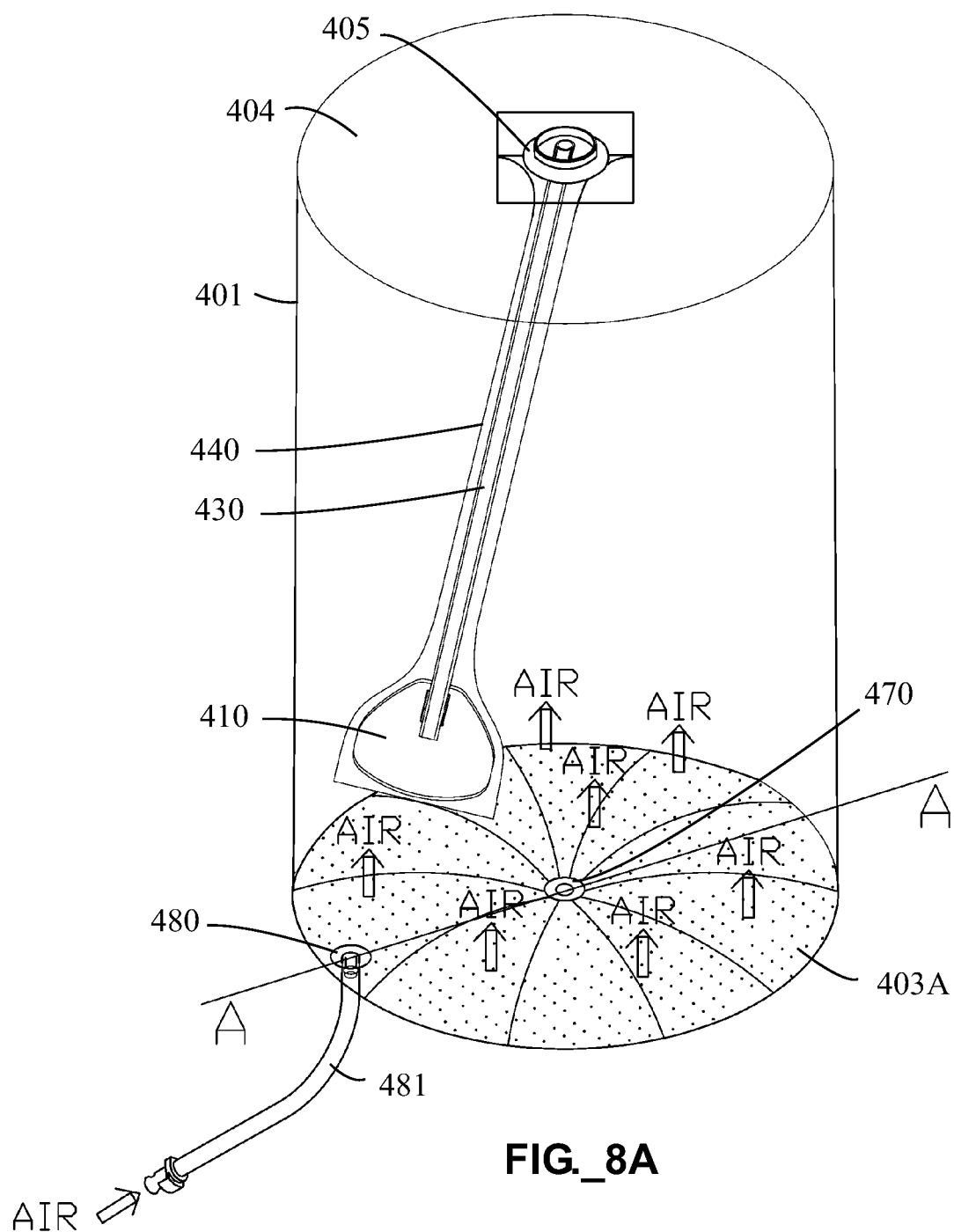
FIG._8A

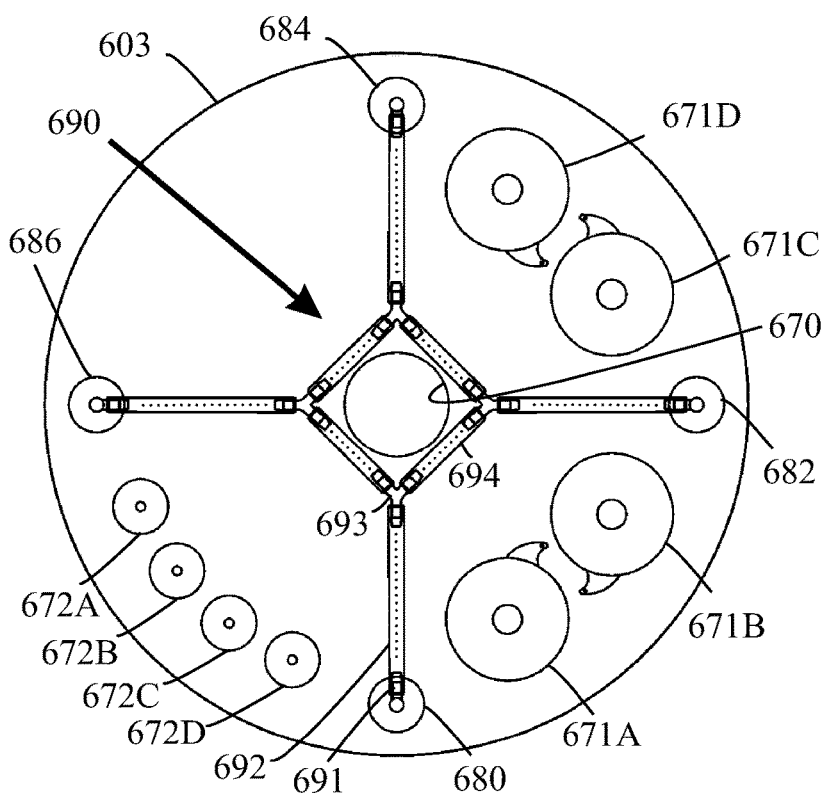
FIG._9B
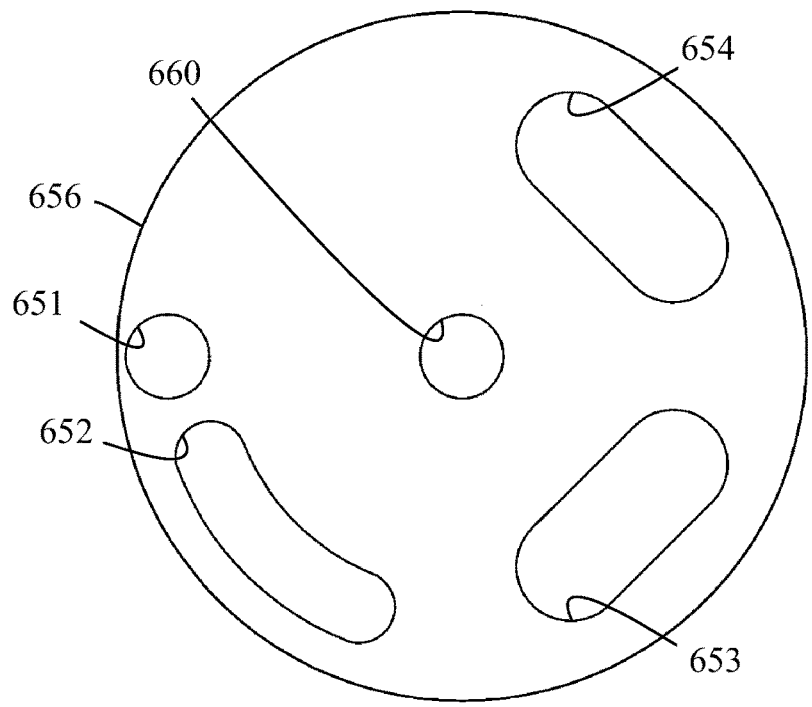
FIG._9C

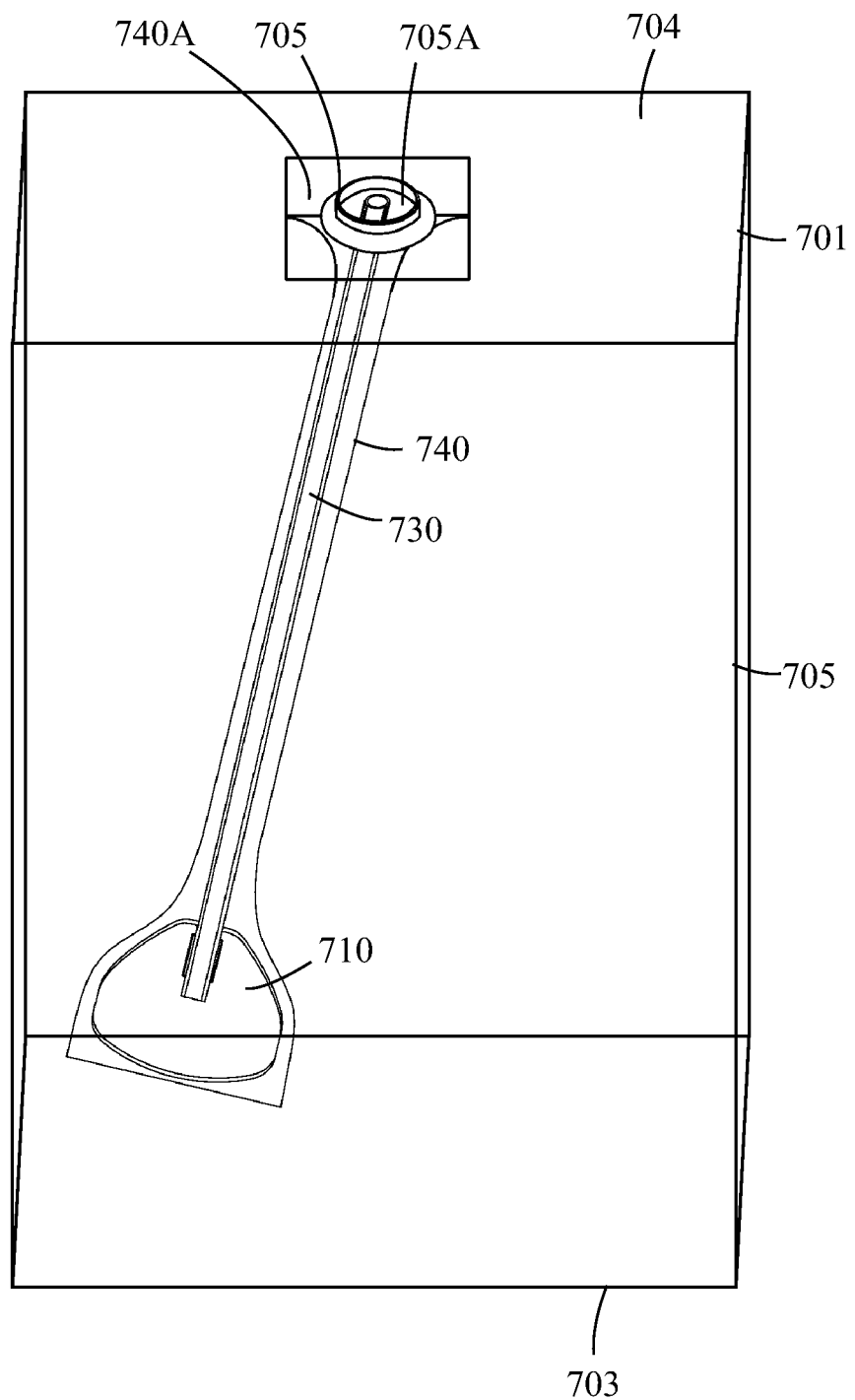
FIG._10

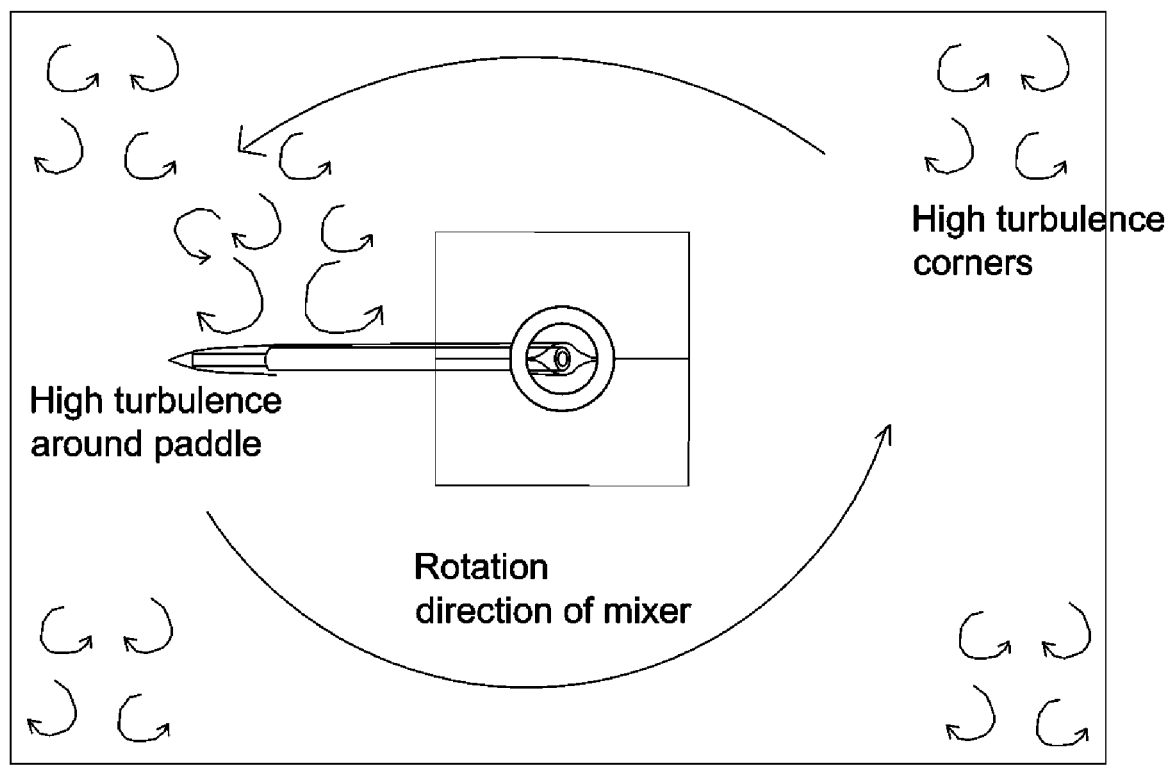
FIG._11

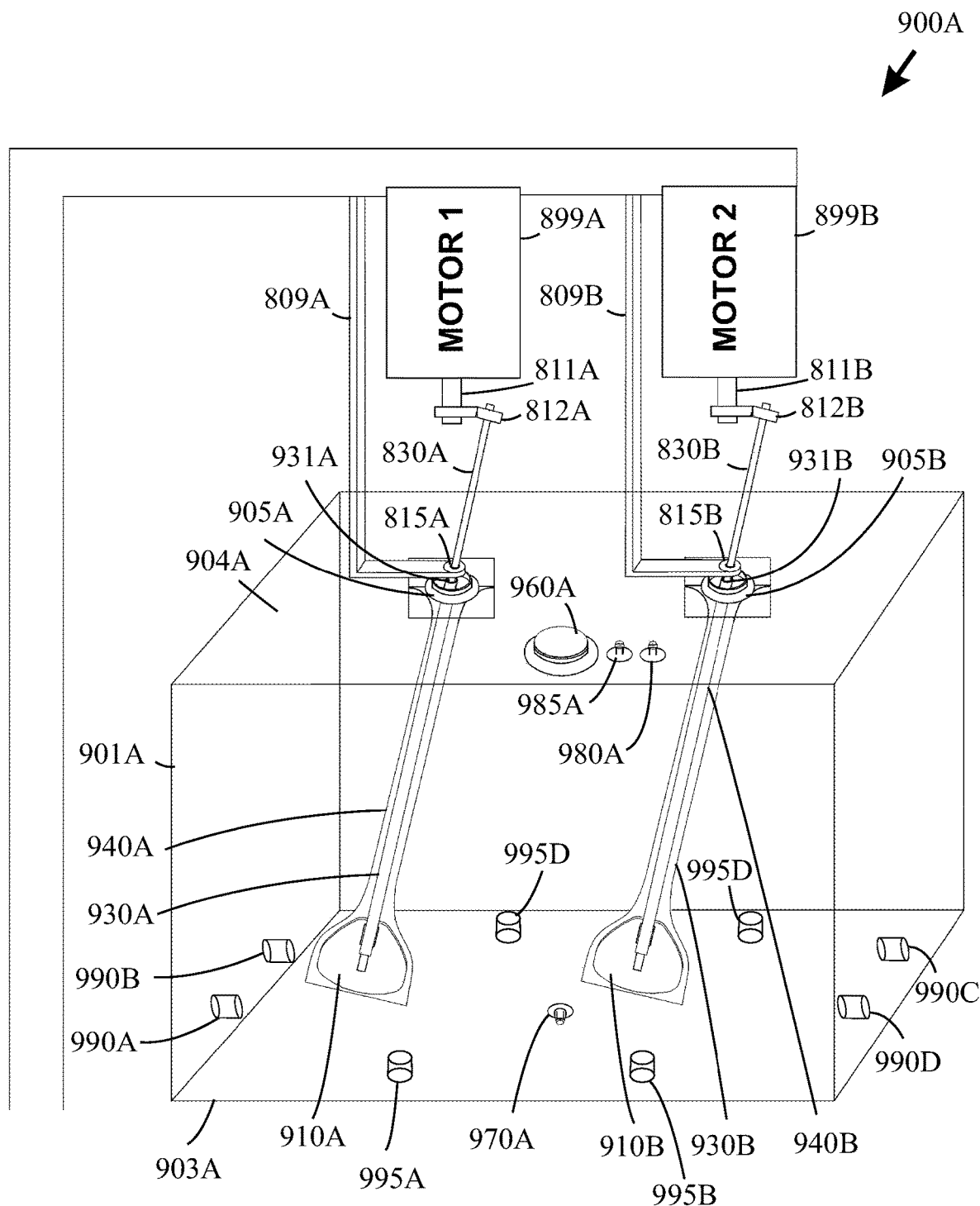
FIG._12

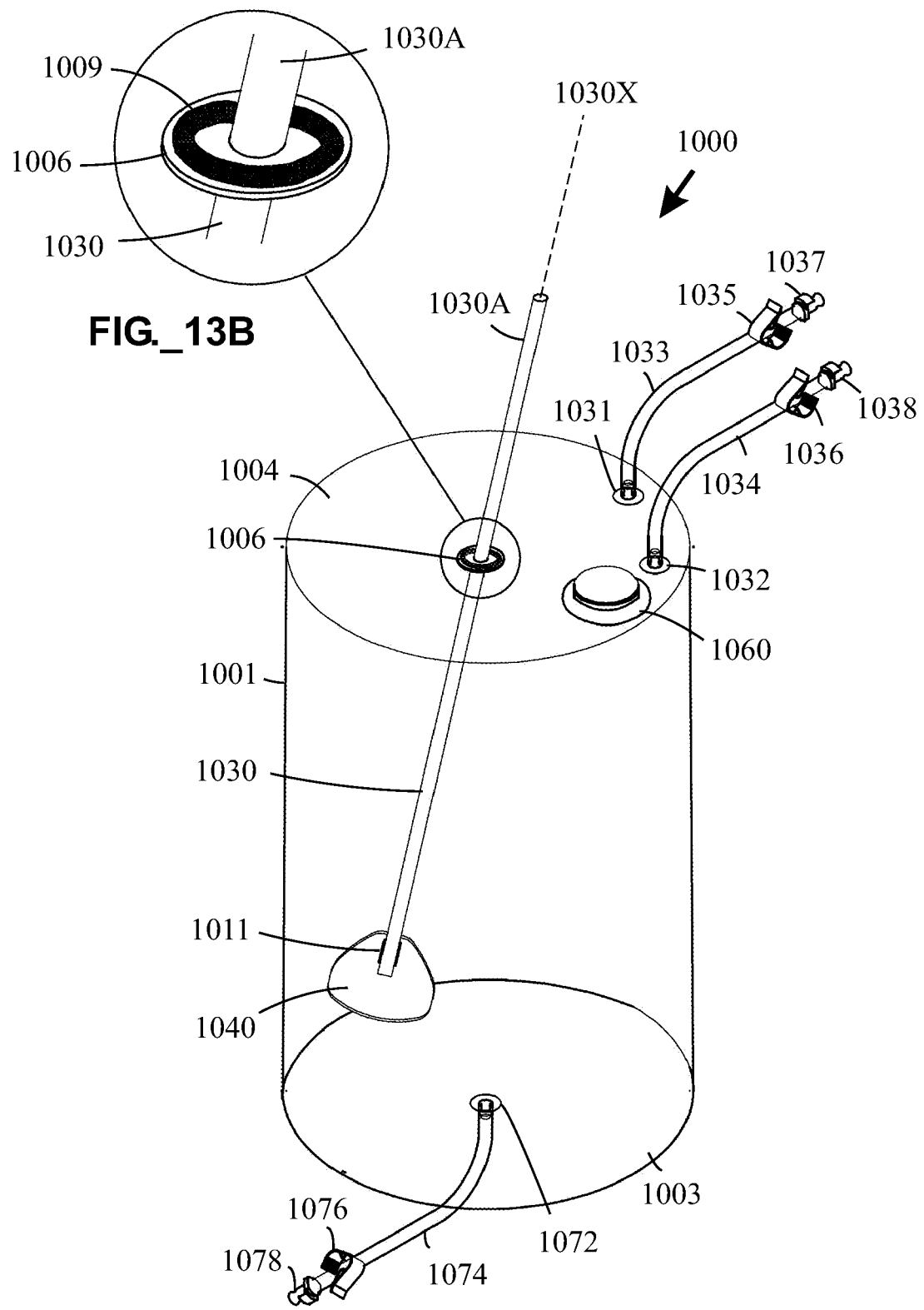
FIG._13B
FIG._13A

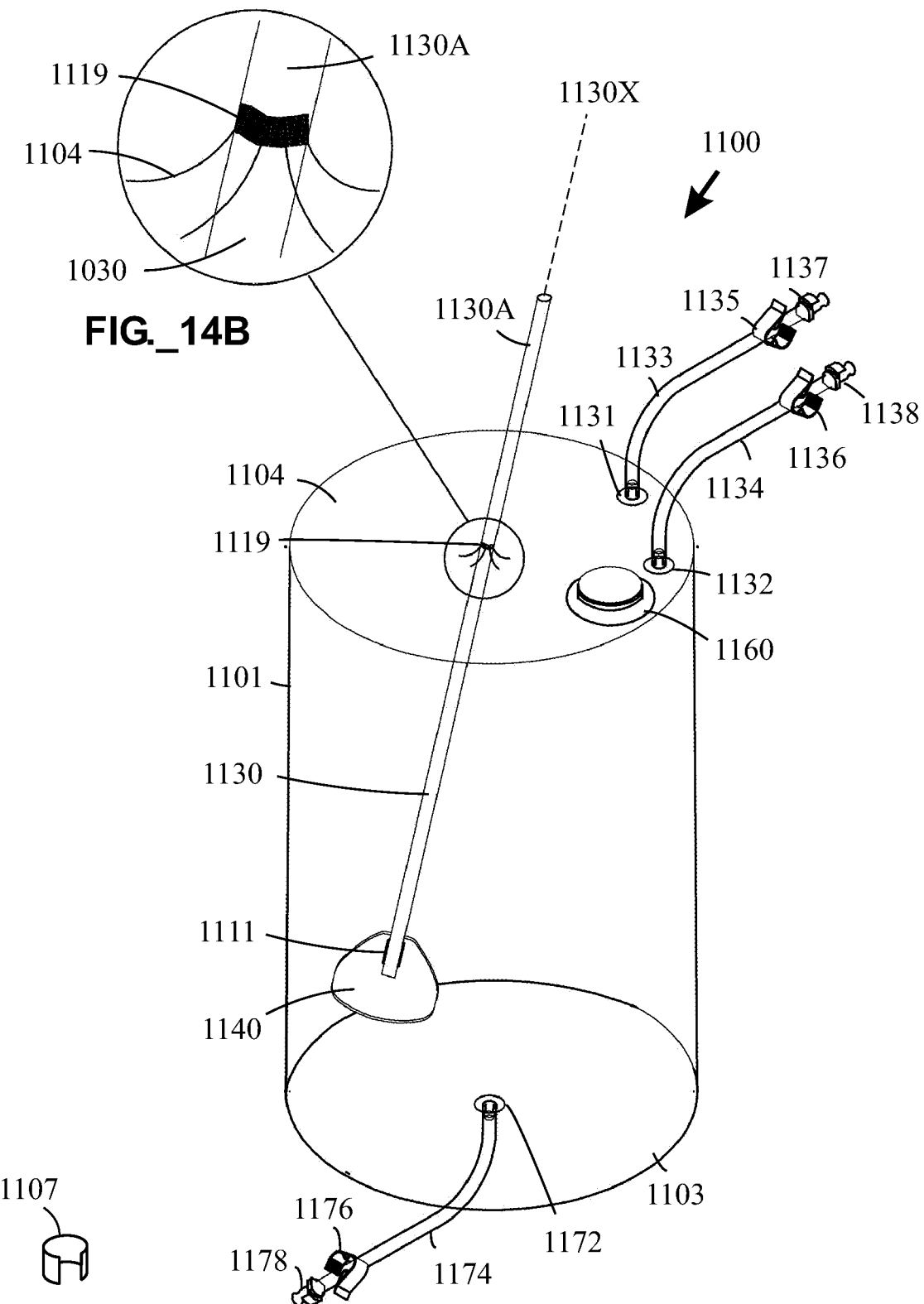

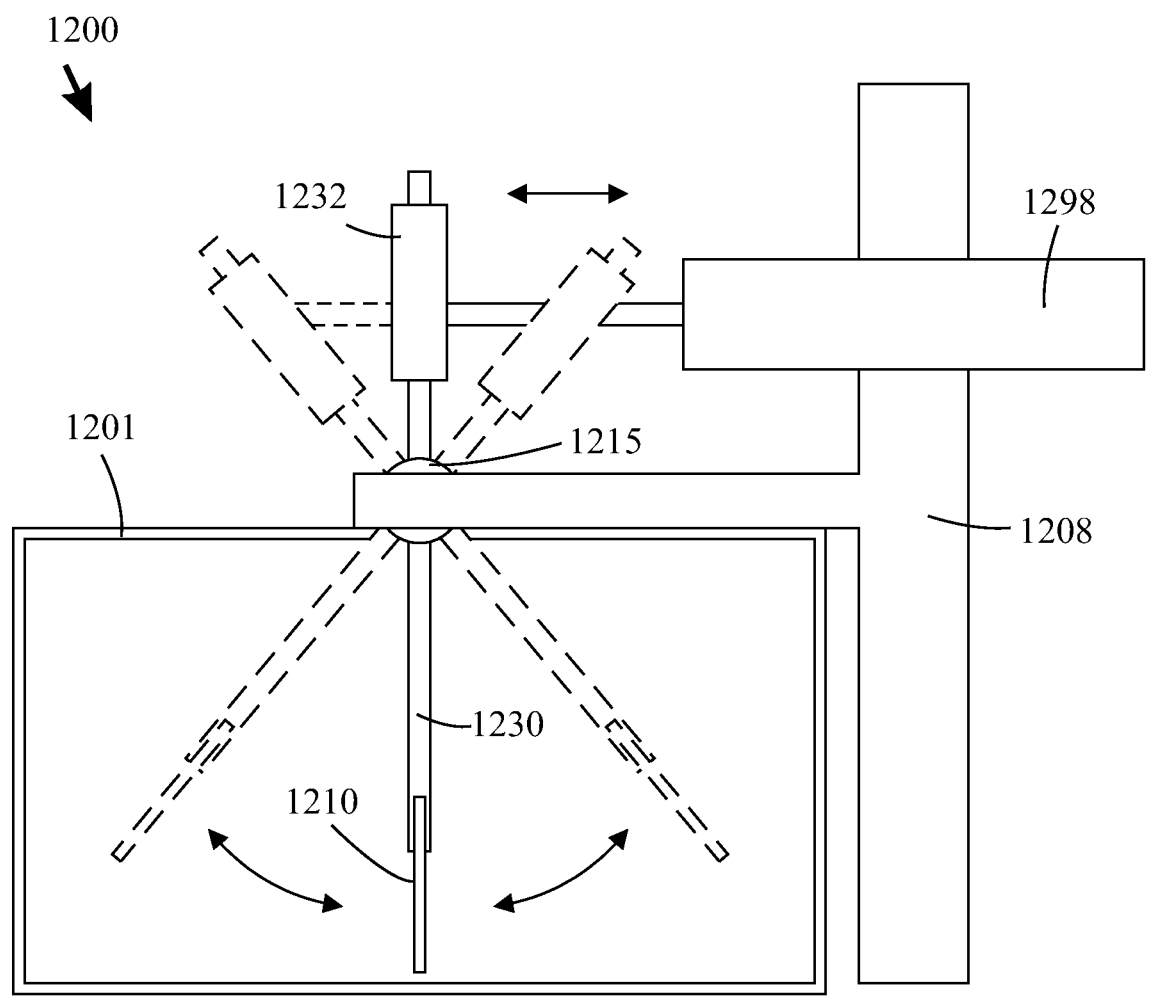
FIG._15

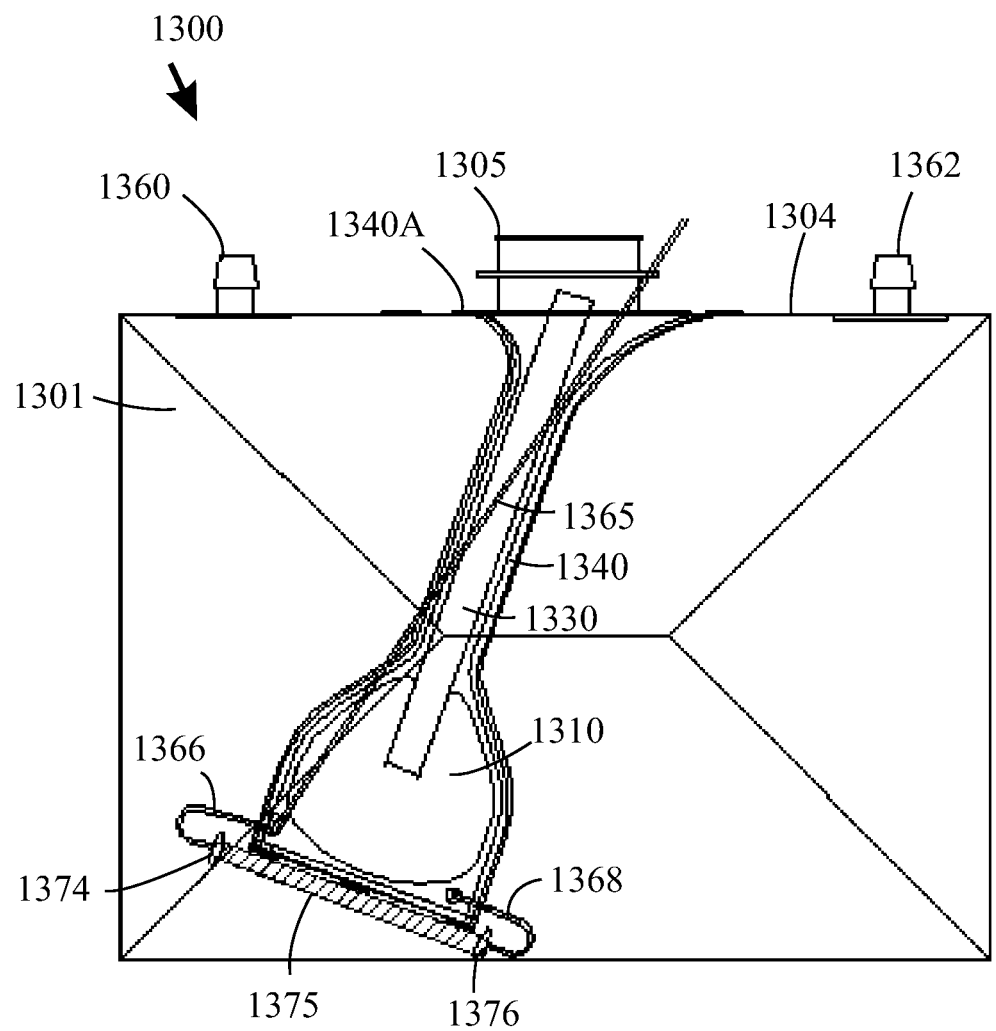
FIG._16

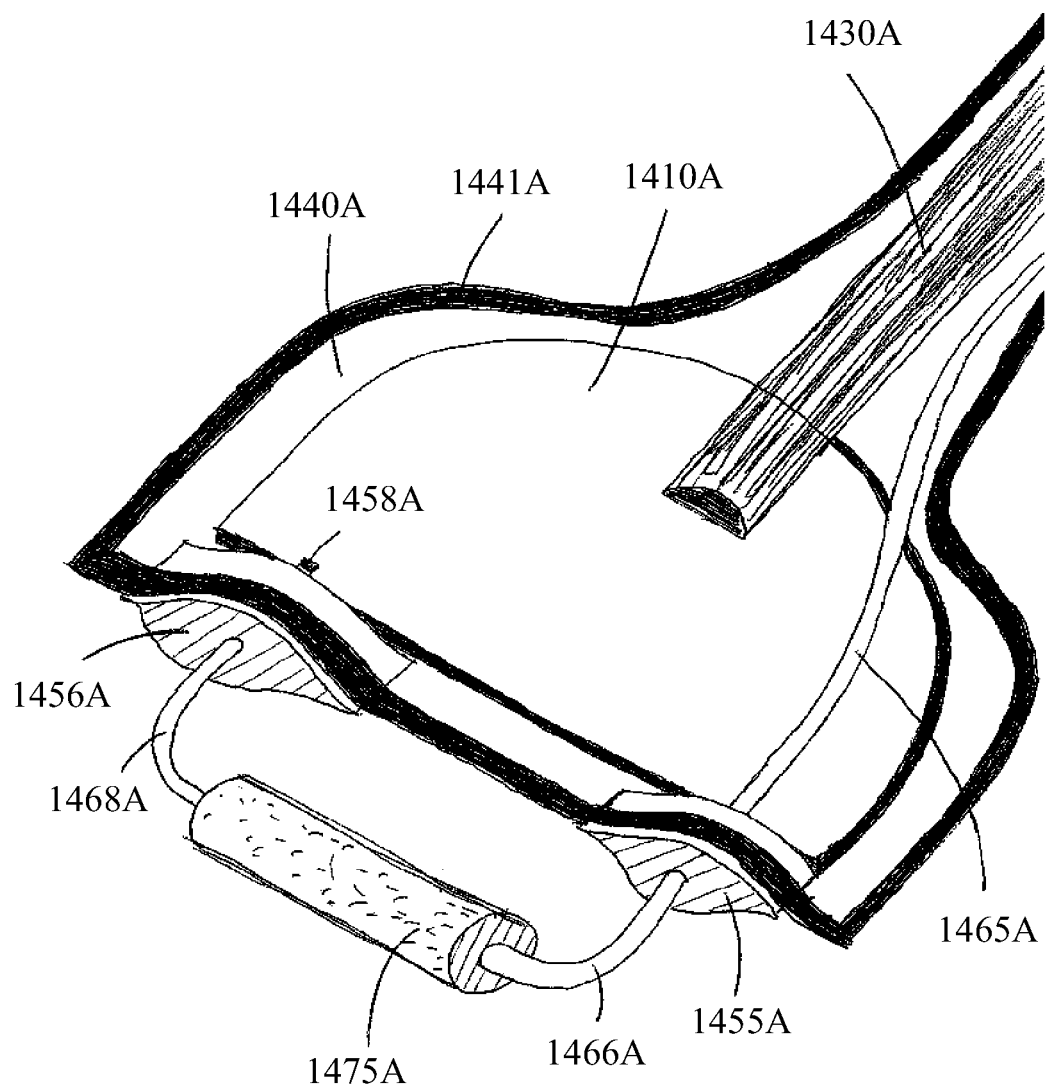
FIG._17A

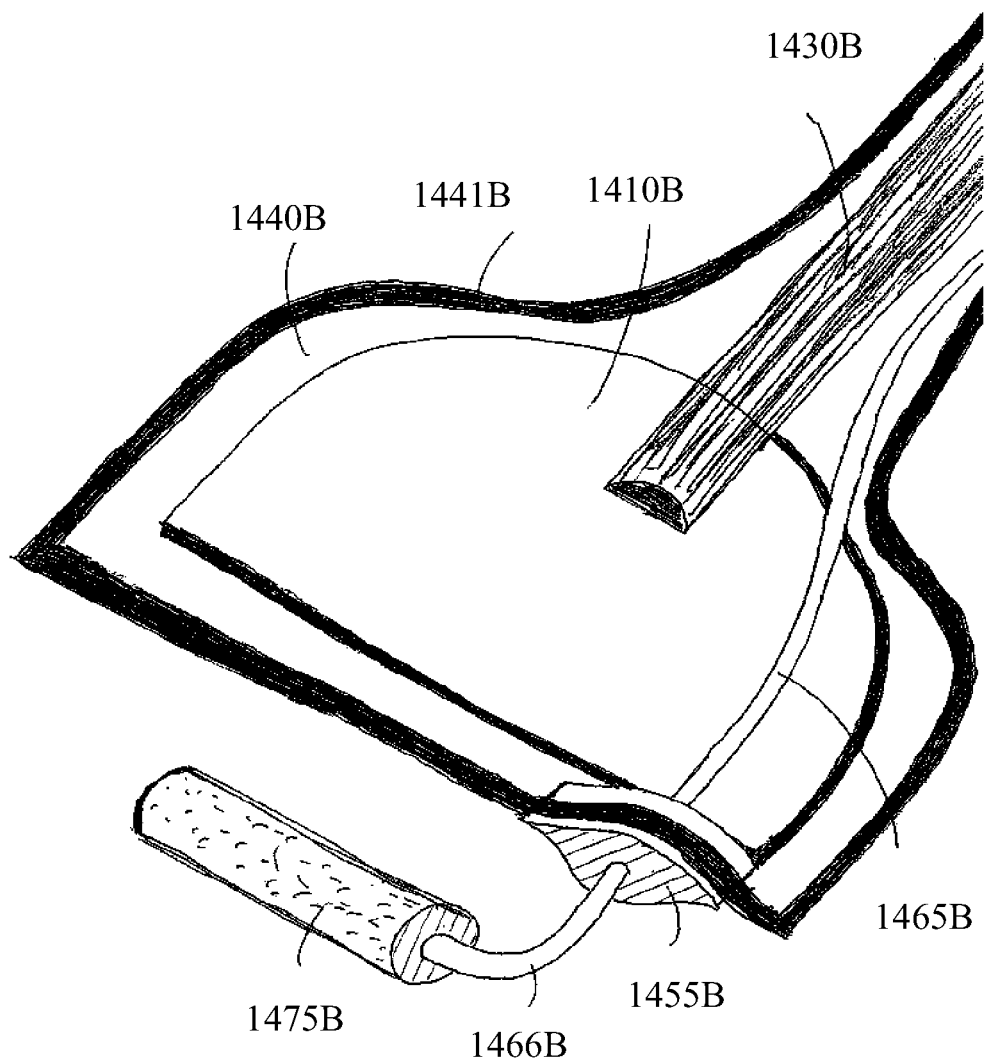
FIG._17B

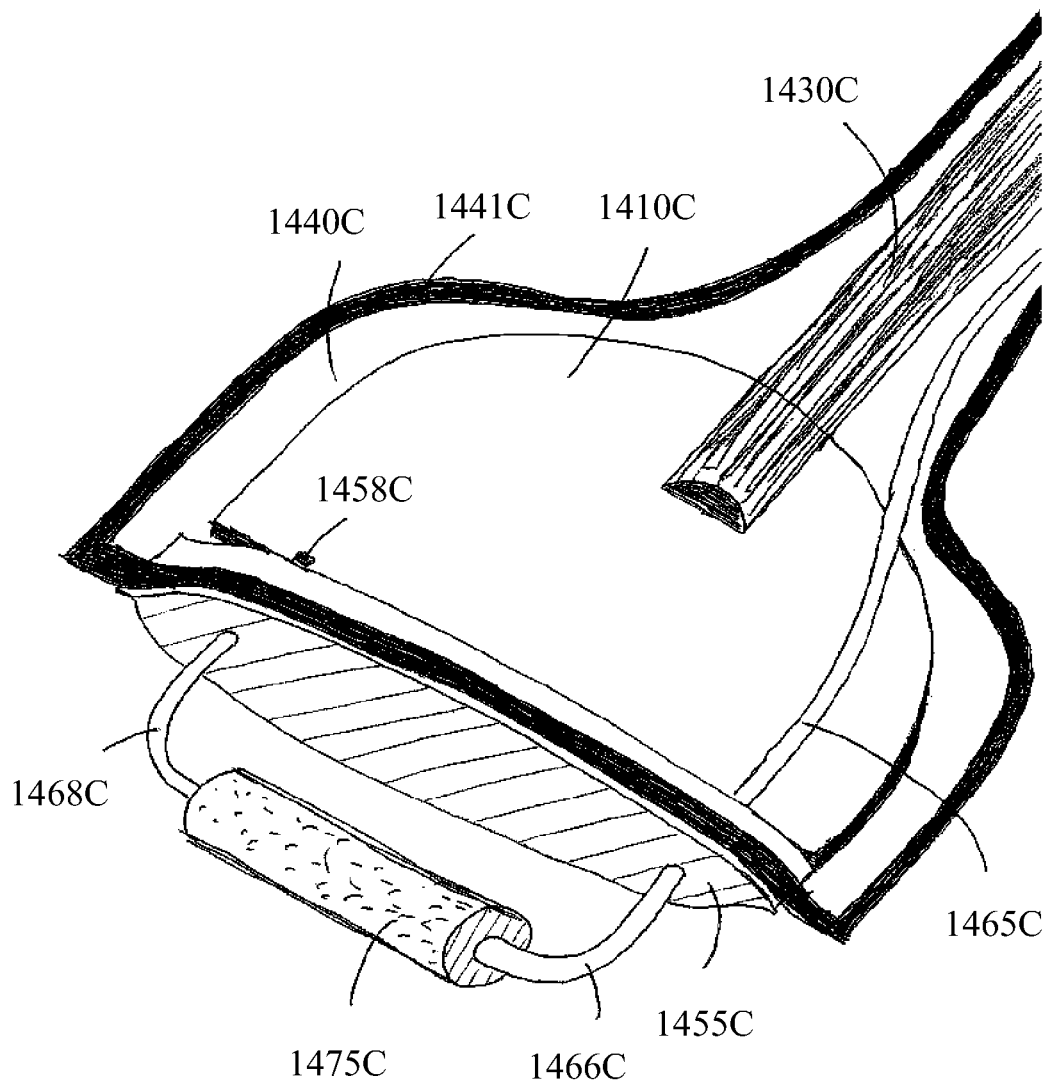
FIG._17C

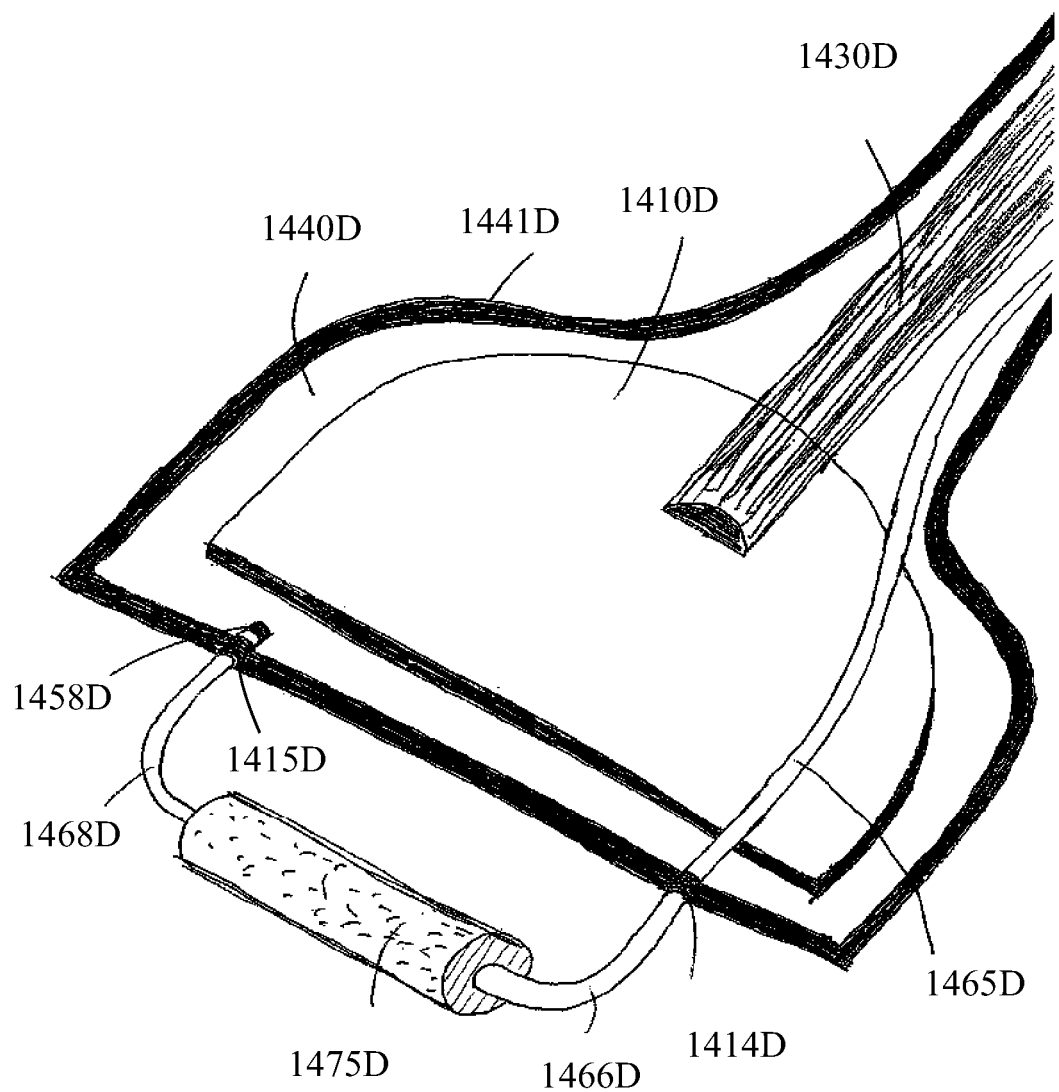
FIG._17D

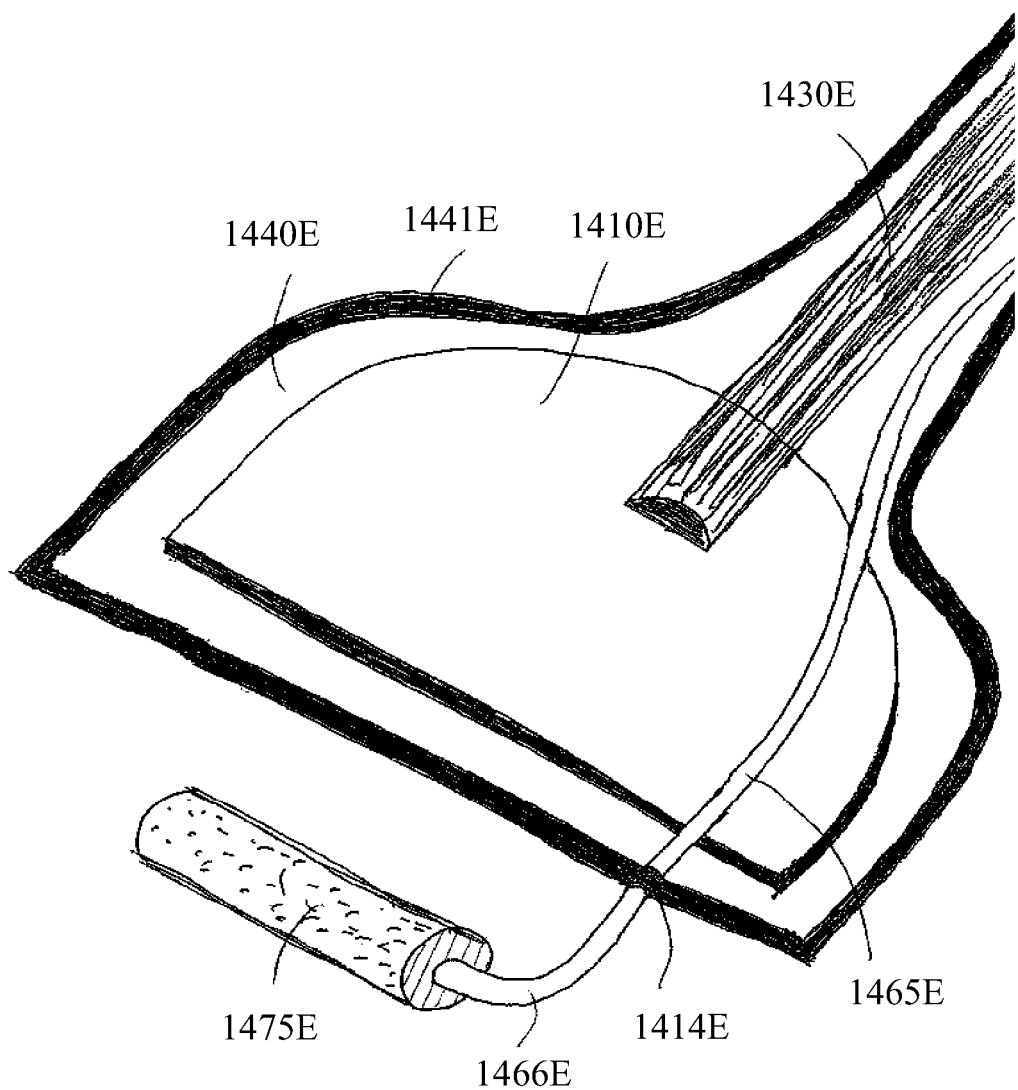
FIG._17E

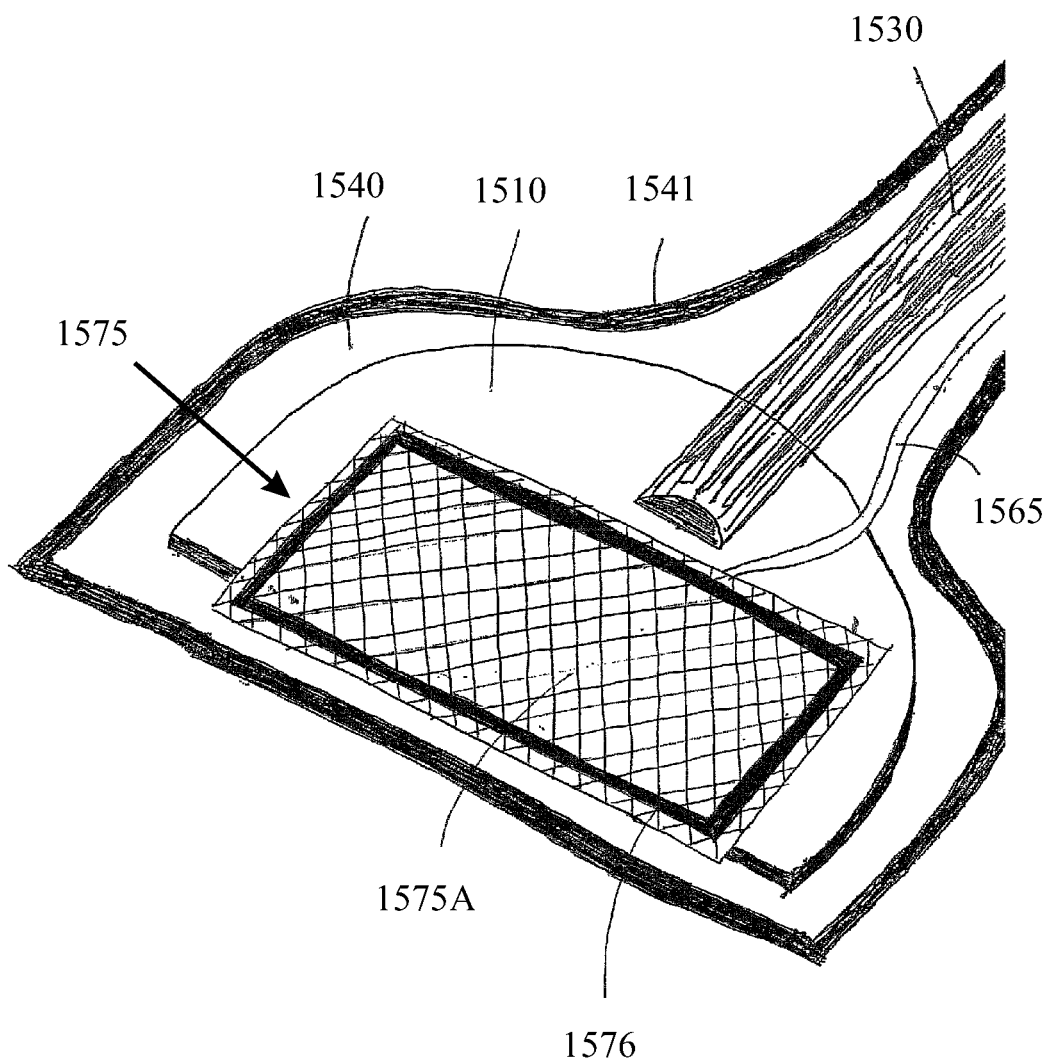
FIG._18A

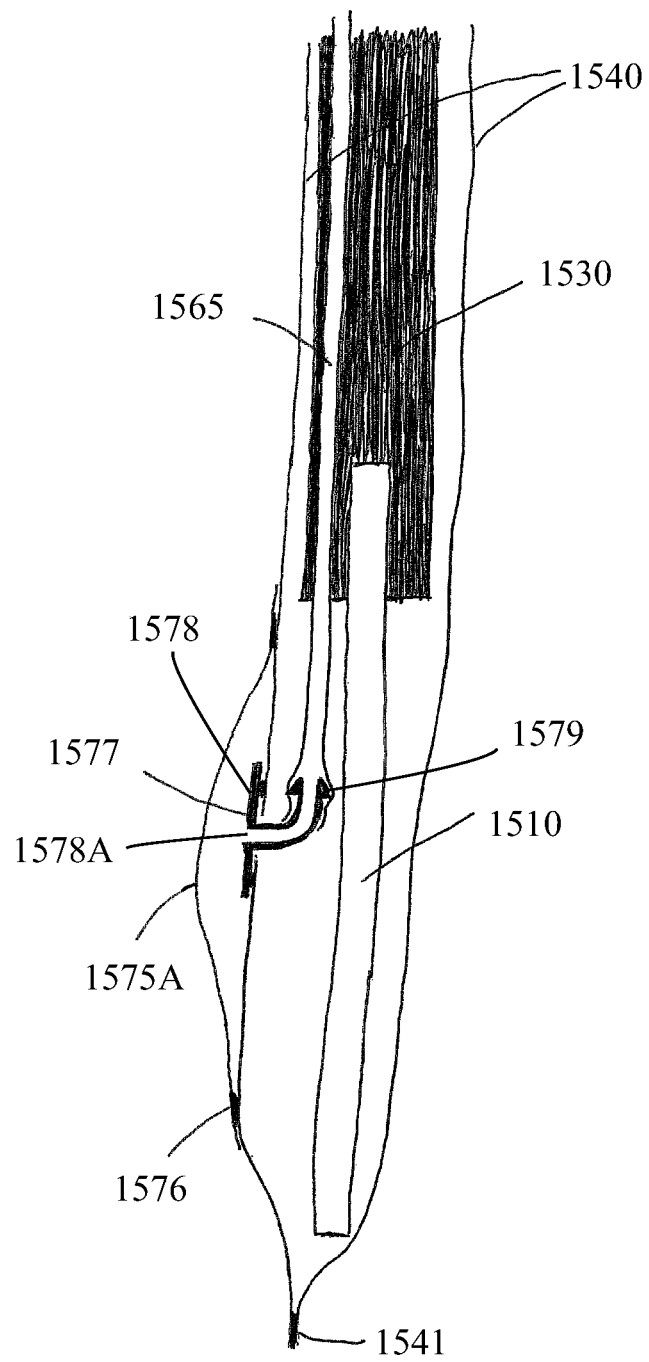
FIG._18B

FIG._20

$k_L a$ performances versus flow rate at flows suitable for cell culture

DISPOSABLE BIOREACTOR

STATEMENT OF RELATED APPLICATION(S)

This application claims priority under the provisions of 35 U.S.C. § 371 of International Patent Application No. PCT/US07/68828 filed on May 12, 2007, which in turn claims priority of U.S. Provisional Patent Application No. 60/799,842 filed on May 13, 2006. The disclosures of such international application and U.S. patent application are hereby incorporated herein by reference in their respective entireties, for all purposes.

FIELD OF THE INVENTION

This invention generally relates to industrial or laboratory mixing of various substances, such as (but not limited to) gases and liquids that may be employed in bioreactors performing cell culture or fermentation operations.

DESCRIPTION OF THE RELATED ART

The mixing of components, such as different types of solids, liquids and/or gases, has a number of applications in different industries. For example, in the pharmaceutical industry, different types of drugs are mixed together; in the medical field, body fluids (such as blood) and/or drugs are typical components that are mixed; and in the semiconductor field, wet solutions are combined with abrasives to make slurries. The food industry also incorporates mixing operations into a number of applications including rehydration. In these and other industries, the components to be mixed often require high levels of purity and/or sterility, such that expensive and time-consuming cleaning and/or sterilization operations are usually performed between batches in conventional mixing tanks to avoid contamination.

Bioprocessing applications such as cell culturing and fermentation present special challenges relative to many other mixing processes. Oxygen must be consistently supplied in solution (e.g., in water or another liquid) to cells or other micro-organisms. Oxygen is more readily dissolved in water with the aid of a mixing apparatus, but mixing should not be too aggressive to avoid damage to cells or microorganisms contained in the bioprocessor. Economy would be promoted by processing with large batches, but oxygen dissolution (along with mixing in general) is less efficiently performed in large liquid volumes. Ensuring relatively even distribution of oxygen among the contents of a large volume can be challenging. Bioprocessing operations can require extremely long periods—such as on the order of a few days for fermentation, and up to 30 days or more for cell culture operations. In most instances, it is desirable to maintain oxygen levels as economically as possible—with low energy consumption, and by the use of air rather than pure oxygen.

Of the preceding criteria, the most important aspect of a bioreactor is the ability to transfer oxygen into solution (e.g., in water), to ensure a consistent oxygen supply and compensate for oxygen consumption of growing cells or microorganisms. This may be expressed with the oxygen transfer rate $M_{O2}$, in units of kilograms/hour utilizing the following formula:

$$M_{O2} = K_{la} * V * (C^*_{O2} - C_{O2})$$

Where:
$V$ = volume of the liquid (l)
$C^*_{O2}$ = concentration of $O_2$ at saturation (a function of Temperature and Product)
$C_{O2}$ = actual concentration of $O_2$ dissolved in the liquid (a function of $O_2$% in the gas)
$K_{la}$ = a constant (expressed in units of per hour) that is linked to the system (a function of mixing speed, tank design, turbulence, and thus the total surface of gas in the liquid at a given time).

For a fixed gas flow, the value of $K_{la}$ determines whether a system is suitable for applications such as cell culture or fermentation. Cell culture generally requires a $K_{la}$ value from about 15 to about 40/hour, whereas fermentation generally requires a $K_{la}$ value of approximately 300.

To determine the $K_{la}$ value of a system, various parameters (such as water volume, air flow, temperature, drum shape, mixing speed, etc.) are fixed. Then the liquid is purged with nitrogen to let the saturation drop to zero percent. Once this zero percent oxygen state is established, the nitrogen is replaced by air (t=0). After a certain time the oxygen transfer rate will assume a linear rise approximately 95% saturation. Referring to FIG. 1, this rise starts at about T=1.5 minutes and continues until about T=2.5 minutes. The scope of this linear rise is the value of $K_{la}$ (in units of 1/hour).

Traditional bioreactors include stainless steel tanks having components for introducing air into the contents of the tank. In tanks intended for cell culture applications, air is typically introduced through a small perforated pipe (e.g., having holes of approximately 20 micrometers in diameter). Mixing with an agitator is performed gently to avoid damage to the cells. In tanks intended for fermentation applications, air can be introduced through a smaller number of openings (e.g., 3 in number) of approximately 1 millimeter in diameter positioned at the bottom (and/or along the lower sides) of the tank below high speed turbine agitators used to break air bubbles into smaller fragments, thus increasing the total gas surface to aid dissolution of air into the liquid within the tank. For liquid volumes of 100 liters, typical air flows are on the order of 2 liters per minute for cell culture and 150 liters per minute for fermentation. Increases in liquid volume have concomitantly increased air volumes.

Due to multiple advantages (such as elimination of inter-batch carryover or contamination, and elimination of inter-batch cleaning and/or sterilization operations) disposable containers are becoming increasingly useful in many industrial applications, including mixing applications. For example, a mixing apparatus employing a disposable and flexible mixing tank having a mixing paddle adapted to travel within the tank is disclosed in U.S. Patent Application Publication No. 2005/0078552, which is commonly assigned with the present application to Advanced Technology Materials, Inc. (Danbury, Conn., USA). Such publication discloses tanks of various shapes, including cylindrical tanks. One difficulty associated with attempting to use such a cylindrical tanks in bioprocessing applications is illustrated in connection with FIGS. 3A-3B. At a certain continuous rotation speed, bulk liquid within the tank 101 will exhibit a nearly laminar flow behavior, as depicted by streamlines 5. Around the area of the mixing paddle 110, proximate to the bottom 103 of the tank 101, sufficient turbulence exists (as depicted by turbulent mixing regions 6) since the speed of the paddle 110 is higher than the liquid through which it travels. But in other locations within the tank 101, mainly toward the upper sides of the tank, the liquid will be rotated at a constant speed, and with little to no turbulence. In such regions with substantially laminar streamlines 5, the mixing uniformity may be poor. In bioprocessing applications, when gas bubbles are introduced from the bottom of the tank 101 for dissolution into the liquid, the speed of achieving oxygen saturation and/or the level of peak oxygen saturation may be insufficient using the cylindrical tank 101. In the case of mixing solids (e.g., powders) into liquids, in certain circumstances (e.g., at certain speeds) the observable effect more closely resembles centrifugation rather than mixing, causing substances (e.g., powders) intended to be mixed to concentrate along the wall of the tank 101 rather than forming a uniform mixture.

Disposable bioreactor systems have recently become available from manufacturers such as Hyclone (Logan, Utah, USA), Wave Biotech (Somerset, N.J., USA), and Applikon Biotechnology (Schiedam, Netherlands). These systems, however, are intended for cell culture applications and typically have maximum $K_{la}$ values of around 20. Such systems are generally unsuitable for fermentation use. It would be desirable to provide bioreactor systems adapted for disposable use and permitting very high $K_{la}$ values to be attained.

One challenge associated with providing a disposable bioreactor vessel is providing interfaces to various types of sensors, such as may be useful to monitor temperature, carbon dioxide, pH, or other desirable parameters. Particularly in vessels involving large batch volumes and/or in applications involving rapid reactions, measurable parameters may be subject to local variation. A similar problem is encountered with respect to material extraction (e.g. for sampling) or material addition, as variations in local material composition or other properties may vary from one location to another within a vessel.

Another challenge associated with providing a disposable bioreactor vessel is providing temperature control for contents of the vessel. The problem is particularly challenging with large volume vessels adapted to process large batches. A desirable disposable vessel would permit filling, mixing, emptying, and monitoring operations while keeping the contents at, or bringing the contents to, a desired temperature, while minimizing the need for thermal control components to be cleaned and/or sterilized between batches.

Furthermore, if when it is desired to provide direct contact between a probe and the fluid contents of a disposable vessel, it may be difficult to do so while avoiding leaks or otherwise compromising the structural integrity of the vessel.

Thus, there exists a need for improved mixing and bioreactor systems to address one or more of the above-mentioned difficulties. Desirable systems would include disposable elements to avoid or minimize the need for cleaning and sterilization between batches.

BRIEF SUMMARY OF THE INVENTION

The present invention relates to various aspects of mixing systems and methods, each preferably employing a mixing tank and mixing paddle protruding into the interior of the tank.

In a first separate aspect, the invention relates to a material processing apparatus comprising:

a hollow tank having an interior bounded by at least one interior wall;

a mixing paddle disposed and adapted to travel within the interior of the tank, the paddle being adapted to engage a support rod mechanically coupleable to receive kinetic energy from a kinetic energy source;

a functional element arranged to travel with the mixing paddle within the interior of the tank, the functional element including any of:

(a) a first sparger adapted to permit the passage of gas into the interior of the tank;
(b) at least one sensor in sensory communication with the interior of the tank;
(c) a material extraction conduit in at least selective fluid communication with the interior of the tank and adapted to permit the extraction of material from the interior of the tank;
(d) a material addition conduit in at least selective fluid communication with the interior of the tank and adapted to permit the addition of a material to the interior of the tank; and
(e) a heat exchange element in thermal communication with the interior of the tank and adapted to permit the addition or removal of thermal energy from the interior.

In another aspect, the invention relates to a method of culturing living cells utilizing the foregoing apparatus, the method comprising supplying a plurality of materials to the tank; driving the mixing paddle to move within the tank; and applying the functional element to at least a portion of the materials within the tank.

In another separate aspect, the invention relates to a material processing apparatus comprising:

a hollow tank having an interior bounded by at least one interior wall;

a mixing paddle disposed and adapted to travel within the interior of the tank, the paddle being adapted to engage a support rod mechanically coupleable to receive kinetic energy from a kinetic energy source;

a functional element interface adapted for coupling with a functional element arranged to travel with the mixing paddle, wherein the functional element is in fluid communication or sensory communication with the interior.

In another aspect, the present invention relates to a method of culturing living cells utilizing the foregoing apparatus, including supplying a plurality of materials to the tank; driving the mixing paddle to move within the tank; and utilizing the functional element interface in application of a functional element to at least a portion of the materials within the tank.

In another separate aspect, the invention relates to a fluid processing apparatus comprising:

a hollow tank having at least one interior wall;

a mixing paddle disposed within the interior of the tank, the paddle being adapted to engage a support rod mechanically coupleable to receive kinetic energy from a kinetic energy source, with the apparatus being adapted to permit pivotal movement of the support rod between the kinetic energy source and the mixing tank; and a sparger connectable to a gas supply conduit and adapted to permit the passage of gas into the interior of the tank.

In another aspect, the present invention relates to a method of culturing living cells utilizing the foregoing apparatus, including supplying a plurality of materials to the tank; driving the mixing paddle to move within the tank; and supplying gas through the sparger to the interior of the tank.

In another separate aspect, the invention relates to a material processing apparatus comprising:

a hollow mixing bag comprising a flexible film material, the bag having an interior bounded by at least one interior wall and including at least one associated baffle protruding into the interior of the bag; and a mixing paddle disposed within the interior of the bag, the paddle being adapted to engage a support rod mechanically coupleable to receive kinetic energy from a kinetic energy source, with the apparatus being adapted to permit pivotal movement of the support rod between the kinetic energy source and the mixing bag.

In another aspect, any of the foregoing aspects may be combined for additional advantage.

Other aspects, features and embodiments of the invention will be more fully apparent from the ensuing disclosure and appended claims.

BRIEF DESCRIPTION OF THE DRAWINGS

Embodiments of the invention may be best understood by referring to the following description and accompanying drawings, which illustrate such embodiments. In general within the drawings, like numbers are intended to refer to like elements or structures. None of the drawings are drawn to scale unless indicated otherwise. In the drawings:

FIG. 1 provides a desirable illustrative plot of oxygen saturation (in percent) versus time (in minutes) for the transfer of oxygen into water.

FIG. 2A illustrates a perspective view of a first motor-driven mixing system including a motor mount, a pivot guide, and a mixing tank having a sealed sleeve surrounding a mixing paddle adapted to move within the tank.

FIG. 2B illustrates an expanded view of a portion of the system of FIG. 2A, showing the sealed sleeve and mixing paddle in various positions of a 360° range of motion within the tank.

FIG. 3A illustrates a top plan view of the mixing tank and mixing paddle of FIGS. 2A-2B in operation, depicting a substantially laminar streamline along the inner circumferential surface of the tank in the direction of paddle travel, and depicting localized turbulent mixing regions adjacent to (e.g., behind) the mixing paddle.

FIG. 3B illustrates a perspective view of the mixing tank and mixing paddle of FIG. 3A in operation, depicting substantially laminar streamlines along the inner circumferential surface of the tank in the direction of paddle travel (illustrated by the external arrow), and depicting localized turbulent mixing regions adjacent to the mixing paddle.

FIG. 4A illustrates a cross-sectional view of a mixing tank having two relatively small baffles protruding into the interior of the tank, according to an aspect of the present invention.

FIG. 4B illustrates a cross-sectional view of a mixing tank having two relatively large baffles protruding into the interior of the tank, according to an aspect of the present invention.

FIG. 4C illustrates a cross-sectional view of a mixing tank having two sharply angled baffles protruding into the interior of the tank, according to an aspect of the present invention.

FIG. 4D illustrates a cross-sectional view of a mixing tank having two smoothly rounded baffles protruding into the interior of the tank, according to an aspect of the present invention.

FIG. 5A illustrates a perspective view of a support container having four internal baffles and an open top, according to an aspect of the present invention.

FIG. 5B illustrates a top view of the support container of FIG. 5A.

FIG. 6A illustrates a top plan view of the mixing paddle of FIGS. 2A-2B combined with the mixing tank of FIG. 4B in operation, with an external arrow depicting the direction of paddle travel, with longer internal arrows depicting bulk fluid motion, and with shorter internal arrows depicting turbulent mixing regions disposed (1) adjacent to the mixing paddle and (2) adjacent to the baffles.

FIG. 6B illustrates a perspective view of the mixing paddle and mixing tank of FIG. 6A in operation, with internal arrows depicting turbulent mixing regions disposed (1) adjacent to (e.g., behind) the mixing paddle and (2) adjacent to the baffles.

FIG. 8A illustrates a perspective view of a mixing tank having a mixing paddle and a double bottom with a perforated first layer disposed over a second layer of impermeable material, with arrows indicating the direction of air passage into the interior of the tank, according to an aspect of the present invention.

FIG. 9B is a top view of the bottom wall and air distribution manifold portions of a mixing tank similar to the tank depicted in FIG. 9A.

FIG. 9C is a top view of the bottom wall of a support container (such as the container depicted in FIGS. 5A-5B) adapted for use with the mixing tank portions of FIG. 9B.

FIG. 10 is a perspective view of a mixing apparatus including a parallelepiped-shaped mixing tank, an integral sleeve containing a mixing paddle and support rod, and a coupling guide permitting pivotal movement of the mixing paddle within the interior of the tank, according to an aspect of the present invention.

FIG. 11 illustrates a top plan view of a parallelepiped-shaped mixing tank having a mixing paddle (such as the tank and paddle illustrated in FIG. 10) in operation, with long curved arrows depicting the direction of paddle travel and of bulk fluid motion, with longer internal arrows depicting bulk fluid motion, and with shorter internal arrows depicting turbulent mixing regions disposed (1) adjacent to the mixing paddle and (2) adjacent to the corners.

FIG. 12 is a perspective view of a mixing system including a motor mount and two motors adapted to drive two mixing paddles, disposed in integral sleeves, in a pivotal manner within the interior of a single parallelepiped-shaped tank, with the mixing tank having side- and bottom-mounted fixed spargers, according to an aspect of the present invention.

FIG. 13A illustrates a perspective view of a mixing device including a cylindrical mixing tank having a sleeveless mixing element including an interior paddle and a protruding shaft sealingly engaged to the tank via a reinforcing flange, useable in a mixing apparatus according to an aspect of the present invention.

FIG. 13B illustrates an expanded perspective view of a portion of the device of FIG. 13A, showing the joint between the sleeveless shaft and the tank including the reinforcing flange.

FIG. 14A illustrates a perspective view of another mixing device including a cylindrical mixing tank having a sleeveless mixing element including an interior paddle and a protruding shaft mating to the tank with a gathered portion of the tank material, useable in a mixing apparatus according to an aspect of the present invention.

FIG. 14B illustrates an expanded perspective view of a portion of the device of FIG. 14A, showing the joint between the sleeveless shaft and the tank.

FIG. 14C illustrates a perspective view of an optional clamp for use with the mixing device of FIG. 14A.

FIG. 15 is a side schematic view of a mixing system according to an aspect of the present invention, including a parallelepiped-shaped mixing tank having a mixing paddle disposed therein, with the system adapted to translate the paddle in a substantially linear fashion along at least one dimension within the tank using a kinetic energy source adapted to generate for linear movement.

FIG. 16 illustrates a perspective view of a mixing apparatus according to an aspect of the present invention, including a parallelepiped-shaped mixing tank having an integral sleeve with a mixing paddle disposed therein, with a sparger arranged to travel with the paddle and supply gas to the interior of the tank.

FIG. 17A illustrates a perspective view of a portion of a material processing apparatus according to an aspect of the present invention, including a paddle-containing sleeve and a sparger element supported by two conduit segments and two fitments affixed to the sleeve.

FIG. 17B illustrates a perspective view of a portion of a material processing apparatus according to an aspect of the present invention, including a paddle-containing sleeve and a sparger element supported by a single segment and single fitment affixed to the sleeve.

FIG. 17C illustrates a perspective view of a portion of a material processing apparatus according to an aspect of the present invention, including a paddle-containing sleeve and a sparger element supported by two conduit segments and a single fitment affixed to the sleeve.

FIG. 17D illustrates a perspective view of a portion of a material processing apparatus according to an aspect of the present invention, including a paddle-containing sleeve and a sparger element supported by two conduit segments passing through a seam formed along an end of the sleeve without any interposing fitment.

FIG. 17E illustrates a perspective view of a portion of a material processing apparatus according to an aspect of the present invention, including a paddle-containing sleeve and a sparger element supported by a single conduit segment joined to the sleeve along a seam thereof without any interposing fitment.

FIG. 18A illustrates a perspective view of a portion of a material processing apparatus according to an aspect of the present invention, including a paddle-containing sleeve having an integrated sparger, with a portion of an outer surface of the sleeve comprising a microporous material in fluid communication with a gas supply conduit disposed within the sleeve.

FIG. 18B illustrates is a side cross-sectional view of the paddle-containing sleeve portion of FIG. 18A.

DETAILED DESCRIPTION OF THE INVENTION, AND PREFERRED EMBODIMENTS THEREOF

Figure 7A:
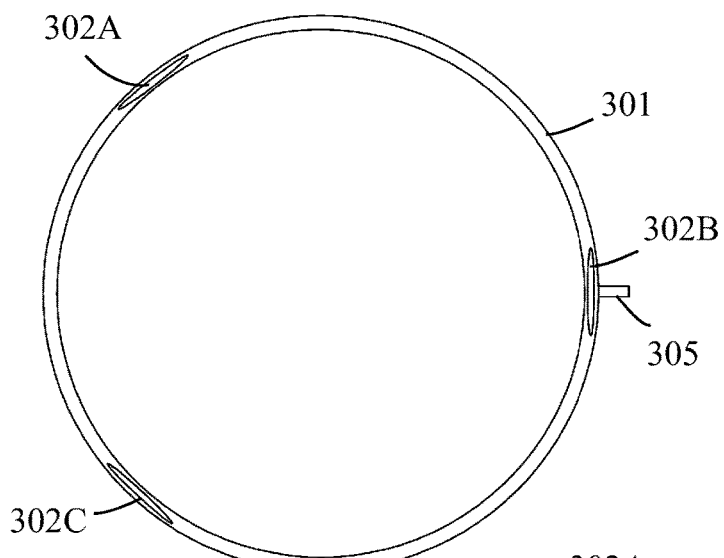
FIG. 7A illustrates a cross-sectional view of a mixing tank having three inflatable baffles, with the baffles in a first, uninflated state, according to an aspect of the present invention.

The following patent disclosures applications are hereby incorporated by reference in the present application as if set forth herein: International Patent Application No. PCT/U.S.07/67163 filed on Apr. 21, 2007 and entitled "SYSTEMS AND DEVICES FOR MIXING SUBSTANCES AND METHODS OF MAKING SAME;" U.S. Patent Application Publication No. 2005/0078552 entitled "FLEXIBLE MIXING BAG FOR MIXING SOLIDS, LIQUIDS AND GASES;" and U.S. Patent Application Publication No. 2004/0233779 entitled "FLEXIBLE MIXING BAG FOR MIXING SOLIDS, LIQUIDS AND GASES;" all of which are commonly assigned to the assignee of the present application.

The present invention encompasses apparatuses for mixing and/or reacting substances having the potential to reduce labor, lower production costs, and improve product quality in bioreactor and fermenter applications. Certain embodiments permit a flexible and disposable material processing tank, which may be embodied as bag constructed of polymeric film, to replace permanent mixing tanks for use in various applications, thus eliminating cleaning, sterilization, and product contamination concerns. The resulting apparatus may comprise a disposable bioreactor or fermenter.

Various embodiments of the present invention utilize a mixing paddle disposed and adapted to travel within the interior of the tank, the paddle being adapted to engage a support rod mechanically coupleable to receive kinetic energy from a kinetic energy source, preferably including a motor, but alternatively possibly including one or more servos, pistons, solenoids, linear or rotary actuators, or the like. A paddle preferably includes at least one widened portion that is wider than a nominal diameter or cross-sectional width of an associated support rod. Multiple widened portions may be provided with a single paddle. A paddle may further include a narrowed portion, and/or a support rod may be integrally formed with or joined to a paddle. If a sleeve is provided around the mixing paddle, such sleeve may conform closely to the size and shape of the paddle, such that the sleeve is substantially form-fitting around the paddle. The apparatus is preferably adapted to permit pivotal movement of the support rod between the kinetic energy source and the mixing tank.

In one embodiment, a mixing or material processing apparatus is adapted to permit the paddle to travel within the tank through a closed curvilinear path without continuous rotation of the paddle about a longitudinal axis of the support rod. In such an embodiment, the paddle and support rod preferably sweep a substantially conical path within the interior of the tank, with the position of the rod and paddle being at a nonzero angle relative to a central (e.g., vertical) axis of the tank. The curvilinear path may include circular and oval shapes. In another embodiment, the apparatus is adapted to permit the paddle to (reversibly) translate within the tank in a path that is substantially linear in one dimension (e.g., as viewed from above), again without continuous rotation of the paddle about a longitudinal axis of the support rod. Such paddle-based non-rotary mixing is gentler than the rotary (shear) mixing effected by a conventional impeller, particularly where large-diameter impellers are used (e.g., in large vessels) since the tip speed of an impeller can become quite high.

The paddle may be disposed within a flexible integral sleeve that serves as an isolation barrier between the paddle and the interior of the tank. In one embodiment, the mixing tank and sleeve are made of any suitable material having a property where upon removal of an extending force, it is capable of substantially recovering its original size and shape and/or exhibits a significant retractive force. As such, the mixing tank and sleeve may be made of any suitable type of stretchable, collapsible, pliable and/or elastic material. In a preferred embodiment, a disposable mixing tank is manufactured from a substantially or fully transparent film to allow for visual inspection of the tank's contents before and after use. In this regard, the tank may be embodied in a bag. The tank and sleeve may comprise the same materials.

A mixing tank and sleeve may be manufactured from any suitable material. Suitable materials include, e.g., films, polymers, thermoplastic polymers, homopolymers, copolymers, block copolymers, graft copolymers, random copolymers, alternating copolymers, terpolymers, metallocene polymers, nonwoven fabric, spunbonded fibers, meltblown fibers, polycellulose fibers, polyester fibers, polyurethane fibers, polyolefin fibers, polyamide fibers, cotton fibers, copolyester fibers, open cell foam, polyurethane, polyvinyl chloride, polyethylene, metals, alloys, fiberglass, glass, plastic (e.g., polyethylene (PE), polypropylene (PP), polyvinyl chloride (PVC), polyethylene terephtalate (PET), polyetheretherketone (PEEK) and polytetrafluoroethylene (PTFE) and polyfluoroalkoxy (PFA) derivates thereof), rubber, and combinations or mixtures thereof. A mixing tank may or may not be flexible in character. A sleeve, which defines a cavity for receiving at least a portion of a mixing paddle, should be flexible to permit substantially unrestricted movement of the mixing paddle disposed therein. If provided, the sleeve serves as an isolation barrier between the mixing paddle and the interior of the tank.

In one embodiment, a film material useable for a tank and/or sleeve comprises a multilayer laminate structure. A plurality of layers of different materials may be laminated together to provide a desired function. One or more gas barrier layers formed of a material such as ethylene vinyl alcohol (EVOH) may be included. Tie layers may be provided between different materials. One or more air gaps having unbonded regions may be provided in a multilayer or composite film. A preferred multilayer laminate includes a polyamide outer layer, a first tie layer, a polyethylene or polyethylene blend/copolymer layer, a second tie layer, an EVOH (gas barrier) layer, a third tie layer, another polyethylene or polyethylene blend/copolymer layer, an air gap, and then an inner contact layer comprising another polyethylene or polyethylene blend/copolymer layer. Multiple gas barrier layers may be provided. Another desirable multilayer structure includes a polyamide outer layer, a tie layer, a polyethylene or polyethylene-based layer, a tie layer, a first gas barrier (e.g., EVOH) layer, a tie layer, a second gas barrier (e.g., EVOH) layer, a tie layer, a polyethylene or polyethylene-based layer, an air gap, and another polyethylene or polyethylene-based layer along the (e.g., inner) surface intended to contact materials to be processed within the resulting tank.

A flexible tank may be disposed substantially within a support container, which may be manufactured from any suitable material. Rigid materials are preferred for at least a portion of the support container to confer structural integrity. If a support container includes an inflatable baffle, such as provided in the form of an inflatable bladder, then flexible materials are preferably used for at least an inner portion (such as an inner wall) of the support container as appropriate to permit the bladder to expand or contract as necessary. A support container may have an open top to permit easy access to the mixing mechanism and fluid connections disposed atop a mixing tank.

As used herein, the term "film" refers to a polymeric films, including for example, multilayer polymeric films and thermoplastic film made using a film extrusion and/or foaming process, such as a cast film or blown film extrusion process. For the purposes of the present invention, the term includes nonporous films as well as microporous films. Films may be vapor permeable or vapor impermeable, and function as liquid barriers and/or gas barriers under normal use conditions.

As used herein, the term "polymers" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and atactic symmetries.

References in the specification to "one embodiment", "an embodiment", "an example embodiment", etc., indicate that the embodiment described may include a particular feature, structure, or characteristic, but every embodiment need not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether or not explicitly described.

Embodiments of the invention may include features, methods or processes embodied within machine-executable instructions provided by a machine-readable medium. A machine-readable medium includes any mechanism, which provides (i.e., stores and/or transmits) information in a form accessible by a machine (e.g., a computer, a network device, a personal digital assistant, manufacturing tool, any device with a set of one or more processors, etc.). In an exemplary embodiment, a machine-readable medium includes volatile and/or non-volatile media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.).

Such instructions are utilized to cause a general or special purpose processor, programmed with the instructions, to perform methods or processes of the embodiments of the invention. Alternatively, the features or operations of embodiments of the invention are performed by specific hardware components, which contain hard-wired logic for performing the operations, or by any combination of programmed data processing components and specific hardware components. Embodiments of the invention may be implemented with or include software, data processing hardware, data processing system-implemented methods, and various processing operations, further described herein.

Preferred mixing or material processing tanks comprise flexible materials, such as to permit the tank to conform to the inner surface of an external support container. The tank may be manufactured from pyrogen free, sterile materials, to reduce risks associated with cross contamination. The flexible tank may comprise one or more ports for filling, spiking, aerating, adding and/or draining components to reduce the amount of human contact with the various components (which may be hazardous, dangerous and/or infectious) that are to be mixed as part of and during the mixing of such components.

Referring to FIGS. 2A-2B, a detailed implementation of a mixing system 100 including a mixing tank 101 is shown. While illustrated as generally cylindrical in shape, the shape of the mixing tank 101 is not so limited, as tanks of various shapes (e.g., parallelepiped) may be provided. The mixing tank 10 has a top wall 104 defining a substance inlet 160 and access ports 180, 185, and has a bottom wall 103 defining an outlet or drain 170, which may alternately be used to supply gas (e.g., air or oxygen) bubbles to the tank 101. The tank 101 further includes a sealed sleeve 140 joined to the tank 101 along a reinforced coupling guide 105. The coupling guide 105 defines an aperture that permits pivotal movement of the shaft 30. The sealed sleeve 140 contains a mixing paddle 110 that is joined to a hollow shaft 130. Adjacent to the coupling guide 105 is a pivot guide 15 (e.g., having a perforated pivot ball) through which an intermediate transfer shaft 30 extends to engage (e.g., by insertion) the hollow shaft 130 disposed below. The transfer shaft 30 is linked to a radially offset coupling 12 including an upper link 12A and a lower link 12B that engage the output shaft 11 of a motor 99. Preferably, the coupling links 12A-12B includes bearings or other rotatable support means to permit the shafts 30, 140 not to rotate about their own axes despite being driven through a substantially circular path at a nonzero angle relative to a central vertical axis of the mixing tank 101 (e.g., such as vertical axis 140 illustrated in FIG. 3B). This permits the transfer of kinetic energy from the motor 99 to the paddle 110 without continuous degree rotation of the shafts 30, 140. Such movement without axial rotation of the shafts 30, 130 ensures that the sleeve 140, which is sealed (e.g., welded) to the tank 101, does not twist or tear, or bind the paddle 110. The motor 99 is supported by a support frame 8, with an extension 9 thereof further supporting the pivot guide 15. If desired, such pivot guide 15 may be eliminated in view of the dual offset links 12A, 12B. Preferably, the support frame 8 further engages the mixing tank 101 to ensure correct positioning between the motor 99, the transfer shaft 30, and the contents of the sleeve 140.

FIG. 2B shows the sealed sleeve 140 and mixing paddle 110 in various positions of a 360° range of motion within the tank 101. The mixing paddle 110 travels in a large, closed curvilinear (e.g., substantially circular) path 113 in a plane parallel to the bottom surface 103 or base of the mixing tank 101. Simultaneously, the upper end of the transfer shaft 30 travels in a small, closed curvilinear (e.g., substantially circular) path 13 in a similarly parallel plane, but disposed above the pivot guide 15. The paddle 110 accomplishes such travel without continuous rotation about a longitudinal axis of the shaft 30. Although the offset coupling 12 preferably includes a bearing to enable non-rotation of the rod 30, an anti-rotation rod 31 protruding from the shaft 30 above the pivot guide 15 is retrained between parallel guide bars 17 affirmatively prevents the rod 30 from rotating about its own longitudinal axis. The travel diameter of the paddle 110 may be modified by adjusting the width of the offset coupling 12, the lengths of the transfer shaft 30 and the hollow shaft 130, and the placement of the pivot guide 15 relative to the shafts 30, 130.

While various embodiments discussed previously herein depict a mixing paddle disposed within a sleeve, it is to be appreciated that sleeveless embodiments are within the scope of the invention. In one embodiment shown in FIGS. 13A-13B, a mixing system 1001 includes a mixing paddle 1010 and sleeveless shaft 1030 for use in a substantially sealed mixing tank 1001. The shaft 1030 is sealed to the tank 1001, whether permanently or removably. At least one wall of the tank 1001 preferably comprises a flexible material such as a polymeric film. Permanent joining between the shaft 1030 and tank 1001 may be performed by solvent welding or thermal welding (e.g., if the shaft comprises a polymeric material) along a joint 1009 or any other appropriate joining means. Removable joining between the shaft 1030 and tank 1001 may be performed, for example, using an optional clamp 1107 (such as illustrated in FIG. 14C).

A reinforcing flange 1006 is provided along the top wall 1004 of the tank 1001 to receive the shaft 1030 and permit the establishment of the joint 1009, such as with a flat circular weld joint 1009. The flange 1006, which may be injection molded with the shaft 1030, is preferably welded to the top wall 1004 as well. Following establishment of the joint 1009, an upper portion 1030A of the shaft 1030 protrudes upward from the tank 1001 to mate with an appropriate mixing mechanism to move the mixing paddle 1040 within the tank. Since the joint 1009 is rigid, it does not permit the shaft 1030 to rotate about its own axis 1030X. Instead, the shaft 1030 is permitted to move within the tank through a substantially circular path at a nonzero angle relative to a central vertical axis of the tank 1001. The paddle 1040 is preferably permanently joined (e.g., by welding) to the shaft 1030 along a joint 1011; alternatively, the paddle 1040 and shaft 1030 may be integrally formed together such as with an injection molding process. The paddle 1040 and shaft 1030 preferably permanently joined to the tank 1001 and manufactured as a single unit and pre-sterilized to that the assembly 1000 is adapted for economical single use (e.g., through the use of low-cost polymeric materials) and subsequent disposal. Alternatively, other suitable materials may be used and the assembly 1000 may be cleaned and/or sterilized between uses if desired.

In one embodiment, at least one wall of the tank 1001 comprises a polymeric film that is preferably substantially optically transmissive or transparent, and the shaft 1030 comprises a polymer adapted to be joined to the top wall 1004 by solvent and/or thermal welding. If desired, a substantially open external frame (not shown) permitting viewing of the tank may be provided to support the tank 1001 with associated hooks or connectors (not shown). The upper wall 1004 of the tank 1001 further defines a substance inlet port 1060 and additional apertures 1031, 1032 such as may also be used to admit substances or extract substances to or from the tank 1001. Each aperture or port 1031, 1032 preferably has an associated supply line 1033, 1034, sealing element 1035, 1036, and coupling element 1037, 1038. The lower wall 1003 of the tank 1001 defines an outlet aperture or port 1072 preferably having an associated drain or outlet line 1074, sealing element 1076, and coupling element 1078. In this manner, the tank 1001 may be joined to other elements of a processing system (not shown), and substances exchanged therebetween may be processed.

FIGS. 14A-14B illustrate another mixing assembly 1100 having a sleeveless shaft 1130 and mixing paddle 1140. The primary distinction between the assembly 1100 and the prior assembly 1000 illustrated in FIGS. 13A-13B is the connection between the top wall 1104 of the tank 1101 and the shaft 1130. In the present assembly 1100, the shaft 1130 is coupled directly to the top wall 1104 without an interposing reinforcing flange 1006 (as shown in FIGS. 13A-13B). The top wall 1104 preferably comprises a flexible material such as polymeric film. The top wall material may be gathered around the shaft 1130 as shown in FIGS. 14A-14B and then welded (e.g., circumferentially welded to the shaft) to form a joint 1119, or optionally clamped using a clamp 1107 as illustrated in FIG. 14C to permit removable engagement between the shaft 1130 and the tank 1101. As before, the shaft 1130 includes a protruding upper portion 1130A and an axis 1130X. Since the joint 1119 is rigid, it does not permit the shaft 1130 to rotate about its own axis 1130X. The mixing paddle 1140 is preferably permanently joined to the shaft 1130 along a joint 1111.

The upper wall 1104 of the tank 1101 further defines a substance inlet port 1160 and additional apertures 1131, 1132 such as may also be used to admit or extract substances to or from the tank 1101. Each aperture or port 1131, 1132 preferably has an associated supply line 1133, 1134, sealing element 1135, 1136, and coupling element 1137, 1138. The lower wall 1103 of the tank 1101 defines an outlet aperture or port 1172 preferably having an associated drain or outlet line 1174, sealing element 1176, and coupling element 1178.

In a variation of the foregoing sleeveless mixing assemblies 1000, 1100, a shaft may be interfaced to a tank via a rotatable sealing bearing (not shown) such as comprising a ball and socket joint. If provided, such a sealing bearing may comprise low friction polymeric materials (e.g., polytetrafluoroetylene) along mating surfaces. Multiple seals may be provided to prevent tank leakage. Preferably, however, no moving parts (such as bearings) are provided in fluid communication with the interior of the mixing tank, to avoid any possibility of leakage or contamination. In this regard, the interior of a mixing tank of a material processing apparatus according to the present invention is preferably formed with welded seams that prevent slip or rotation between elements.

Although the preceding embodiments have been directed primarily to apparatuses in which a paddle may be driven in a curvilinear (e.g., circular) path, in certain embodiments a paddle may be driven in a substantially linear manner (as viewed from above) to reversibly translate within a tank. As viewed from the side, the paddle moves back and forth along an arc. Referring to FIG. 15, a material processing apparatus 1200 includes a parallelepiped-shaped mixing tank 1201 having an internal paddle 1210 and associated support rod 1230 arranged for pivotal movement between a kinetic energy source 1298 and the interior of the tank 1201. The kinetic energy source 1298 in this case may include a piston/cylinder, solenoid, or other linear actuator. Alternatively, a motor with appropriate linear conversion mechanism may be employed. A linkage 1232 is preferably provided between the support rod 1230 and the kinetic energy source 1298. A pivot element 1215 is preferably arranged between the kinetic energy source 1298 and the tank 1201, with both the pivot element 1215 and the kinetic energy source 1298 being supported by a frame 1208. In operation, the paddle is reversibly driven in a linear manner along at least one dimension (e.g., as viewed from above) within the tank 1201. The paddle 1210, which may or may not be isolated within a sleeve (not shown), may be extremely wide relative to prior embodiments—even approaching the width of the tank—to provide enhanced mixing action.

As noted previously in connection with FIGS. 3A-3B, attempts to use the cylindrical tank 101 with the system 100 in bioprocessing applications can provide suboptimal mixing performance, leading to slow oxygen saturation or incomplete mixing.

To address such problems, one or more inwardly-protruding baffles may be formed in or otherwise associated with a tank (e.g., the tank 101) in a system otherwise as illustrated and described in connection with FIGS. 2A-2B. Such baffles preferably protrude inward toward a substantially central axis of a tank (e.g., the axis 140 illustrated in FIG. 3B). In one embodiment, referring to FIGS. 5A-5B, baffles 252A-252D may be formed in a support container 250 adapted to receive a flexible mixing tank. The support container 250 has a bottom 256, an open mouth 255, an inner surface 254A, and an outer surface 254B, and may further include casters 259 to provide mobility. While four baffles 252A-252D are shown, and preferred embodiments include between two and four baffles, fewer or additional baffles may be provided. The container 250 is preferably freestanding and fabricated at least in part of rigid materials to provide a suitable support structure for a disposable mixing tank. A flexible mixing tank (such as the tank 101 previously shown in FIG. 2A or 3B), such as fabricated of a polymeric film material, may be inserted through the mouth 255 into the support container 250, with the flexible tank preferably sized to conform to the inner surface 254A when contents to be mixed are supplied to the tank. In this manner, the baffles 252A-252D formed in the support container 250 protrude toward the interior of the flexible mixing tank. Thus, baffles may be added to (e.g., integrally formed on) the inner walls of support container to thereby form inwardly-protruding baffles in a mixing tank adapted to conform to the shape of the container, or in the alternative, baffles may be formed directly along the inner surface of a flexible tank. If desired, the support container 250 may include one or more apertures in the side wall 254B or the bottom 256 to enable various fluid lines (e.g., for supply or drainage) or sensors to be connected to the flexible tank, with corresponding apertures preferably provided in the corresponding tank.

Other baffle configurations may be provided. For example, referring to FIGS. 4A-4D, each tank (or support container) 201, 211, 221, 231 includes two baffles 202A, 202B, 212A, 212B, 222A, 222B, 232A, 232B, respectively. The size, shape, and number of baffles may be selected for the desired mixing application, and may be widely varied. For example, the baffles 202A, 202B illustrated in FIG. 4A are relatively small; the baffles 212A, 212B illustrated in FIG. 4B are relatively larger; the baffles 222A, 222B illustrated in FIG. 4C are sharply angled; and the baffles 232A, 232B illustrated in FIG. 4D are smoothly rounded. Each baffle is preferably disposed in a substantially vertical orientation along or abutting the inner periphery of the tank. Each tank or support container 201, 211, 221, 231 is preferably substantially cylindrical except for the inclusion of the baffles, although other shapes may be employed The beneficial effect of the addition of baffles to a mixing tank and mixing system is apparent in FIGS. 6A-6B. FIG.

6A illustrates a top plan view of the mixing paddle of FIGS. 2A-2B combined with the mixing tank 211 of FIG. 4B in operation, with an external arrow depicting the direction of paddle travel, with longer internal arrows depicting bulk fluid motion, with short internal arrows 6 depicting turbulent mixing regions disposed adjacent to (e.g., behind) the mixing paddle 110, and with short internal arrows 7 depicting turbulent mixing regions adjacent to the baffles 212A, 212B. With the addition of the baffles 212A, 212B to the tank 211, the motion of the mixing paddle 110 at a nonzero angle relative to the substantially central vertical axis 240 of the tank 211 yields substantially better mixing over a broader range of conditions than the tank 101 illustrated in FIG. 3B. This is particularly advantageous in bioprocessing applications where it is desired to achieve rapid oxygen saturation in a liquid such as water, and/or to maintain relatively high levels of oxygen saturation despite the presence of oxygen-consuming biological moieties.

Figure 7B:
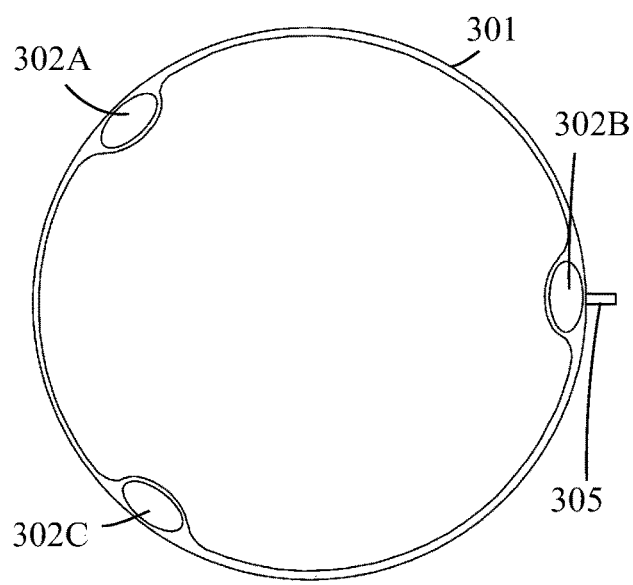
FIG. 7B illustrates a cross-sectional view of the mixing tank of FIG. 7A, with the baffles in a second, partially inflated state.
Figure 7C:
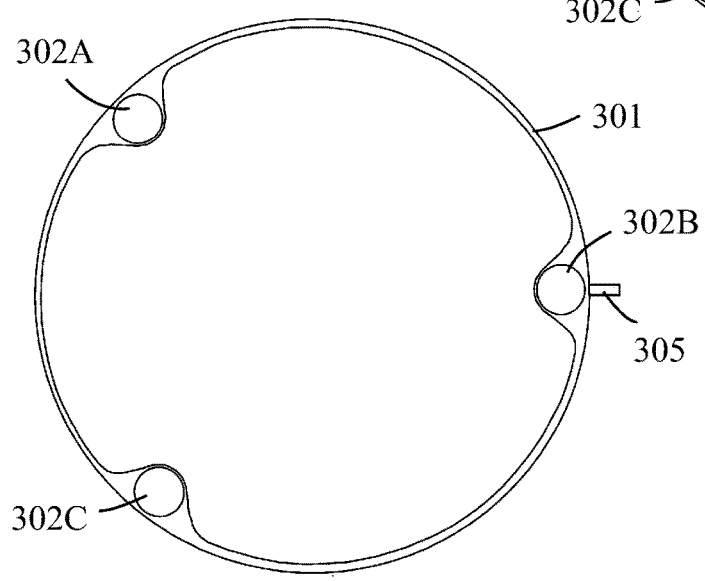
FIG. 7C illustrates a cross-sectional view of the mixing tank of FIGS. 7A-7B, with the baffles in a third, fully inflated state.

In one embodiment, either a tank or support container may include inwardly-protruding baffles that are inflatable. If provided in a support container, the container preferably has a rigid outer wall to provide structural integrity and has a flexible inner wall to permit the baffles to expand inwardly. Each baffle preferably includes an inflatable bladder in fluid communication with an external source of pressurized fluid (not shown) that permits the baffle to be expanded to the desired volume. FIGS. 7A-7C illustrate a mixing tank 301 (or support container adapted to receive a mixing tank) having three baffles 302A-302C in three states of operation. An inflation inlet 305 is provided in at least intermittent fluid communication with the baffle bladders. In FIG. 7A, the baffles are in a first, uninflated state. In FIG. 7B, the baffles are in a second, partially inflated state. In FIG. 7C, the baffles are in a third, fully inflated state. In this manner, baffles may be deployed at any appropriate time and/or to any appropriate extent in conjunction with a mixing operation to achieve a desired mixing effect.

If desired, baffle-containing tanks as provided herein may be used in conjunction with non-paddle-based mixing elements known in the art. Impellers, stirbars, and other known mixing elements may be employed in appropriate applications.

While the preceding embodiments have focused on cylindrical tanks, is to be appreciated that the invention is not so limited. Other desirable shapes, including parallelepiped (inclusive of rectangular, cubic, and other forms) shaped tanks, may be used in conjunction with mixing paddles and optional sleeves as described previously. Cylindrical tanks have been commonly used in bioprocessing applications to permit a wide operating pressure range by avoiding stress concentration regions (i.e., corners), and to provide favorable height/width ratios to promote oxygen transfer from a bottom-mounted sparger to the contents of the tank. Parallelepiped-shaped tanks may be desirably fabricated with multi-layer sheets (with preferred multi-layer laminates being described below), such as by welding sheets along edges thereof, to enable a wider operating pressure range. One or more barrier layers may be provided in such a multi-layer laminate.

One example of a parallelepiped-shaped tank equipped with a paddle and sleeve is provided in FIG. 10. The tank 701 includes a top wall 704, a bottom wall 703, and side walls 705 joined along edges thereof, preferably with welded joints. A paddle 710 having an associated support rod 730 is disposed within an integral sleeve 740 that is affixed to any of the top wall 704 and a coupling guide 705, preferably by welding. The sleeve 740 may included an enlarged upper attachment portion 740 for mating with the top wall 704. The coupling guide 705 defines an aperture 705 sized to permit pivotal movement of the support rod 730 between the interior of the tank 701 and an external kinetic energy source (not shown). The support rod 730 may be hollow to permit the insertion of a transfer shaft (not shown) linkable to an external kinetic energy source (not shown). The support rod 730 may be integral with the paddle 710. The paddle 710 and sleeve 740 are adapted to travel within the tank 701, being pivotally suspended from the top wall 704 of the tank 701. For the sake of simplicity, elements such as any inlet port, outlet port, and drain, have been omitted from FIG. 10, but it is to be understood that any utilitarian structure in this regard may be added to the apparatus.

With the use of a paddle as described previously herein, certain advantages may be achieved through the use of processing tanks having non-cylindrical (e.g., parallelepiped) shape. As illustrated in FIG. 11, high turbulence regions are generated not only around the paddle as it travels within the tank, but also along the corners of the tank. That is, a generally circular flow pattern within the middle of the tank tends to cause multi-directional flow or turbulent regions along the corners. Such high turbulence regions tend to enhance mixing. Baffles as described previously may be further added as necessary or desired to achieve a particular mixing or flow distribution pattern.

As mentioned previously, certain applications require the ability to transfer oxygen or other gases into solution. Certain embodiments include gas injection elements or spargers in fluid communication with the interior of a mixing tank, such as to the passage of air or other gases into the tank. The term "sparger" refers to an element adapted to permit one fluid (typically a gas) to be injected, and preferably distributed, into another fluid (typically a liquid).

A classical sparger includes a series of holes defined in a rigid tube. A high speed impeller is typically placed over such a sparger. Relatively large bubbles released from the sparger are cut or dispersed into smaller bubbles by the impeller. High speed impellers, however, are unsuitable for certain bioreactor or fermenter applications, as they can damage materials to be processed, and further present risk of leakage or contamination adjacent to rotatable seals. Even if an impeller is omitted in favor of using a sparger with (conventional-scale) small holes, the diameter, amount, and homogeneity of gas bubbles formed are typically not optimal for use in bioreactor or fermenter systems to provide maximum cell production and/or protein yield.

A sparger as employed in embodiments of the present invention may include a perforated or porous material, such as a perforated or porous tube, a perforated or porous film, or the like. To overcome limitations associated with classical spargers, spargers used with the present invention preferably comprise microporous or micro-perforated materials, obviating the need for use of any associated high speed impeller to generate small bubbles. Small bubbles are desirable to enhance mass transport of oxygen into solution within a material processing apparatus. A microporous or micro-perforated material useful with apparatuses according to the present invention has a plurality of gas passages or openings, with such openings having an average diameter of preferably less than or equal to 200μ, more preferably less than or equal to 100μ, still more preferably less than or equal to 50μ, and even more preferably less than or equal to 20μ. In certain applications, it may be desirable to provide such material with openings having an average diameter of less than or equal to about 10μ. Examples of porous materials useable in spargers according to embodiments of the present invention include sheets or tubes of nonwoven, spunbonded polymeric materials, sheets or tubes of sintered polymeric materials, and stretched (including dry-stretched and wet- or solvent-stretched) polymeric films. Porous materials sold under the trade names Tyvek® (E.I. du Pont de Nemours and Co., Wilmington, Del. USA) and Porex® (Porex Corp., Fairburn, Ga. USA) may be used. Preferred perforated materials are preferably formed by laser drilling (e.g., with a $CO_2$ laser), which drilling is capable of reproducibly defining openings at diameters at least as small as 10μ. Such porous or perforated material may be in sheet form, tubular form, or any other suitable shape. Such material may be hydrophobic or hydrophilic in nature, and selected for such property depending on the desired application. While various polymeric materials may be used, polyethylene is particularly desirable for its inert character.

Spargers comprising microporous or microperforated materials may be placed in various locations within a fluid processing tank. In addition to the use of microporous or microperforated materials, other means for injecting gas into a liquid may be employed in certain embodiments. Gas injection elements may be disposed along the bottom of a mixing tank, along the sides of a mixing tank, along a mixing paddle, or from various combinations of such locations.

Figure 8B:
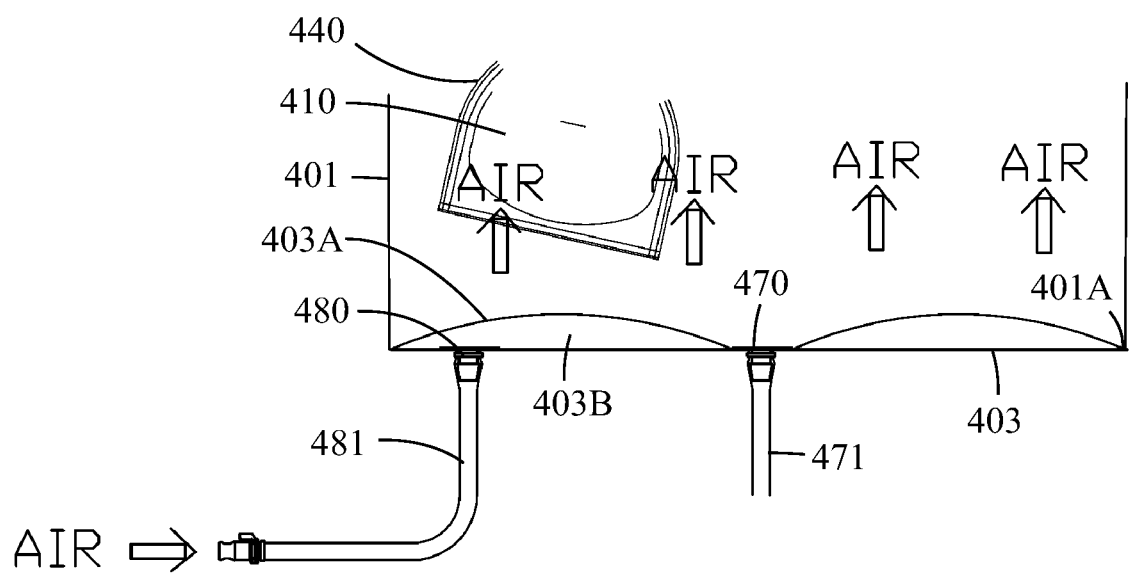
FIG. 8B is a side cross-sectional view of a lower portion of the mixing tank of FIG. 8A taken along section lines A-A depicted in FIG. 8A.

Referring to FIGS. 8A-8B, a mixing tank according to one embodiment includes a double bottom comprising a first perforated or porous material layer 403A disposed over a second impermeable material (or bottom) 403 in communication with an air or gas inlet port 480. The perforated or porous layer 403A which is preferably comprises a microperforated or microporous material as described previously, is joined to the bottom 403 along the inner surface 401A of the tank 401, and along the drain outlet 470 to form an annular pocket 403B. The mixing tank 401 further includes a top 404, coupling guide 405, and a mixing paddle 410 and shaft 430 disposed in a sealed sleeve 440. The mixing paddle 410 is preferably adapted to travel in a substantially circular path at a nonzero angle relative to a central vertical axis (not shown) of the mixing tank 401. In operation, pressurized air or another desired gas is supplied via an inlet tube 481 through the inlet port 480 into the annular pocket 403B, where it escapes through holes defined in the perforated or porous layer 403A into the interior of the tank 401. In this manner, the passage of air into the tank is widely dispersed as small bubbles without requiring the use of high speed turbine agitators. Preferably, the pocket 403B is maintained at a higher pressure than any portion of the interior of the tank 401 to minimize or eliminate leakage from the tank into the pocket 403B.

Figure 9A:
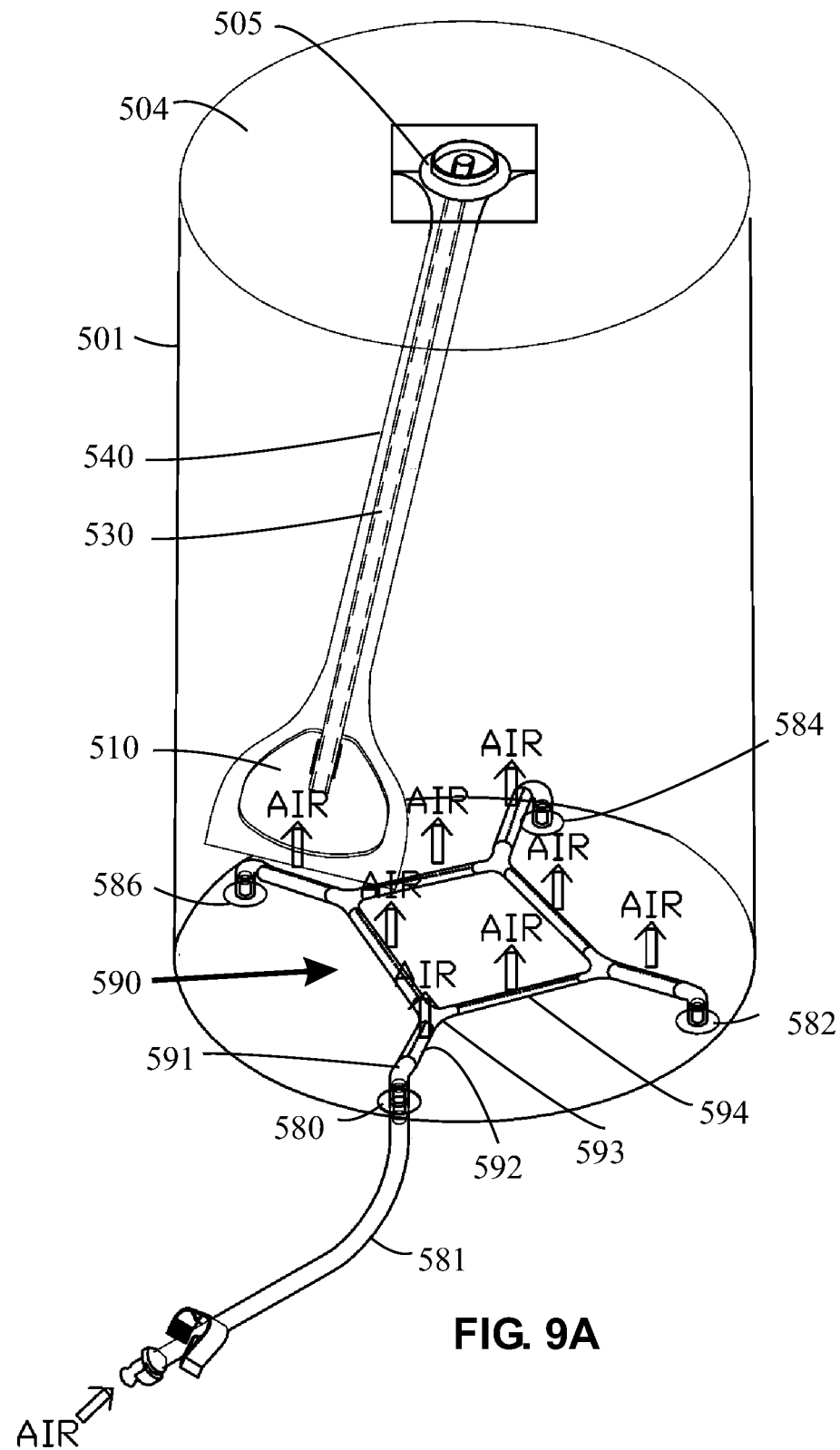
FIG. 9A illustrates a perspective view of a mixing tank having a mixing paddle and an air distribution manifold including perforated tubes disposed along the bottom of the tank, with arrows indicating the direction of air passage into the interior of the tank, according to an aspect of the present invention.

In another embodiment, referring to FIG. 9A, a mixing tank 501 may include an internal air distribution manifold or sparger 590 in fluid communication with an external air or gas source (not shown) via an air or gas inlet 580. The sparger 590 may be assembled from elbow fittings 591, peripheral perforated tubes 592, Y-fittings 593, and central perforated tubes 594, which permit air to be injected along the bottom of the tank 501 in a dispersed manner as small bubbles without requiring the use of high speed turbine agitators (impellers). Microperforated or microporous tubes may be used in place of the tubes 592, 594. Preferably, the sparger 590 is maintained at a higher pressure than any portion of the interior of the tank 501 to minimize or eliminate leakage from the tank into the sparger 590. Three anchors 582, 584, 586, not requiring external fluidic connections, may be provided to secure the sparger 590 to the tank 501. Alternatively, gas inlets 582, 584, 586 may be substituted for the anchors if desired to aid in gas distribution and/or permit multiple gases to be mixed in the sparger 590 and supplied to the tank 501. The mixing tank 501 further includes a top 504, coupling guide 505, and a mixing paddle 510 and shaft 530 disposed in a sealed sleeve 550 and adapted to travel within the tank 501. While not shown in FIG. 9A, a tank 501 would desirably include one or more additional inlet and outlet connections of various types, such as to permit the addition or removal of various substances and/or enable sensors to be provided in sensory communication with the interior of the tank 501.

FIG. 9B illustrates the bottom wall 603 and air manifold or sparger portions of a mixing tank similar to the tank depicted in FIG. 9A. The manifold or sparger 690, which is preferably in fluid communication with an external air or gas source (not shown) via an inlet port 680, may be assembled from elbow fittings 691, peripheral perforated or porous (preferably microperforated or microporous) tubes 692, Y-fittings 693, and central perforated or porous tubes 694. The sparger 690 preferably is further secured to the bottom wall via anchors 682, 684, 686; however, in an alternative embodiment, gas inlets may be substituted for any one or more of the anchors 682, 684, 686 to further aid in promoting even gas distribution to the manifold and/or to supply various different gases to the sparger 690 for mixing therein. The bottom wall 603 further includes various ports 671A-671D and 672A-672D to permit communication with various fluid supply or drain lines, filters, sensors, and/or sample receptacles (e.g., bags).

FIG. 9C illustrates the bottom wall 656 of a support container (such as the container 250 illustrated in FIGS. 5A-5B) adapted for use with a mixing tank having the bottom wall 603 illustrated in FIG. 9B. In particular, the container bottom wall 656 defines various apertures 660, 651-654 to permit access to the various ports 670, 671A-671D, 672A-672D, 680 of the tank bottom wall 603 of FIG. 9A, while still providing structural support for a flexible tank.

Spargers (e.g., fixed spargers) of various sizes and shapes may be disposed in any of various locations along the bottom or side walls of a mixing vessel. Examples of possible sparger placement in this regard are illustrated in connection with the processing system 900A of FIG. 12. Such system 900A includes multiple rods 930A, 930B each having at least one associated mixing paddle 910A, 910B adapted to move within a common closed tank 901A. A benefit of using multiple mixing paddles 910A, 910B is that they can promote uniform mixing in very large volume tanks. The tank 901A, which is generally parallelepiped-shaped, has a top wall 904A defining a substance inlet 960A and access ports 980A, 985A, and has a bottom wall 903A defining an outlet or drain 970A. The tank 901A further includes two sealed sleeves 940A, 940B joined to the tank 901A along reinforced coupling guides 905A, 905B. Each sealed sleeve 940A, 940B contains a mixing paddle 910A, 910B joined to a hollow shaft 930A, 930B. Adjacent to each coupling guide 905A, 905B is a pivot guide 815A, 815B (e.g., having a perforated pivot ball) through which a transfer shafts 830A, 830B extend to engage (e.g., by insertion) the hollow shafts 930A, 930B disposed below. (While hollow shafts 930A, 930B, separate transfer shafts 830A, 830B, and bottom-insert or pre-sealed mixing paddles 810A, 910B are shown, unitary shafts and/or top-insert mixing paddles may be used if desired.) Each transfer shaft 830A, 830B is linked to a radially offset coupling 812A, 812B that engages the output shaft 811A, 811B of a motor 899A, 899B. While two motors 899A, 899B are shown and represent a preferred embodiment, one motor could be used in combination with a gearset or other appropriate linkage (not shown) to drive two or more paddles if desired. Each motor 899A, 899B is supported by a support frame 808A, with extensions 809A, 809B thereof further supporting the pivot guides 815A, 815B. Preferably, the support frame 808A further engages the mixing tank 901A to ensure correct positioning between the motors 899A, 899B, the transfer shafts 830A, 830B and the contents of the sleeves 940A-940B.

One sparger or multiple spargers 990A-990D may be disposed along bottom wall 903, and one of more spargers 995A-995D may be disposed along side walls 901A, of the tank 901. Each sparger 990A-990D, 995A-995D may include a section of microporous or microperforated tubular or sheet material. A tubular material may be added to an existing pipe nipple or other tube and then capped along one end. Each sparger 990A-990D, 995A-995D is preferably in fluid communication with an external gas source (not shown). A flow control element such as a valve (not shown) is preferably provided between a sparger 990A-990D, 995A-995D and a gas source.

To provide enhanced mass transfer, a sparger may be adapted to travel with a mixing paddle in further embodiments of the present invention, such as illustrated in FIG. 16. Such figure illustrates a perspective view of a mixing apparatus 1300 including a parallelepiped-shaped mixing tank 1301 having an integral sleeve 1340 with a mixing paddle 1310 disposed therein, with a sparger 1375 arranged to travel with the paddle 1310 and supply gas to the interior of the tank 1301. A support rod 1330 is linked to the paddle 1310 within the sleeve 1340. Near the paddle 1310, the sparger 1375 is provided outside the sleeve 1340 to enable fluid communication with the contents of the tank 1301. A gas supply conduit 1365 in fluid communication with the sparger 1375 may be disposed within the sleeve 1340. As illustrated, the sparger 1375 comprises a microporous or microperforated tubular material. End caps 1374, 1375 may be provided along the ends of the tubular material. A conduit segment 1368 supports the sparger 1375 outside the sleeve 1340 and provides fluid communication with the gas supply conduit 1365. A second conduit segment 1366 may be provided along the other end of the sparger 1375, but such segment 1366 need not be in fluid communication with the sparger 1375. Because the paddle 1310 does not rotate continuously about a longitudinal axis of the support rod 1330, there is no danger of twisting the gas supply conduit 1365 to the point of failure. The tank 1301 further includes a coupling guide 1305 (that is preferably more rigid than a film material with which the tank is preferably constructed) that permits pivotal arrangement of the support rod 1330 between an external kinetic energy source (not shown) and the interior of the tank 1301. Ports 1360, 1362 may be provided along an upper surface of the tank 1301.

Positioning the sparger to travel with the mixing paddle has been found to be advantageous in terms of greatly enhancing $K_{La}$. While applicants do not wish to be bound by any theory for such phenomenon, it is believed that generation of turbulent regions by the paddle as it travels through the tank increased dispersion of gas bubbles into liquid contents of the tank. Various possible configurations for supporting a sparger to travel with a paddle within a mixing tank are illustrated in FIGS. 17A-17F.

FIG. 17A illustrates a portion of a material processing apparatus, including a paddle-containing sleeve 1440A and a sparger element 1475A supported by two conduit segments 1466A, 1468A. At least the first segment 1466A is in fluid communication with the gas supply conduit 1465A to supply gas to the sparger element 1475A. First and second fitments 1455A, 1456A are provided along a lower seam of the sleeve 144A to structurally interconnect the segments 1466A, 1468A and the sleeve 1440A while permitting gas flow into the segment 1466A from the gas supply conduit 1465 disposed within the sleeve 1440A. If desired, the segment 1466A may be a continuous extension of the gas supply conduit 1465A; alternatively, any suitable hollow interconnect may be provided to connect such conduits 1466A, 1465A. A plug 1458A may be provided within the sleeve 1440A adjacent to the second fitment 1456A to plug the second segment 1468A, to ensure that any gas supplied to the sparger 1475A is released through the gas-permeable material. A welded seam 1441A is preferably made around the perimeter of the sleeve over the fitments 1455A, 1456A. The sleeve 1440A further contains a paddle 1410A and associated support rod 1430A.

Another embodiment is shown in FIG. 17B, which illustrates a paddle-containing sleeve 1440B with a sparger element 1475B supported by a single gas supply segment 1466B routed through a fitment 1455B and in fluid communication with a gas supply conduit 1465B. The sparger 1475B may be formed of a microporous or microperforated tube, with a distal end of the tube covered with a cap, plug, or microporous membrane (not shown). Depending on the rigidity of the conduit segment 1466B, the sparger 1475B may be substantially fixed in position relative to the paddle 1410B and sleeve 1440B, or the sparger 1475B may subject to some movement relative to the paddle 1410B or sleeve 1440B when the paddle 1410B and associated support rod 1430B are driven to travel within a mixing tank. The sleeve 1440B includes a peripheral seam 1441B that extends over the fitment 1455B and is preferably formed by welding.

Another embodiment is shown in FIG. 17C, which illustrates a paddle-containing sleeve 1440C (and associated support rod 1430C) with a sparger element 1475C supported by a two conduit segments 1466C, 1468C routed through a single large fitment 1455C that permits fluid communication between the sparger 1475C and a gas supply conduit 1465C disposed within the sleeve 1440C. A plug 1458C may be provided within the sleeve 1440C adjacent to the fitment 1455C to plug the second segment 1468C, to ensure that any gas supplied to the sparger 1475C is released through the gas-permeable material thereof. The sleeve 1440C includes a peripheral seam 1441C that extends over the fitment 1455C and is preferably formed by welding. The first segment 1466C, or the first and second segments 1466C, 1468C, may be a continuous extension of the gas supply conduit 1465C.

As illustrated in FIGS. 17D-17E, the preceding sleeve-conduit fitments (i.e., illustrated in connection with FIGS. 17A-17C) may be omitted, in favor of direct structural connection (e.g., welding) between a gas supply conduit 1465E and the sleeve material. Referring to FIG. 17D, sleeve 1440D containing a paddle 1410 and associated support rod 1430D further contains a gas supply conduit 1465D that passes through a peripheral seam 1441D to form conduit segment 1466D that supports a sparger 1475D. Such sparger 1475D is further supported by another conduit segment 1468D that passes back through the peripheral seam 1441D of the sleeve 1440D to receive a cap 1458D. The segments 1466D, 1468D support the sparger 1475D from the sleeve 1440D.

FIG. 17E is substantially similar to FIG. 17D, but with the omission of the second conduit segment 1468D. Referring to FIG. 17E, a sleeve 1440E containing a paddle 1410E and associated support rod 1430E further contains a gas supply conduit 1465E that passes through a peripheral seam 1441E to form conduit segment 1466E that supports a sparger 1475E. Gas supplied to the conduit 1465E passes through the conduit 1466E to the sparger 1475E to be released through the gas-permeable (e.g., microporous or microperforated) material thereof.

Figure 17F:
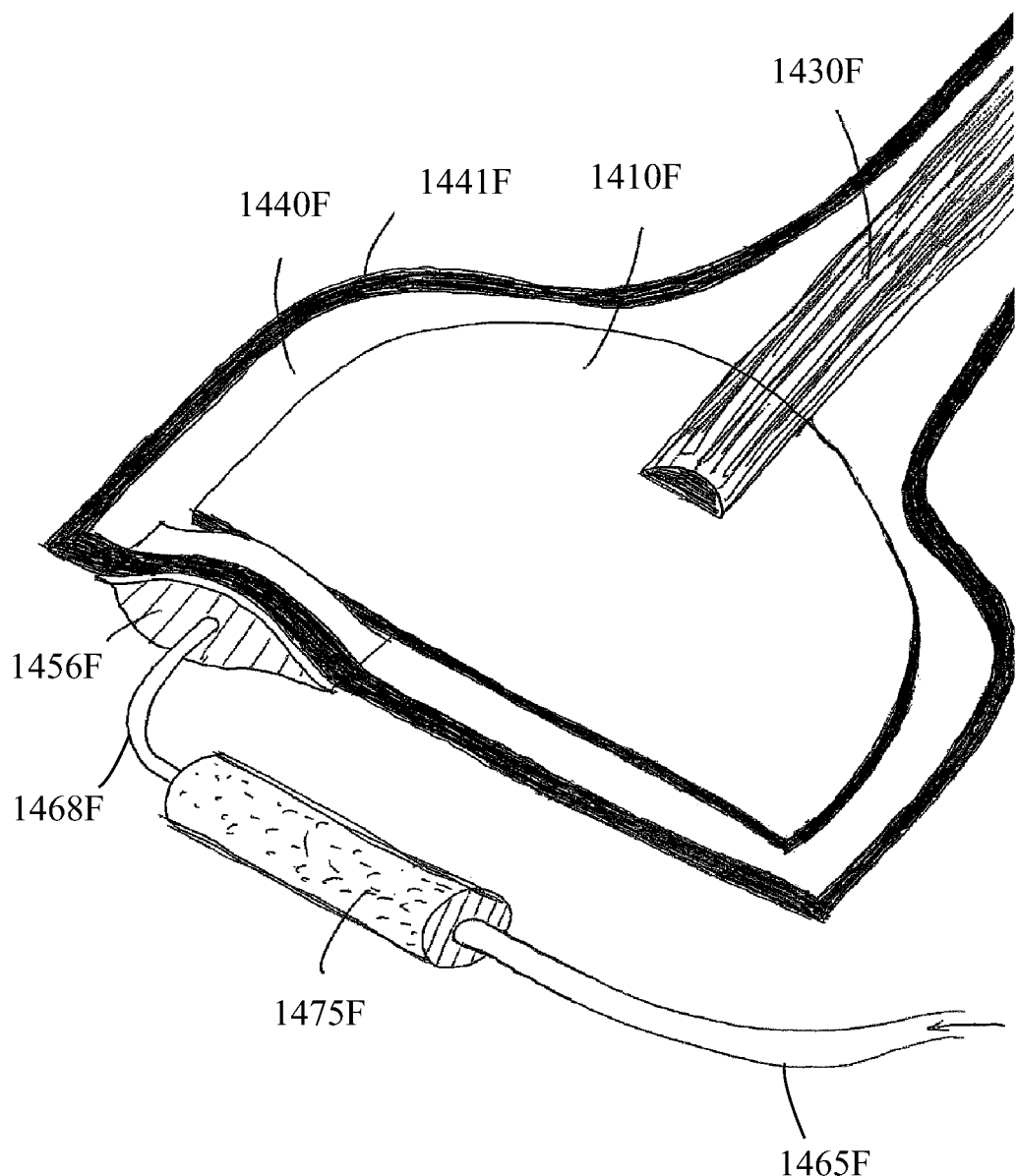
FIG. 17F illustrates a perspective view of a portion of a material processing apparatus according to an aspect of the present invention, including a paddle-containing sleeve and a sparger element supported by a fitment and single conduit affixed to the sleeve, with a gas supply tube provided outside the sleeve and in fluid communication with the sparger.

While FIGS. 17A-17E illustrate a gas supply conduit routed through a paddle sleeve, it is to be appreciated that a gas supply conduit may be routed outside the sleeve to a wall of the tank, such as shown in FIG. 17F. In such an embodiment, the gas supply conduit extends through a wall of the tank to permit fluid communication with an external gas source (not shown) for supplying gas to the sparger. Again, because the paddle does not rotate continuously about a longitudinal axis of the support rod, there is no danger of twisting the gas supply conduit to the point of failure. Referring to FIG. 17F, a sleeve 1440F containing a paddle 1410F and associated support rod 1430F includes a fitment 1456F that receives a conduit segment 1468F attached to a sparger 1475. The conduit segment 1468F is preferably blocked or plugged to prevent passage of gas, to ensure than any gas supplied to the sparger 1475F flows outwardly through the gas-permeable material thereof. Along an opposite end of the sparger 1475F, the sparger 1475F receives a gas supply conduit 1465F that preferably passes through a wall of a surrounding container (not shown). The gas supply conduit 1465F preferably has sufficient flexibility and slack not to impede travel of the paddle 1410F in operation. Gas supplied to the conduit 1465E passes to the sparger 1475D to be released through the gas-permeable (e.g., microporous or microperforated) material thereof.

In certain embodiments, a sparger may be integrated with a sleeve or paddle, with a surface of such sleeve or paddle being formed of a porous or perforated (preferably microporous or microperforated) material and in fluid communication with an external gas source. One example of a sparger integrated with a sleeve is illustrated in FIGS. 18A-18B. A paddle 1510 and support rod 1530 are disposed within a sleeve 1540 that is preferably formed by welding sheets of a polymeric film material along peripheral edges thereof to form a cavity bounded by a peripheral seam 1541. Disposed along a portion of the sleeve 1540 is a sparger 1575 including a gas-permeable (preferably microporous or microperforated) material 1575 in fluid communication with an external gas source (not shown) by way of a gas supply conduit 1565 routed through the sleeve 1540. The gas-permeable material 1575A material may comprise a membrane that is peripherally welded to the sleeve 1550. Referring to FIG. 18B, a hollow elbow 1578 including a flange portion 1578 and defining a gas flow passage 1578A provides an interface between the gas supply conduit 1565 and the gas-permeable material 1575A. A flared or barbed connector 1579 may be provided along the elbow 1578 to facilitate connection to the gas supply conduit 1565. In operation, gas supplied through the gas supply conduit 1565 passes through the hollow elbow 1577 to the gas-permeable material 1575A of the sparger 1575 and flows through holes defined therein into the interior of the tank to contact material to be processed.

Figure 19:
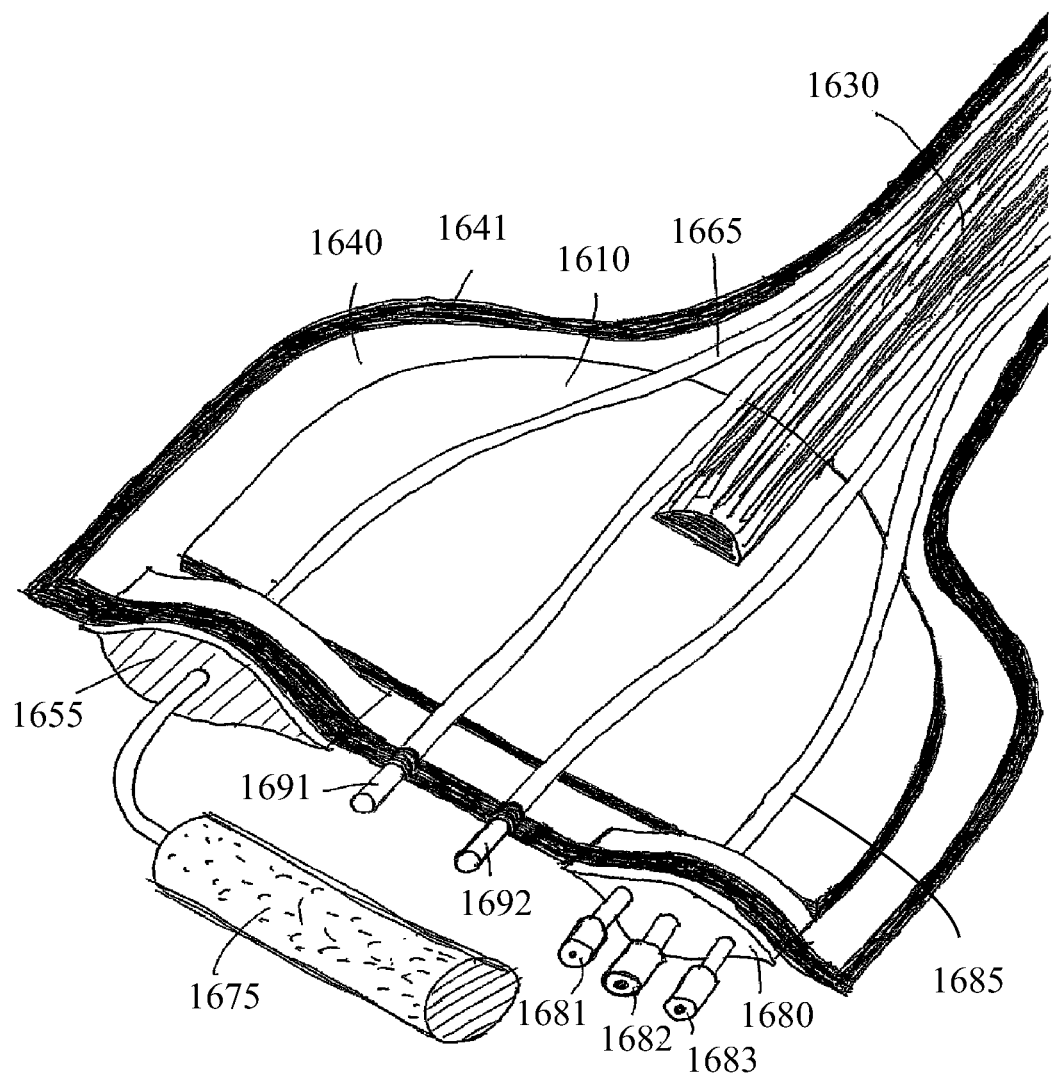
FIG. 19 illustrates a perspective view of a portion of a mixing apparatus according to an aspect of the present invention, including a paddle-containing sleeve with multiple functional elements, including (1) a sparger element supported by a gas supply tube passing once through a fitment affixed to the sleeve, (2) a material addition conduit, (3) a material extraction conduit, and (4) multiple sensors supported by a receptacle affixed to the sleeve.

In further embodiments, other functional elements besides a sparger may be arranged to travel with a mixing paddle. Such functional element may be attached in whole or part to any of a paddle, a support rod, or sleeve. Functional elements may be integrated with a paddle and/or associated support rod (e.g., in a sleeveless embodiment) or with a sleeve (in embodiments where a sleeve is provided to isolate a paddle from contacting the interior of a tank). With respect to such an embodiment including a sleeve, FIG. 19 illustrates a mixing paddle 1610 and sleeve 1640 having a material addition conduit 1691, a material extraction conduit 1692 (e.g., for extracting periodic samples to be analyzed), and multiple sensors 1681-1683, such as a temperature sensor 1681, a pH sensor 1682, and an oxygen sensor 1683. A sparger 1675 further provided in fluid communication with a gas supply conduit 1665 passing through a fitment 1655 disposed along a peripheral seam 1641 of the sleeve 1640. Another example of a functional element that could be provided to travel with a mixing paddle is a heat exchange element (not shown), which may include an electrically driven heat exchange device (e.g., a resistance heater or thermoelectric device) or a circulating fluid communicable with an external heat source or sink. One or more electrical conductors or fluid conduits (e.g., for conducting a heat exchange fluid) may be associated with such heat exchange device. By arranging functional elements to travel with the mixing paddle 1610, substantial flow rates of fluid relative to the functional elements (e.g., elements 1675, 1681-1683, 1691, 1692) are achieved. The motion and mixing action of the paddle tends to quickly eliminate local (positional) variation of fluid conditions.

Each functional element may include an associated interface. For example, with continued reference to FIG. 19, the sparger has an associated gas supply tube 1665 (and fitment 1655), the material addition conduit may include a material addition segment passing through the seam 1641, the material extraction conduit may include a material distraction segment passing through the seam 1641, and the sensors 1681-1683, which are mounted to a receptacle 1680 (or fitment) may include one or more associated electrical conductors 1685. Such interface elements may be routed through the sleeve; alternatively, if a sleeve is not provided, then such interface elements may be routed through or along the support rod, optionally disposed within a sheath (not shown). A plug or receptacle may be used any for each functional element or all functional elements to permit rapid connection and disconnection of desired components (e.g., spargers of different sizes, sensors of different types, heat exchangers of different capacity, etc.).

In a further embodiment, one or more sensors may be adapted to communicate wirelessly with an isolated signal receiver or antenna. Such sensors may be self-powered, whether by battery or by rectifying an input signal to derive useable power. RFID technology may be used for wireless communication. In one embodiment, an interface element for a sensor includes any of a wireless transmitter and a wireless receiver. For example, a wireless transmitter may be placed in or along a paddle or sleeve in electrical communication with a receptacle (e.g., receptacle 1680) adapted to receive a sensor in fluid communication with the contents of a tank. Signals from such a sensor are communicated to the transmitter, which sends a signal to a remotely located receiver, which may be disposed outside a material processing tank.

Figure 20:
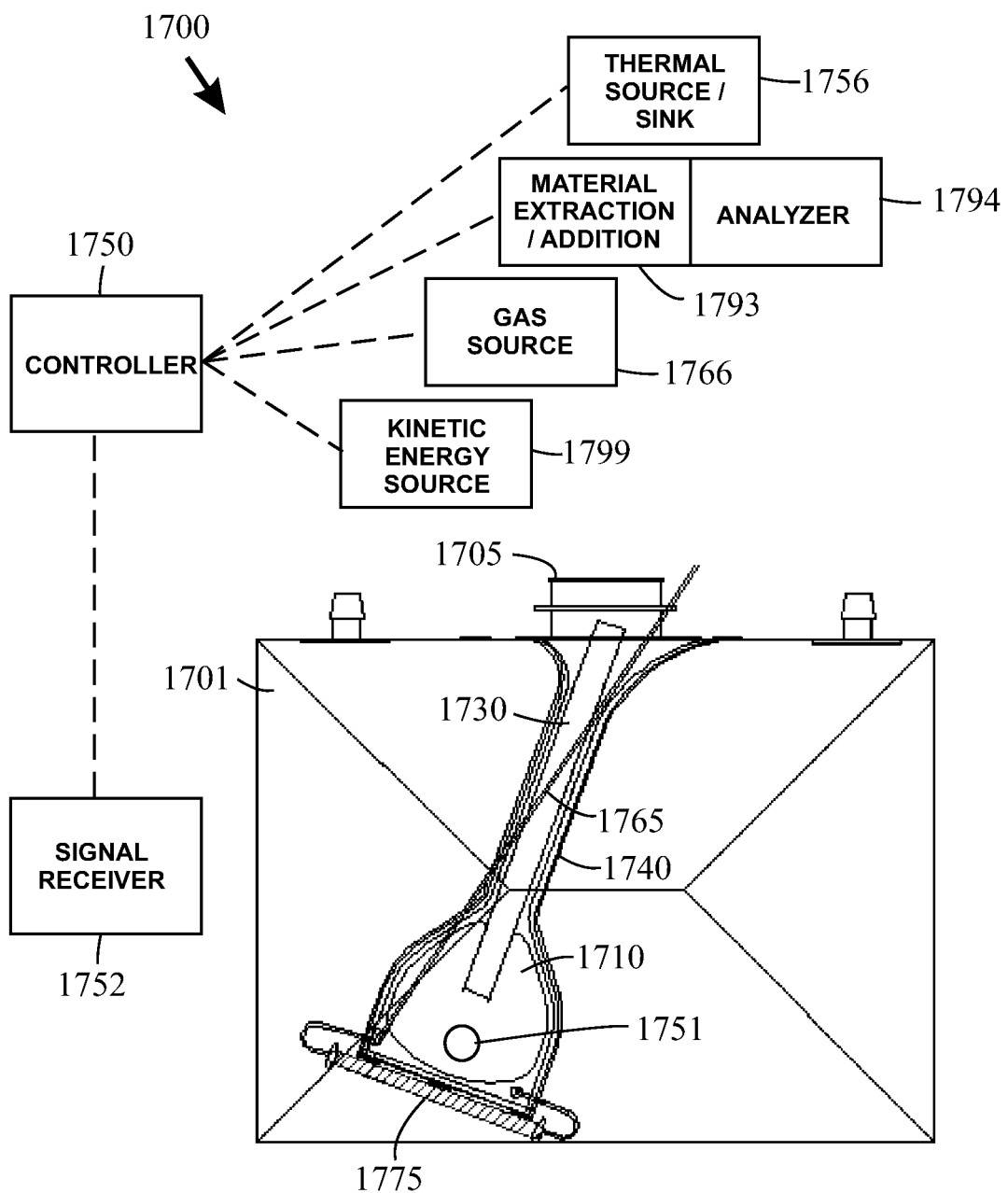
FIG. 20 provides a schematic of various elements of a fluid processing system including a parallelepiped-shaped mixing tank having an integral sleeve with a mixing paddle disposed therein, according to an aspect of the present invention.

Various components of a material processing system 1700 are shown in FIG. 20. A tank-mounted mixing paddle 1710, support rod 1730, and optional sleeve 1740 may include any of various functional elements described herein. For example, a sparger 1775 is arranged to travel with the paddle 1710, and is in fluid communication with a gas supply conduit 1765 that is preferably routed through the sleeve 1740. A wireless transmitter 1751 may be associated with the paddle 1710 or sleeve 1740. A signal receiver 1752 may be disposed remotely, such as outside the tank 1701, to receive signals from the wireless transmitter 1751. The wireless transmitter 1751 may be adapted to receive signals from one or multiple sensors (not shown) adapted to travel with the paddle 1710 within the tank 1701. Proximate to the tank 1701 are various appurtenant elements including a kinetic energy source 1799 adapted to drive the mixing paddle 1710, a gas source 1766 adapted to supply gas to the sparger 1775, material extraction and/or addition components 1793 (which may include various flow control elements, material containers, and the like) with an optional analyzer 1794 (e.g., for use with extracting discrete samples via the material extraction conduit), and a thermal source or sink subsystem 1756 adapted to promote temperature control of the tank 1701. A controller 1750 may be provided to receive various sensory inputs and provide command signals to any of the various components of the system 1700. The controller 1750 is preferably microprocessor-based and adapted to automate the system 1700 while permitting execution of user-defined or preprogrammed instructions.

To test the efficacy of baffles and various (fixed) gas injection or sparger elements, Applicants constructed a flexible mixing tank and tested the same with support containers with and without baffles to determine $K_{la}$ values. An ATMI C-mix system employing a polymeric film-based flexible bag-type mixing tank (200 liter volume, 575 mm diameter, 900 mm height) was used in conjunction with a mixing paddle apparatus such as illustrated in FIGS. 2A-2B. Tests were performed with both 100 liter and 200 liter fluid volumes, with varying mixing paddle angles (departure from central vertical axis of tank) to avoid contact between the paddle and baffles, with varying mixing speeds and air flows, with various air inlet positions, and with or without two baffles of 50 millimeter diameter. Data obtained from these tests are reproduced below.

without the benefit of extensive optimization efforts, such that the values obtained should not be construed as upper performance limits for corresponding devices.

Figure 21:
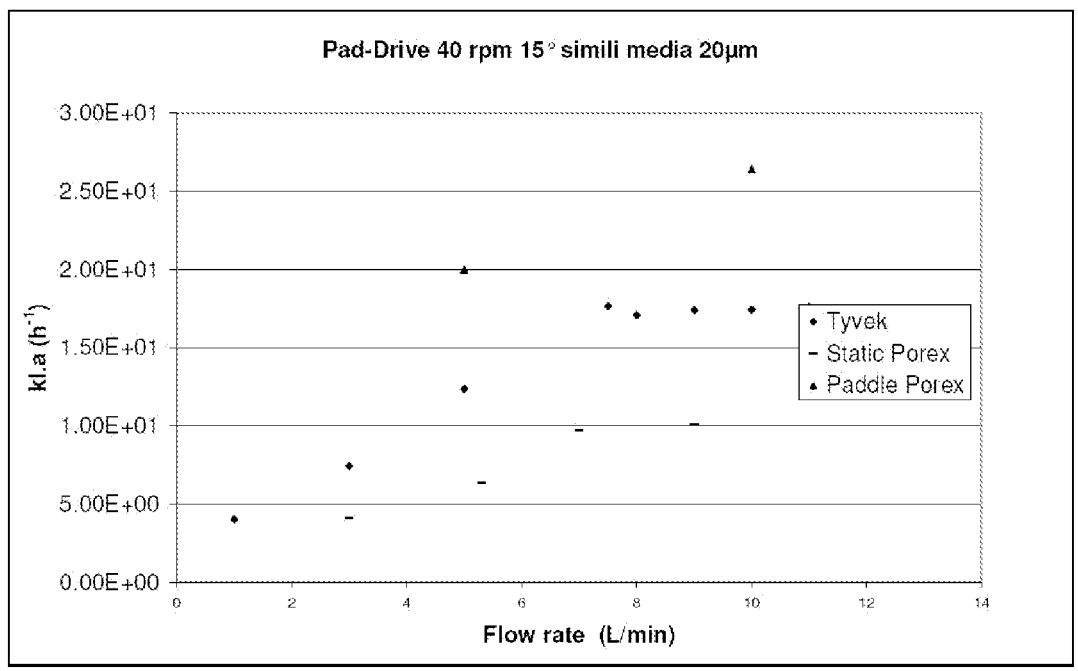
FIG. 21 is a plot of experimental data providing $K_{la}$ values as a function of gas flow rate obtained for mixing apparatuses according to an aspect of the present invention, with one run each corresponding to use of a static sparger including a static Tyvek® material, a static sparger including a Porex® material, and a paddle-supported sparger including a Porex® material.

The benefit of adding a sparger (such as a sparger including a microporous or microperforated material) to a paddle is illustrated in FIG. 21, which provides a plot of experimental data providing $K_{la}$ values as a function of gas flow rate obtained for mixing apparatuses according to an aspect of the present invention, for runs performed at low paddle speeds and flow rates suitable for cell culture. Three data series are illustrated, with one run each corresponding to use of a static sparger including a static Tyvek® material, a static sparger including a Porex® material, and a paddle-supported sparger including a Porex® material. The paddle-supported sparger yielded approximately 50% greater $K_{La}$ performance than the other placements, under equivalent conditions.

In further embodiments, a mixing tank/bioreactor may include external heating and/or cooling means useful in conjunction with one or more temperature sensors such as described hereinabove for controlling the temperature of components in the disposable mixing tank. In one embodiment, a circulation loop may be provided to direct a portion of the contents of the mixing tank through a heat exchanger (to provide heating or cooling utility) and back into the tank. In another embodiment, an external support container and/or a secondary containment system may envelop the exterior of the disposable mixing tank or a portion thereof to serve as a housing for a thermal exchange fluid (that is preferably circulatable around the exterior of the mixing tank, such as with a pump) to conduct heat into or out of the mixing tank via the tank wall, preferably with an external heat exchanger in fluid communication with the thermal exchange fluid. For example, a double walled support container having a circulatable water bath connected to an external pump and

TABLE 1

$K_{La}$ Data

| Test | Volume of water (L) | Angle of mixing paddle (°) | Mixing speed (RPM) | Air Flow (L/h) | Position of air inlet | $K_La$ (1/h) | Baffles used? (2 × 50 mm diam.) |
|---|---|---|---|---|---|---|---|
| 1 | 100 | 12.5 | 100 | 400 | Bottom tube | 15 | No |
| 2 | 100 | 12.5 | 100 | 400 | On the mixing paddle | 14 | No |
| 3 | 100 | 12.5 | 100 | 6000 | On the mixing paddle and from bottom tube | 99 | No |
| 4 | 100 | 12.5 | 100 | 6000 | Bottom tube | 95 | No |
| 5 | 100 | 12.5 | 50 | 6000 | Bottom tube | 59 | No |
| 6 | 200 | 12.5 | 100 | 6000 | On the mixing paddle and from bottom tube | 72 | No |
| 7 | 100 | 12.5 | 100 | 6000 | 2 perforated tubes | Very low | No |
| 8 | 100 | 12.5 | 100/100 alternating | 6000 | 2 perforated tubes | 57 | No |
| 9 | 100 | 9 | 100 | 6000 | On the mixing paddle and from bottom tube | 122 | Yes |
| 10 | 100 | 9 | 100 | 6000 | On the mixing paddle and from bottom tube | 106 | Yes |
| 11 | 100 | 9 | 100 | 6000 | On the mixing paddle and from bottom tube | 126 | Yes |
| 12 | 200 | 9 | 100 | 6000 | On the mixing paddle and from bottom tube | 100 | Yes |
| 13 | 100 | 9 | 100 | 6000 | On the bottom 2m perforated tube | 195 | Yes |
| 14 | 200 | 9 | 100 | 6000 | On the bottom 2m perforated tube | 150 | Yes |

In a subsequent test performed in the same apparatus, a $K_{la}$ value of 195/h was obtained with 6000 liters per hour of air flow into 100 liters with two baffles in place. It is noted that the foregoing data represents early experimental results heater/chiller unit with heat exchanger may be employed A heat exchange subsystem may include any appropriate components such as heating jackets, heating and cooling tanks, heat exchangers, chillers, and fluid cooling systems.

Material processing apparatuses and systems according to embodiments of the present invention are useful for fermentation or culturing living cells, with such cells being processable or adapted to yield a variety of useful products including chemicals, biochemicals, and organic compounds. More specific examples of useful products include antibiotics (e.g., pen, streptomycin, etc.), enzymes (e.g., proteases, cellulases, hemicellulases, etc.); pharmaceutical and biopharmaceuticals (e.g., antibodies, vaccines, etc.), food/industrial additives (e.g., vitamins, amino acids, citric acid, acetic acid, arabic gum, xanthan gum, monosodium glutamate, etc.); aroma molecules (e.g., termineol), biodegradable plastics (e.g., polyhdryoxibutyrate); biopolymers, pigments, dyes, insecticides, and the like.

Apparatuses according to the present invention are well suited for performing methods of culturing living cells. A first method of culturing cells utilizes an apparatus with a mechanically driven mixing paddle and a functional element arranged to move with a mixing paddle within a tank (as described hereinabove), and includes the steps of: supplying a plurality of materials to the tank; driving the mixing paddle to move within the tank; and applying the functional element to at least a portion of the materials within the tank. The living cells may be adapted to yield any of a chemical, a biochemical, and an organic compound. The living cells may be further adapted to yield any of an antibiotic material, an enzyme, an antibody, and a vaccine A second method of culturing cells utilizes an apparatus with a mechanically driven mixing paddle and a functional element interface adapted for coupling with a functional element arranged to travel with a mixing paddle, wherein the functional element is in fluid communication or sensory communication with the interior of a tank (as described hereinabove), and includes the steps of: supplying a plurality of materials to the tank; driving the mixing paddle to move within the tank; and utilizing the functional element interface in application of a functional element to at least a portion of the materials in the tank. The living cells may be adapted to yield any of a chemical, a biochemical, an organic compound, an antibiotic material, an enzyme, an antibody, and a vaccine A third method of culturing cells utilizes an apparatus with a sparger and a mixing paddle disposed within the interior of the tank, the paddle being adapted to engage a support rod mechanically coupleable to receive kinetic energy from a kinetic energy source, with the apparatus being adapted to permit pivotal movement of the support rod between the kinetic energy source and the mixing tank; such method includes the steps: of supplying a plurality of materials to the tank; driving the mixing paddle to move within the tank; and supplying gas through the sparger to the interior of the tank.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A material processing apparatus comprising:
   a hollow tank having an interior bounded by at least one interior wall;
   a mixing paddle disposed and adapted to travel within the interior of the tank, the paddle being adapted to engage a support rod mechanically coupleable to receive kinetic energy from a kinetic energy source; and
   a functional element arranged to travel with the mixing paddle within the interior of the tank, the functional element comprising at least one sensor in sensory communication with the interior of the tank;
   wherein the tank comprises a flexible sleeve having an open end proximate to a wall of the tank, having an end protruding into the interior, having at least one exterior wall, and defining a cavity containing the mixing paddle, with the at least one interior wall of the tank and the at least one exterior wall of the sleeve enclosing a volume, such that the sleeve serves as an isolation barrier impermeable to any fluid of the volume;
   wherein the functional element is adapted to interact with the flexible sleeve.

2. The apparatus of claim 1, further comprising a wireless receiver, wherein the at least one sensor is adapted to communicate with the wireless receiver.

3. A material processing apparatus comprising:
   a hollow tank having an interior bounded by at least one interior wall;
   a mixing paddle disposed and adapted to travel within the interior of the tank, the paddle being adapted to engage a support rod mechanically coupleable to receive kinetic energy from a kinetic energy source; and
   a functional element arranged to travel with the mixing paddle within the interior of the tank, the functional element comprising a material extraction conduit in at least selective fluid communication with the interior of the tank and adapted to permit the extraction of material from the interior of the tank;
   wherein the tank comprises a flexible sleeve having an open end proximate to a wall of the tank, having an end protruding into the interior, having at least one exterior wall, and defining a cavity containing the mixing paddle, with the at least one interior wall of the tank and the at least one exterior wall of the sleeve enclosing a volume, such that the sleeve serves as an isolation barrier impermeable to any fluid of the volume;
   wherein the functional element is adapted to interact with the flexible sleeve.

4. A material processing apparatus comprising:
   a hollow tank having an interior bounded by at least one interior wall;
   a mixing paddle disposed and adapted to travel within the interior of the tank, the paddle being adapted to engage a support rod mechanically coupleable to receive kinetic energy from a kinetic energy source; and
   a functional element arranged to travel with the mixing paddle within the interior of the tank, the functional element comprising a material addition conduit in at least selective fluid communication with the interior of the tank and adapted to permit the addition of a material to the interior of the tank;
   wherein the tank comprises a flexible sleeve having an open end proximate to a wall of the tank, having an end protruding into the interior, having at least one exterior wall, and defining a cavity containing the mixing paddle, with the at least one interior wall of the tank and the at least one exterior wall of the sleeve enclosing a volume, such that the sleeve serves as an isolation barrier impermeable to any fluid of the volume;
   wherein the functional element is adapted to interact with the flexible sleeve.

5. A material processing apparatus comprising:
a hollow tank having an interior bounded by at least one interior wall;
a mixing paddle disposed and adapted to travel within the interior of the tank, the paddle being adapted to engage a support rod mechanically coupleable to receive kinetic energy from a kinetic energy source; and
a functional element arranged to travel with the mixing paddle within the interior of the tank, the functional element comprising
  (a) a material extraction conduit in at least selective fluid communication with the interior of the tank and adapted to permit the extraction of material from the interior of the tank; and
  (b) a material addition conduit in at least selective fluid communication with the interior of the tank and adapted to permit the addition of a material to the interior of the tank;
wherein said material extraction conduit and said material addition conduit comprise a common conduit, and said functional element comprises said common conduit;
wherein the tank comprises a flexible sleeve having an open end proximate to a wall of the tank, having an end protruding into the interior, having at least one exterior wall, and defining a cavity containing the mixing paddle, with the at least one interior wall of the tank and the at least one exterior wall of the sleeve enclosing a volume, such that the sleeve serves as an isolation barrier impermeable to any fluid of the volume;
wherein the functional element is adapted to interact with the flexible sleeve.

6. A material processing apparatus comprising:
a hollow tank having an interior bounded by at least one interior wall;
a mixing paddle disposed and adapted to travel within the interior of the tank, the paddle being adapted to engage a support rod mechanically coupleable to receive kinetic energy from a kinetic energy source; and
a functional element arranged to travel with the mixing paddle within the interior of the tank, the functional element including any of:
  (a) at least one sensor in sensory communication with the interior of the tank;
  (b) a material extraction conduit in at least selective fluid communication with the interior of the tank and adapted to permit the extraction of material from the interior of the tank;
  (c) a material addition conduit in at least selective fluid communication with the interior of the tank and adapted to permit the addition of a material to the interior of the tank; and
  (d) a heat exchange element in thermal communication with the interior of the tank and adapted to permit the addition or removal of thermal energy from the interior;
wherein the tank comprises a flexible sleeve having an open end proximate to a wall of the tank, having an end protruding into the interior, having at least one exterior wall, and defining a cavity containing the mixing paddle, with the at least one interior wall of the tank and the at least one exterior wall of the sleeve enclosing a volume, such that the sleeve serves as an isolation barrier impermeable to any fluid of the volume;
wherein the functional element is adapted to interact with the flexible sleeve; and
further comprising at least one of the following elements disposed within the flexible sleeve: an electrical conductor, a fluid conduit, the at least one sensor, and a wireless communication device.

7. A material processing apparatus comprising:
a hollow tank having an interior bounded by at least one interior wall;
a mixing paddle disposed and adapted to travel within the interior of the tank, the paddle being adapted to engage a support rod mechanically coupleable to receive kinetic energy from a kinetic energy source; and
a functional element arranged to travel with the mixing paddle within the interior of the tank, the functional element including any of:
  (a) at least one sensor in sensory communication with the interior of the tank;
  (b) a material extraction conduit in at least selective fluid communication with the interior of the tank and adapted to permit the extraction of material from the interior of the tank;
  (c) a material addition conduit in at least selective fluid communication with the interior of the tank and adapted to permit the addition of a material to the interior of the tank; and
  (d) a heat exchange element in thermal communication with the interior of the tank and adapted to permit the addition or removal of thermal energy from the interior;
wherein the tank comprises a flexible sleeve having an open end proximate to a wall of the tank, having an end protruding into the interior, having at least one exterior wall, and defining a cavity containing the mixing paddle, with the at least one interior wall of the tank and the at least one exterior wall of the sleeve enclosing a volume, such that the sleeve serves as an isolation barrier impermeable to any fluid of the volume;
wherein the functional element is adapted to interact with the flexible sleeve;
wherein any of the mixing paddle and the support rod defines an internal cavity, and wherein any of the following is disposed within the internal cavity: a gas supply conduit, the at least one sensor, at least one electrical conductor, the material extraction conduit, and the material addition conduit.

8. A material processing apparatus comprising:
a hollow tank having an interior bounded by at least one interior wall;
a mixing paddle disposed and adapted to travel within the interior of the tank, the paddle being adapted to engage a pivotally mounted support rod mechanically coupleable to receive kinetic energy from a kinetic energy source; and
a functional element interface adapted for coupling with a functional element arranged to travel with the mixing paddle, wherein the functional element is in fluid communication or sensory communication with the interior, wherein the functional element interface comprises any of a fluid conduit, an electrical conductor, and a communication device;
wherein the tank comprises a flexible sleeve including at least a portion of the functional element interface, said sleeve having an open end proximate to a wall of the tank, having an end protruding into the interior, having at least one exterior wall, and defining a cavity containing the mixing paddle, with the at least one interior wall of the tank and the at least one exterior wall of the sleeve enclosing a volume, said sleeve comprising a material forming a barrier between the volume and the mixing paddle, and between the volume and the portion of the functional element interface within the sleeve.

9. A material processing apparatus comprising:
a hollow tank having an interior bounded by at least one interior wall;
a mixing paddle disposed and adapted to travel within the interior of the tank, the paddle being adapted to engage a pivotally mounted support rod mechanically coupleable to receive kinetic energy from a kinetic energy source; and
a functional element interface adapted for coupling with a functional element arranged to travel with the mixing paddle, wherein the functional element is in fluid communication or sensory communication with the interior;
wherein the functional element interface comprises a gas supply conduit and the functional element comprises a sparger, wherein the gas supply conduit is connectable with the sparger and is adapted to permit passage of gas into the interior of the tank;
wherein the tank comprises a flexible sleeve including at least a portion of the functional element interface, said sleeve having an open end proximate to a wall of the tank, having an end protruding into the interior, having at least one exterior wall, and defining a cavity containing the mixing paddle, with the at least one interior wall of the tank and the at least one exterior wall of the sleeve enclosing a volume, said sleeve comprising a material forming a barrier between the volume and the mixing paddle, and between the volume and the portion of the functional element interface within the sleeve.

10. A material processing apparatus comprising:
a hollow tank having an interior bounded by at least one interior wall;
a mixing paddle disposed and adapted to travel within the interior of the tank, the paddle being adapted to engage a pivotally mounted support rod mechanically coupleable to receive kinetic energy from a kinetic energy source; and
a functional element interface adapted for coupling with a functional element arranged to travel with the mixing paddle, wherein the functional element is in fluid communication or sensory communication with the interior;
wherein the functional element interface comprises at least one of
   (a) a first electrical conductor connectable with the functional element, said functional element comprising a sensor in sensory communication with the interior of the tank; and
   (b) a second electrical conductor connectable with the functional element, said functional element comprising an electrically-driven heat exchange element in thermal communication with the interior of the tank;
wherein the tank comprises a flexible sleeve including at least a portion of the functional element interface, said sleeve having an open end proximate to a wall of the tank, having an end protruding into the interior, having at least one exterior wall, and defining a cavity containing the mixing paddle, with the at least one interior wall of the tank and the at least one exterior wall of the sleeve enclosing a volume, said sleeve comprising a material forming a barrier between the volume and the mixing paddle, and between the volume and the portion of the functional element interface within the sleeve.

11. A material processing apparatus comprising:
a hollow tank having an interior bounded by at least one interior wall;
a mixing paddle disposed and adapted to travel within the interior of the tank, the paddle being adapted to engage a pivotally mounted support rod mechanically coupleable to receive kinetic energy from a kinetic energy source; and
a functional element interface adapted for coupling with a functional element arranged to travel with the mixing paddle, wherein the functional element comprises a sensor in sensory communication with the interior, and wherein the functional element interface comprises a wireless transmitter or receiver connectable with the functional element;
wherein the tank comprises a flexible sleeve including at least a portion of the functional element interface, said sleeve having an open end proximate to a wall of the tank, having an end protruding into the interior, having at least one exterior wall, and defining a cavity containing the mixing paddle, with the at least one interior wall of the tank and the at least one exterior wall of the sleeve enclosing a volume, said sleeve comprising a material forming a barrier between the volume and the mixing paddle, and between the volume and the portion of the functional element interface within the sleeve.

12. A material processing apparatus comprising:
a hollow tank having an interior bounded by at least one interior wall;
a mixing paddle disposed and adapted to travel within the interior of the tank, the paddle being adapted to engage a support rod mechanically coupleable to receive kinetic energy from a kinetic energy source;
a functional element arranged to travel with the mixing paddle within the interior of the tank, the functional element including any of:
   (a) at least one sensor in sensory communication with the interior of the tank;
   (b) a material extraction conduit in at least selective fluid communication with the interior of the tank and adapted to permit the extraction of material from the interior of the tank;
   (c) a material addition conduit in at least selective fluid communication with the interior of the tank and adapted to permit the addition of a material to the interior of the tank; and
   (d) a heat exchange element in thermal communication with the interior of the tank and adapted to permit the addition or removal of thermal energy from the interior; and
a sparger arranged to travel with the paddle for delivering a gas to the interior of the tank;
wherein the tank comprises a flexible sleeve having an open end proximate to a wall of the tank, having an end protruding into the interior, having at least one exterior wall, and defining a cavity containing the mixing paddle, with the at least one interior wall of the tank and the at least one exterior wall of the sleeve enclosing a volume, such that the sleeve serves as an isolation barrier impermeable to any fluid of the volume;
wherein the functional element is adapted to interact with the flexible sleeve.

13. A material processing apparatus comprising:
a hollow tank having an interior bounded by at least one interior wall, said tank comprising a flexible sleeve having an open end connected to a wall of the tank, having an end protruding into the interior, and having at least one exterior wall;

a mixing paddle disposed and adapted to travel within the interior of the tank, the paddle being adapted to engage a support rod mechanically coupleable to receive kinetic energy from a kinetic energy source; and a first conduit;

wherein the flexible sleeve defines a cavity containing the mixing paddle and at least a portion of the first conduit, with the at least one interior wall of the tank and the at least one exterior wall of the sleeve enclosing a volume, such that the sleeve serves as an isolation barrier between the volume and the mixing paddle.

14. The apparatus of claim 13, wherein the first conduit comprises a material extraction conduit in at least selective fluid communication with the interior of the tank and adapted to permit the extraction of material from the interior of the tank.

15. The apparatus of claim 13, wherein the first conduit comprises a material addition conduit in at least selective fluid communication with the interior of the tank and adapted to permit the addition of a material to the interior of the tank.

16. The apparatus of claim 13, further including a functional element arranged to travel with the mixing paddle within the interior of the tank.

17. The apparatus of claim 16, wherein the functional element is selected from the group consisting of:

(a) a first sparger adapted to permit the passage of gas from the first conduit into the interior of the tank;

(b) at least one sensor in sensory communication with the interior of the tank; and (c) a heat exchange element in thermal communication with the interior of the tank and adapted to permit the addition or removal of thermal energy from the interior.

18. The apparatus of claim 13, wherein the first conduit extends substantially from the open end of the sleeve to the end of the sleeve protruding into the interior.

19. The apparatus of claim 13, wherein the first conduit is attached to the end of the sleeve protruding into the interior.

20. The apparatus of claim 13, further including at least one fitment forming a seal between the cavity and the volume, said fitment connected to the first conduit.

21. The apparatus of claim 13, further including a sparger having a first end connected to the first conduit, and further including a second conduit extending from a second end of the sparger.

22. The apparatus of claim 21, wherein the second conduit extends within the sleeve.

23. The apparatus of claim 21, wherein the second conduit includes a plug.

24. The apparatus of claim 13, further including a weld for attaching the first conduit to the sleeve.

* * * * *